(12) United States Patent
de Souza et al.

(10) Patent No.: US 7,098,219 B2
(45) Date of Patent: Aug. 29, 2006

(54) INHIBITORS OF CELLULAR EFFLUX PUMPS OF MICROBES

(75) Inventors: Noel John de Souza, Mumbai (IN); Mahesh Vithalbhai Patel, Aurangabad (IN); Shrikant V Gupte, Aurangabad (IN); Dilip J Upadhyay, Mumbai (IN); Milind Chintaman Shukla, Aurangabad (IN); Nishith C Chaturvedi, Aurangabad (IN); Satish B Bhawsar, Aurangabad (IN); Sheela Chandresekharan Nair, Aurangabad (IN); Mohammed A Jafri, Uttar Pradesh (IN); Habil Fakhruddin Khorakiwala, Mumbai (IN)

(73) Assignee: Wockhart Limited, Mumbai (IN)

( * ) Notice: Subject to any disclaimer, the term of this patent is extended or adjusted under 35 U.S.C. 154(b) by 0 days.

(21) Appl. No.: 09/919,347

(22) Filed: Jul. 31, 2001

(65) Prior Publication Data

US 2002/0177559 A1    Nov. 28, 2002

Related U.S. Application Data

(60) Provisional application No. 60/287,104, filed on Apr. 27, 2001, provisional application No. 60/286,291, filed on Apr. 25, 2001, provisional application No. 60/222,201, filed on Aug. 1, 2000.

(51) Int. Cl.
| C07D 471/04 | (2006.01) |
| C07D 471/02 | (2006.01) |
| A61K 31/44  | (2006.01) |
| A61K 31/47  | (2006.01) |

(52) U.S. Cl. .............. 514/292; 514/294; 514/300; 514/311; 514/314; 546/81; 546/95; 546/96; 546/122; 546/156

(58) Field of Classification Search ........ 514/292, 514/294, 300, 311, 314; 546/81, 95, 96, 546/122, 156
See application file for complete search history.

(56) References Cited

U.S. PATENT DOCUMENTS

| 3,924,042 A | 12/1975 | Gerster et al. ............. 424/258 |
| 3,984,403 A | 10/1976 | Fujisawa et al. ............ 260/243 |
| 3,985,882 A | 10/1976 | Gerster ..................... 424/258 |
| 4,051,247 A | 9/1977 | Schuppan et al. .......... 424/258 |
| 4,382,892 A | 5/1983 | Hayakawa et al. ........ 260/243.3 |
| 4,399,134 A | 8/1983 | Ishikawa et al. ............ 424/246 |
| 4,404,207 A | 9/1983 | Stern ...................... 424/258 |
| 4,416,884 A | 11/1983 | Ishikawa et al. ............ 424/250 |
| 4,443,447 A | 4/1984 | Gerster et al. ........ 424/248.53 |
| 4,472,406 A | 9/1984 | Gerster ..................... 424/258 |
| 4,472,407 A | 9/1984 | Stern ........................ 424/258 |
| 4,535,161 A | 8/1985 | Hayakawa ................... 546/94 |
| 4,552,879 A | 11/1985 | Ishikawa et al. ............ 514/253 |
| 4,563,459 A * | 1/1986 | Grohe et al. ........... 514/253.08 |
| 4,594,347 A | 6/1986 | Ishikawa et al. ............ 514/252 |
| 4,599,418 A | 7/1986 | Irikura et al. ............... 544/361 |
| 4,638,067 A | 1/1987 | Culbertson et al. ........... 546/15 |
| 4,642,355 A | 2/1987 | Nakamura et al. .......... 548/533 |
| 4,665,079 A | 5/1987 | Culbertson et al. ......... 514/312 |
| 4,777,175 A | 10/1988 | Culbertson et al. ......... 514/300 |
| 4,822,801 A | 4/1989 | Domagala et al. .......... 514/312 |
| 4,874,764 A | 10/1989 | Ueda et al. ................ 514/254 |
| 4,894,458 A | 1/1990 | Masuzawa et al. ......... 546/156 |
| 4,935,420 A | 6/1990 | Ueda et al. ............... 514/235.2 |
| 5,051,509 A | 9/1991 | Nagano et al. ............. 546/156 |
| 5,097,032 A | 3/1992 | Domagala et al. .......... 546/156 |
| 5,185,337 A | 2/1993 | Fujii et al. ................. 514/254 |
| 5,607,942 A | 3/1997 | Petersen et al. ............ 546/200 |
| 5,639,886 A | 6/1997 | Zerbes et al. .............. 546/155 |
| 5,677,316 A | 10/1997 | Ao et al. ................... 514/312 |
| 5,859,026 A * | 1/1999 | Ito |
| 5,869,661 A | 2/1999 | Ochi et al. ................. 544/128 |
| 5,889,009 A * | 3/1999 | Miyake |
| 5,989,832 A | 11/1999 | Trias et al. |
| 6,034,100 A | 3/2000 | Adachi et al. .............. 514/312 |
| 6,121,285 A * | 9/2000 | Takemura |
| 6,184,388 B1 * | 2/2001 | Takemura |
| 6,329,391 B1 * | 12/2001 | Ledoussal ................... 514/313 |

FOREIGN PATENT DOCUMENTS

| CN | 1097751 | 1/1995 |
| EP | 0230295 | 7/1987 |
| EP | 0241206 | 10/1987 |
| EP | 0287951 | 10/1988 |
| EP | 0300735 | 1/1989 |
| EP | 0304087 | 2/1989 |
| EP | 0342675 | 11/1989 |
| EP | 0394553 | 10/1990 |
| EP | 0541086 | 5/1993 |
| EP | 0572259 | 12/1993 |
| EP | 0908181 | 4/1999 |
| EP | 0919553 | 6/1999 |
| JP | 57081486 | 5/1982 |
| JP | 57176987 | 10/1982 |
| JP | 58090511 | 5/1983 |

(Continued)

OTHER PUBLICATIONS

Kurokawa, J of the American Academy of Dermatology, vol. 25(4), oo 674-681, Oct. 1991.*

(Continued)

Primary Examiner—D. Margaret Seaman
(74) Attorney, Agent, or Firm—Ladas & Parry

(57) ABSTRACT

Compounds are described which are efflux pump inhibitors of cellular efflux pumps of microbes. Also described are methods of preparing such compounds, methods of using such efflux pump inhibitor compounds and pharmaceutical compositions which include such compounds.

32 Claims, No Drawings

FOREIGN PATENT DOCUMENTS

| | | |
|---|---|---|
| JP | 63192753 | 8/1988 |
| JP | 02131483 | 5/1990 |
| JP | 02188570 | 7/1990 |
| JP | 02188589 | 7/1990 |
| JP | 05339238 | 12/1993 |
| WO | 9420105 | 9/1994 |
| WO | 9724128 | 7/1997 |
| WO | 9731000 | 8/1997 |
| WO | 9744034 | 11/1997 |
| WO | 9914214 | 3/1999 |
| WO | 9926940 | 6/1999 |
| WO | 0018404 | 4/2000 |
| WO | 0068229 | 11/2000 |
| WO | 0185095 | 11/2001 |
| WO | 0185728 | 11/2001 |
| WO | 0209758 | 2/2002 |
| ZA | 8502369 | 12/1985 |

OTHER PUBLICATIONS

Haustein, J. of Dermatological Treatment, vol. 8, pp. 87-92, 1997.*
Oizumi, N., et al. "Relationship between mutations in the DNA gyrase and topoisomerase IV genes and nadifloxacin . . . *Staphylococcus aureus*" J. Infect Chemotherapy, vol. 7, p. 191-194, (2001).
Haustein, U-F., et al. "Topical quinolone nadifloxacin (OPC-7251) in bacterial skin disease: clinical evaluation . . . testing" J. of Dermatological Treatment , vol. 8, p. 87-92, (1997).
Kurokawa, J of the American Academy of Dermatology, 25(4), pp. 674-681, Oct. 1991.
Mergler et al. Proceedings of the 12$^{th}$ American Peptide Symposium. Reference cited on p. 2 of EPA 0953577.
Alsina, et al. *Tetrahedon Letters*, v38 n5, (1997) 883-886.
Edwards et al. *J. Med. Chem.*, v37 n22 (1994) 3749-3757.
A.M. Dhople, M.A. Tbanez: "In vivo susceptibility of mycobacterium leprae to ofloxacin either singly or in combination with rifampicin and rifabutin" Arzeimittel-Forschung, vol. 44, No. 4, 1994, pp. 563-565.
Haustein et al. *J. of Dermatological Treatment* , v8 (1997) 87-92.
Bundgaard, H. *Design of Prodrugs*. (1985) pp. 1-3.
Hashimoto et al. *Chem. Pharm. Bull*. V44, n4 (1996) pp. 642-645.
Irish, D. et al. *J. of Hospital Infection*, v39 (1998) pp. 19-26.
Kido, M. et al. *Chem. Pharm. Bull*. V42, n4 (1994) pp. 872-876.
Sloan et al. *Physics and Chemistry of the Organic Solid State*, eds. D. Fox, Labes and Weissberer, Interscience Publishers, (1963) 179-182.
Takahashi et al. *Arzheim-Forsc/Drug Res.*, 45(1), Nr. 2 (1995), 199-197.
Morita, S. et al. *Tetrahedoni: Assymetry*, v6, n1 (1995) pp. 245-254.
Morita, S. et al. *Chem. Pharm. Bull.*, 38(7) (1990) 2027-2029.
Ishikawa et al. *Chem. Pharm. Bull.*, 37(8) (1989) 2103-2108.
English translation of Yamada, H. et al. *Iyahukin Kenkyu*, v31, n8 (2000) pp. 519-524.
English translation of Yamada, H. et al. *Iyahukin Kenkyu*, v31, n8 (2000) pp. 525-528.
Berge et al. *J. of Pharmaceutical Sciences*, 66(1) (1977) 1-19.
Abstract of Koike, M. et al. *Iakuhin Kenkyu*, v21, n5 (1990) pp. 998-1021.
Abstract of Koike, M. et al. *Iyakuhim Kenkyu*, v21, n5 (1990) pp. 1022-1033.
Abstract of Fujita, S. et al. *Iyakuhin Kenkyu*, v21, n6 (1990) pp. 1156-1176.
Abstract of Koike, M. et al. *Yakubutsu Dotai*, v5, n2 (1990) pp. 199-208.
Abstract of Yasuo, A.. et al. *Yakuri to Chiryo*, v18, n4 (1990) pp. 1717-1730.
Abstract of Hayakawa, R. et al. *Hifu*, v32, n2 (1990) pp. 217-230.
Abstract of Asada, Y. et al. *Yakuri to Chiryo*, v18, n4 (1990) pp. 1717-1730.
Abstract of Awogi, T. et al. *Iyakuhin Kenkyu*, v21, n4 (1990) pp. 626-635.
Abstract of Matsuzawa, A. et al. *Iyakuhin Kenkyu*, v21, n4 (1990) pp. 636-646.
Abstract of Nagao T. et al. *Iyakuhin Kenkyu*, v21, n4 (1990) pp. 647-662.
Abstract of Matsuzawa, A. et al. *Iyakuhin Kenkyu*, v21, n4 (1990) pp. 633-670.
Abstract of Hashimoto, K.. et al. *Iyakuhin Kenkyu*, v21, n4 (1990) pp. 670-677.
Abstract of Furukawa, M. et al. *Iyakuhin Kenkyu*, v21, n5 (1990) pp. 989-997.
Abstract of Kojima, K. et al. *Iyakuhin Kenkyu*, v21, n5 (1990) pp. 1034-1052.
Abstract of Nakagiri, N. et al. *Iyakuhin Kenkyu*, v21, n6 (1990) pp. 1144-1155.
Abstract of Aoki, M. et al. *Iyakuhin Kenkyu*, v21, n6 (1990) pp. 1177-1202.
Abstract of Matsuzawa, A. et al. *Iyakuhin Kenkyu*, v22, n1 (1990) pp. 61-76.
Abstract of Kurokawa I. et al. *J. Am. Acad. Dermatol.*, v25, n4 (1991) pp. 674-681.
Abstract of Bojar, R. et al. *J. of Investigative Dermatology*, v103, n3 (1994) pp. 405.
E.M. Mateu-de-Antonio, M. Martin: "In vitro efficacy of several antimicrobial combinations against *Brucella canis* and *Brucella melitensis* strains isolated from dogs" Vet. Microbiology, vol. 45, No. 1, 1995, pp. 1-10.
Abstract of Smith, C.M. et al. *J. of Investigative Dermatology*, v108, n3 (1997) p. 123.
Abstract of Hayakawa, R. et al. *Hifu*, v40, n2 (1998) pp. 165-171.
Fujio, N. et al. *Yakuri to Chiryo*, v26, n7 (1998) pp. 1119-1132.
Kido, M. et al. *Chem. Pharm. Bull.*, v44, n2 (1996) pp. 421-423.
Miller, M.A. et al. *Infection Control and Hospital Epidemiology*, v17, n12 (1995) pp. 811-813.
Nishijima, S. et al. *The Journal of Int'l Medical Research*, v23, (1995) pp. 328-334.
Nishijima, S. et al. *Journal of Dermatology*, v22, (1995) pp. 153-155.
Nishijima, S. et al. *The Journal of Int'l Medical Research*, v24, (1996) pp. 12-16.
Nishijima, S. et al. *Journal of Dermatology* , v21, (1994) pp. 233-238.
Udo, E. E. et al. *J. of Hospital Infection*, v26, (1994) pp. 157-165.
Abstract of Kurokawa, I. et al. *European J. of Dermatolgoy*, v9, n1 (1999) pp. 25-28.
Abstract of Komagata. et al. *Japanese Journal of Antibiotics*, v51, n2 (1998) pp. 130-136.
Abstract of Gollnick, H. et al. *Dermatology*, v196, n1(1998) pp. 119-125.
Abstract of Nishijima, S. et al. *J. of Int'l Medical Research*, v25, n4 (1997) pp. 210-213.
Abstract of Nishijima, S. et al. *J. of In'tl Medical Research*, v24, n6 (1996) pp. 473-477.
Abstract of Akamatsu, H. et al. *J. of Int'l Medical Research*, v23, n1 (1995) pp. 19-26.
Abstract of Takahashi, N. et al. *Arzneimittel-Forschung*, v45, n2 (1995) p. 195.
Abstract of Takahashi, N. et al. *Arzneimittal-Forschung*, v44, n11 (1994) 1pp. 265-1268.
Abstract of Patel, M.V. 39$^{th}$ ICAAC at San Diego Poster No. F0558 (Sep. 26-29, 1999).
Chemical Abstract: Doc. No. 123:334723 Vogt, K. et al. *Drugs*, v49, Suppl. 2 (1995).
Chemical Abstract: Doc. No. 123:34716 Nishijima et al. *Drugs*, v49, Suppl.2 (1995).
Chemical Abstract: Doc. No. 124:21098 Bojar, R.A. et al. *Drugs*, v49, Suppl.2 (1995).
Chemical Abstract: Doc. No. 122:213914, *Tetrahedon: Asymmetry*, v6, No. 1 (1995).
Chemical Abstract: Doc. No. 119:4810 Vogt, K. et al. *Eur. J. Clin. Microbiol. Infect.*
Chemical Abstract: Doc. No. 113:2131188 Morita, S. et al. *Chem. Pharm. Bull.* v38, n7.

Chemical Abstract: Doc. No. 112:229223, Muto, N. et al. *J. Immunoassay*. v11 n1.

Chemical Abstract: Doc. No. 112: 191305, Koike, M. et al. *J. Chromatogr.* v526, n1.

Chemical Abstract: Doc. No. 112: 178631, Ishikawa, H. et al. *Chem. Pharm. Bull.* v37.

Chemical Abstract: Doc. No. 112:52083, *Chemotherapy*, v37, n9 (1989) pp. 1160-1178.

Abstract of Iwahara, K. et al. *European J. of Dermatolgoy*, v9, n4 (1999) pp. 276-277.

Abstract of Radl, s. et al. *Archiv der Pharmazie*, v329, n3 (1996) pp. 115-119.

Abstract of Andriole, V.T., *Drugs*, v46, Suppl.3 (1993) pp. 1-7.

Ball, Peter. "The Quinolones: History and Overview", Chapter 1, The Quinolones, Second Ed. Academic Press, 1998. pp. 1-28.

Domagala, John M. *Journal of Antimicrobial Chemotherapy* (1994) 33, 685-706.

Suto, Mark J. et al. *J. of Med. Chem.* (1992) 35, 4745-4750.

Abstract of Yamakawa, T. et al. *J. Antimicobial Chemotherapy*, 49(3) Mar. 2002, 455-465.

Hooper, David C. *Drug Resistance Updates* (1999) 2, 38-55.

Ince, Dilek and David C. Hoope. *Antimicrobial Agents and Chemotherapy* (Oct. 2001) 45(10), 2755-2764.

Fournier, Benedicte and David C. Hooper. *Antimicrobial Agents and Chemotherapy*, (Jan. 1998) 42(1) 121-128.

Zhao, Xilin et al. *Antimicrobial Agents and Chemotherapy*, (Apr. 1998) 42(4) p956-958.

Breines, David M. et al. *Antimicrobial Agents and Chemotherapy*, (Jan. 1997) 41(1) 175-179.

Fournier, Benedicte, et al. *Journal of Bacteriology*, (Feb. 2000) 182(3) 664-671.

Mandell, Lionel et al. *CIP* (2001) 32, Suppl 1, S72-S79.

Gootz, Thomas D. and Katherine E. Brighty. "Chemistry and Mechanism of Action of the Quinolone Antobacterials", The Quinolones, Second Ed. Chap 2. Academic.

Takenouchi, Takashi et al. *Antomicrobial Agents and Chemotherapy*, (Aug. 1996) 40(8) pp. 1835-1842.

Zhao, Xilin, et al. *Proc. Natl. Acad. Sci. USA*, (Dec. 1997) vol. 94, pp. 13991-13996.

Takei, Masaya et al. *Antimicrobial Agents and Chemotherapy*, (Dec. 2001), 45(12), pp. 3544-3547.

Ince, Dilek et al. *Antimicrobial Agents and Chemotherapy*, (Dec. 2000), 44(12) pp. 3344-3350.

Oizumi, Nbuyuki et al. *J. Infect. Chemother.*, (2001) 7: 191-194.

Jaen-Oltra, Jose et al.: "Artificial neural network applied to prediction of fluorquinolone antibacterial activity by topological methods" Journal of Medicinal Chemistry (2000).

Chu, Daniel T. W. et al.: "Synthesis and structure-activity relationships of novel arylfluoroquinolone arylfluoroquinolone antibacterial agents" J. Med. Chem. (1995), 28(11), 1558-64.

H.C. Nfu, N.X. Chin. "In vitro activity of fleroxacin in combination with other antimicrobial agents" Amer. Journal of Medicine, vol. 94, No. 3A, 1993, pp. 98-165.

N.X. Chin, H.C. Neu: "Combination of ofloxacin and other antimicrobial agents" J. of Chemotherapy (Florence), vol. 2, No. 6, 1990, pp. 343-347.

P. Van der Auwera E.A.: "Comparative in vitro activity of Cl934, a new fluoroquinolone, alone and in combination with coumermycin" Drugs under Experimental and Clinical Research, vol. 13, No. 3, 1987, pp. 125-132.

Abstract of South African patent 8502369, dated Dec. 24, 1985.

Abstract of Chinese Patent 1097751 dated Jan. 25, 1995.

Abstract of Masateru Ohta and Hiroshi Koga, Journal of Medicinal Chemistry (1991), 34 (1), 131-9.

Abstract of Nobuhisa Masuda, et al., Antimicrobial Agents and Chemotherapy (2000), 44 (12), 3322-3327.

Abstract of Qingsen Yu, et al., Huaxue Yanjiu Yu Yingyong (1995), 7 (3), 301-304.

Abstract of Seiji Morita, et al., Chemical & Pharmaceutical Bulletin (1995), 43 (12), 2246-52.

Joseph P. Sanchez, et al., *Quinolone Anitbacterial Agents. Synthesis and Structure-Activity Relationships of a Series of Amino Acid Prodrugs of Racemic and Chiral 7-(3-Amino-I-pyrrolidinyl)quinolones. Highly Soluble Quinolone Prodrugs with in Vivo Pseudomanas Activity* , J. Med. Chem. (1992), 35, 1764-1773.

* cited by examiner

INHIBITORS OF CELLULAR EFFLUX PUMPS OF MICROBES

This application claims the benefit of U.S. Provisional Application(s) No(s).: APPLICATION NO(S).: FILING DATE 60/222,201 Aug. 1, 2000 60/286,291 Apr. 25, 2001 60/287,104 Apr. 27, 2001 and incorporates the same by reference.

This invention relates to compounds with efflux pump inhibitor properties, and which are therefore compounds which inhibit cellular efflux pumps of bacteria or other microbes. Such efflux pump inhibitors are useful, for example, against antibiotic-resistant microbial pathogens, for treating microbial infections by reducing the export of a co-administered antimicrobial agent or by preventing the export of a compound synthesized by microbes (e.g. bacteria, fungi) to allow or improve their growth. Thus, this invention also provides processes for preparation of such efflux pump inhibitors, compositions which include such efflux pump inhibitors, and the use of the compounds and compositions in methods for treatment of microbial infections.

BACKGROUND OF THE INVENTION

Microbes are known to have developed the ability to evolve different mechanisms of self-defense against antimicrobial agents. In particular, bacterial and fungal pathogens have developed mechanisms of resistance to antibiotics and antimicrobial agents used to inhibit their growth, or to treat infections by them in humans, animals and tissue cultures. As a result, treatment regimens can be adversely affected or, in some cases rendered ineffective.

One of the most frequently employed resistance strategies in both prokaryotes and eukaryotes is the transmembrane-protein-catalyst extrusion of drugs from the cell, with these proteins acting like bilge pumps, reducing the intracellular drug concentration to subtoxic levels. (M. Ines Vorges-Walmsley et.al., Trends in Microbiology, 2001, 9: 71–79).

Recent developments in the efflux area include the discovery of new monodrug efflux systems, as well as the realisation of the importance of multidrug efflux systems (H. Nikaido and H. I. Zgurskaya, Current Opinion in Infectious Diseases, 1999, 12: 529). In gram-negative bacteria, for example, single component efflux pumps extrude their substrates into the periplasmic space as is done by the transposon-encoded tetracycline- and chloramphenicol-specific pumps, TetA and CmlA, respectively, and the MDR pump MdfA encoded in the chromosome of Escherichia coli.

Bacterial genomes sequenced to date almost invariably contain genes apparently coding for multidrug efflux pumps. Multidrug efflux as a major cause of intrinsic drug resistance in many microorganisms, or overproduction of intrinsic pumps, or acquisition of pump genes from external sources, all play a prominent role, often resulting in high levels of resistance. Examples of multicomponent efflux pumps, belonging mainly to the resistance-modulation-division (RND) family members, found mostly in gram-negative bacteria, include the MDR pumps AcrAB-TolC and MexAB-OprM from E. coli and Pseudomonas aeruginosa. Interplay between efflux pumps may provide either additive or multiplicative effects on drug resistance (A. Lee et al., J. of Bacteriology, 2000, 182: 3142). MexAB-OprM, MexCD-OprJ, MexEF-OprN, MexXY-OprM, AcrAB-TolC, AcrEF, MarA, SoxS, or/and Tet pump/s are known to be present in Gram negative organisms such as P. aeruginosa and E. coli and are reviewed in recent publications and papers, such as K. K. Y. Wong et. al., J. of Bacteriology, 2001, 183: 367–374; K. Poole, Antimicrobial Agents and Chemothero, 2000, 44: 2233–2241; R Srikumar et. al., Abstracts of the 40th Interscience Conference on Antimicrobial Agents and Chemother., 2000, Abstr. 441: 74; Xian Zhi Li et. al., Journal of Antimicrob. Chemother., 2000, 45: 433–436; Koronakis et. al., Nature, 2000, 405: 914 –919; M Oethinger, et. al., Antimicrob. Agents and Chemother., 2000, 44: 10–13; W. V. Kern, et. al., Antimicrob. Agents and Chemother., 2000, 44: 814–820; O Lomovskaya, et. al., Antimicrob. Agents and Chemother., 1999, 43: 1340–1346. Active efflux has been shown to be the primary or molecular mechanism of a fluoroquinolone resistance in Salmonella enterica Serovar Typhimurium (E Giraud et. al., Antimicrob. Agents and Chemother., 2000, 44: 1223–1228) and in Pseudomonas aeruginosa isolates from cystic fibrosis patients (S Jalal et. al., Antimicrob. Agents and Chemother., 2000, 44: 710–712). Efflux mediated aminoglycoside and macrolide resistance in Burkholderia pseudomallei, the causative agent of meliodosis has been described in R A Moore et. al., Antimicrob. Agents and Chempther., 1999, 43: 465–470.

Efflux transporters are also among different mechanisms responsible for the resistance to antibiotics displayed by gram-positive bacteria and mycobacteria, particularly aerobic gram-positive cocci. The multidrug transporter NorA, belonging to the major facilitator superfamily (MFS) transporters, contributes to the resistance of Staphylococcus aureus to fluoroquinolone antibiotics. A minireview describes effllux-mediated resitance to fluoroquinolones in Gram-positive bacteria and the mycobacteria (K Poole, Antimicro. Agents and Chemother., 2000, 44: 2595–2599). To the MFS transporters also belong the Bmr and QacA/QacB efflux pumps of Gram positive bacteria, and EmrB of E. coli (H. Nikaido, Current Opinion in Microbiology, 1: 516–523). A structure based mechanism for drug binding by multidrug transporters is recently proposed using the BmrR protein from Bacillus subtilis and the multidrug transporter MdfA from E. coli (E. E. Zheleznova et. al., Trends in Biological Sciences 2000, 25: 39–43), which mechanism is also putatively considered for the QacA/QacB efflux system of S. aureus . New MFS pumps include PmrA (a homolog of NorA) of Streptococcus pneumoniae (J. Broskey etl.al., Journal of Antimcro. Chemother., 2000, 45: Suppl. S1, 95–99; M J Gill et. al., Antimicrob. Agents and Chemother., 1999, 43: 187–189) and Tap of Mycobacterium fortuitum and M. tuberculosis. Recently, NorM, which pumps out fluoroquinolones and some cationic agents was found to be outside the MFS transporter class. The role of membrane-fusion protein (MFP) structural homologues recently identified in low G+C Gram positive bacteria that lack an outer membrane, as essential transport accessory proteins with transporters of the ATP-Binding Cassette (ABC) super family has been described (K. T. Harley et. al., Molecular Microbiol., 2000, 38: 516–517).

The Mef efflux system mediates large fractions of erythromycin-resistant clinical isolates of S. pneumoniae (N. J. Johnston et al., Antimicrob Agents Chemother., 1998, 42: 2425; T. Nishijma et al., J. Antimicrob Chemother, 1999, 43: 637). Beta-haemolytic Streptococci and pneumococci resistant to erythromycin due to the prsence of MefA efflux pumps in Streptococcus pyogenes, MefE pumps in S. pneumoniae, and an M phenotype bearing S. agalactiae possessing MefA or MefE pumps are found to be emergent and prevalent in Europe (C Arpin et. al., J. Antimicrob. Chemother., 1999, 44: 133–138; E. Giovanetti et. al., Antimicrob. Agents and Chemother., 1999, 43: 1935–1940).

Efflux and drug resistance in fungi and protozoa have also been described (T. G. White et al., Clin Microbiol Rev 1998, 11: 382; D. Sanglard, Drug Resistance Updates1998, 1: 255; B. Papadopoulou et al., Drug Resistance Updates 1998, 1: 266; E. Orozao et al., Drug Resistance Updates, 1999, 2:188).

In summary, the above discussion indicates that cellular factors affecting transport (both active and passive transport) of antibiotics into bacterial cells are important components of antibiotic resistance for many microbial species.

One strategy to target resistance mechanisms of microbial self-defense is to find inhibitors of microbial efflux pumps and, in particular of bacterial and fungal efflux pumps.

There is disclosed in PCT Patent publication WO 96/33285 and U.S. Patent application U.S. Pat. No. 5,989, 832 with priority in U.S. application Ser. No. 08/427,088 and PCT/US96/05469, methods for screening for inhibitors of microbial efflux pumps, efflux pump inhibitors, compositions containing such efflux pump inhibitors, and methods for treating microbial infections using those compositions, but unlike the efflux pump inhibitors of the present invention, the efflux pump inhibitors disclosed are dipeptide amides specifically inhibiting a *Pseudomonas aeruginosa*-type efflux pump. There is disclosed in PCT Patent publication WO/001714, with priority in U.S. application Ser. No. 09/108,906, compounds which have efflux pump inhibitor activity, methods of using such efflux pump inhibitors and pharmaceutical compositions which include such compounds, but unlike the efflux pump inhibitors of the present invention, the efflux pump inhibitors disclosed are dipeptide amide derivatives demonstrating pump inhibitory activity against *P. aeruginosa* strains containing singular efflux pumps and multiple efflux pumps.

Patent WO 99/17791, with U.S. priority in 60/060,898 discloses a method for inhibiting the selection or propagation of a bacterial mutant that overexpresses an efflux pump wherein the inhibitor disclosed is the dipeptide amide, L-phenylalanyl-L-arginyl-beta-naphthylamide (MC'-207, 110), which is unlike the efflux pump inhibitor compounds of the present invention.

U.S. Pat. Nos. 6,245,746, 6,114,310 and WO 9937667 all with U.S. priority in U.S. application Ser. No. 09/012,363 disclosed methods of using efflux pump inhibitors which increase the susceptibility of microbes in particular *P. aeruginosa* strains to antimicrobial agents and pharmaceutical compositions which include such compounds.

U.S. Pat. No. 6,204,729 describes peptidomimetic efflux pump inhibitors; secondary amide containing benzoxazole derivatives, methods of using such efflux pump inhibitor compounds and pharmaceutical compositions which include such compounds.

Patent WO 00/32196, with U.S. priority in 60/110,841, discloses inhibitors of multidrug transport proteins which may be used in combination with existing antibacterial agents and/or antifungal agents, wherein the inhibitor is an indole or a urea or an aromatic amide or a quinoline, all of which inhibitors are unlike the efflux pump inhibitor compounds of the present invention. In addition, the inhibitors disclosed in patent WO 00/32196 are specifically inhibitors of bacteria expressing a norA pump, or a fungus expressing a multidrug transport protein.

Novel inhibitors of the NorA multidrug transporter of *S. aureus* having structurally diverse chemical structures were also described by P. N. Markham et al., (Antimicrob. Agents & Chemother., 1999, 43: 2404), among which the more active compounds include (a) those containing an indole moiety like the previously known inhibitor, reserpine, (b) biphenyl urea derivatives, (c) a substituted pyrimidinone derivative and (d) compounds INF 240 and INF 277, but they are all unlike the efflux pump inhibitor compounds of the present invention.

Another inhibitor of the NorA MDR pump in a pathogenic *S. aureus* strain is 5'-methoxyhydnocarpin (F. R. Stermitz et al., Proc. New York Acad. of Sci., 2000, 97: 1433), which has a structure unlike the efflux pump inhibitor compounds of the present invention.

Nocardamin, a cyclopeptide, was found to be a general antagonist of a tetracycline efflux pump from *S. aureus*. It has a structure unlike the efflux pump inhibitor compounds of the present invention.

Minocycline and 1,1-dimethyl-5-(1-hydroxypropyl)-4,6,7-trimethylindan (Ro 07-3149) inhibit the active tetracycline efflux pump in *S. aureus* 743 (T.Hirata et al., Biol Pharm Bull, 1998, 21:678). Both the compounds have a structure unlike the efflux pump inhibitor compounds of the present invention.

(±)-3-(2-chloro,5-bromophenyl) ethyl-4-fluoropiperidine as an example of 3-arylpiperidines has recently been described as potentiator of existing antibacterial agents against *E. coli* (A. Thorarensen et. al., Bioorg. and Medicinal Chem. Letters, 2001, 11: 1903–1096). The 3-arylpiperidine compounds have a structure unlike the efflux pump inhibitor compounds of the present invention.

To our knowledge no drug like organic molecule has been identified, described or proposed as an inhibitor of Mef efflux pump.

Deficiencies abound in the efflux pump inhibitors disclosed in the art prior to our present invention.

Reserpine is not a usable compound for therapy because of its neurotoxicity at the concentration required for efflux pump inhibition.

The inhibitors of single drug and multidrug transporters such as the dipeptide amide, MC'-207,110, are broad in specificity, inhibiting all three RND systems of *P. aeruginosa* involved in fluoroquinolone efflux, but have not been shown to be effective against pumps of other strains, for instance a NorA pump. Moreover, the methods employed to demonstrate their efflux pump inhibitory properties are mainly in vitro methods. For demonstration of in vivo activity, recourse has had to be taken to parenteral administration (cf. T. E. Renau et al, J. Med. Chem.,1999, 42, 4928), rather than oral administration, as it is generally known that oral bioavailability is poor for compounds of a peptidic nature.

The series of inhibitors described in WO 00/32196 and by Markham et al (vide infra) have been minimally and incompletely profiled in terms of their efficacy, safety and tolerability, which has yet to be demonstrated in in vivo models.

Potent inhibitors of microbial efflux pumps is thus an important goal for the improved control of infectious diseases, allowing a renaissance for drugs that are no longer effective owing to their efflux (K. Poole, Journal of Pharmacy and Pharmacology, 2001, 53: 283–294). The current inventors have synthesised screened and identified novel inhibitors of cellular efflux pumps of microbes. Distinctive structural features characterise the difference sets of efflux pump inhibitors for different microorganisms as will be described in the following description.

SUMMARY OF THE INVENTION

The present invention describes compounds of the formula I as novel microbial efflux pump inhibitors,

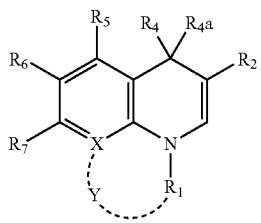

Formula I wherein,

- $R_1$=H, $C_{1-6}$ alkyl, $C_{3-6}$ cycloalkyl or optionally substituted aryl, aralkyl, arylaminoalkyl, aryloxyalkyl or arylS(O)$_t$alkyl, where t=0,1 or 2, or when X is C and the nitrogen atom to which $R_1$ is linked forms an optionally substituted 4-, 5-, 6- or 7-membered ring with X of the adjacent ring, the ring optionally containing one or more hetero atoms selected from nitrogen, oxygen or sulfur atoms, said heteroatom(s) represented by Y, preferably $R^1$ is $CH_2CH_2$—, $CH_2Y$—, $CH_2CH_2CH_2$—, $CH_2CH_2Y$—, $CH_2CH_2CH_2CH_2$— and $CH_2CH_2CH_2Y$— where Y represents for NH, O, or S. If the ring is substituted, the substituent is $C_{1-6}$ alkyl group.
- $R_2$ H, CHO, COOR$_3$, or CONHR$_{13}$, where $R_{13}$=H or the NHR$_{13}$ of CONHR$_{13}$ is the residue of one of the 20 naturally occurring amino acids: alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof, or combinations of these amino acids to give dipeptidyl or tripeptidyl or polypeptidyl residues.
- $R_3$=H, $C_{1-6}$ alkyl, $C_{3-6}$ cycloalkyl, aryl, aralkyl, arylaminoalkyl, aryloxyalkyl, arylS(O)$_t$alkyl, where t=0,1 or 2, $(CH_2)_nCH(R_{14})OC(=O)R_{15}$, $(CH_2)_nCH(R_{14})C(=O)OR_{15}$ wherein n=0–6, $R_{14}$=H, or $CH_3$; and $R_{15}$=$C_2H_5$, or $C(CH_3)_3$ or $R_3$ is

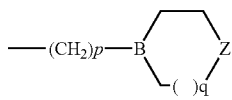

wherein B=CH or N, and when B=CH, Z=NH or NCH$_3$, and when B=N, Z=CH, O, NH, S or NCH$_3$; p=0–2; q=0–2,

- $R_4$=H, $R_{4a}$=H, or $R_4$ and $R_{4a}$ taken together are oxo (=O), or thio (=S).
- $R_5$=H, $C_{1-5}$ alkyl, amino, alkylamino, or acylamino.
- $R_6$=H, $C_{1-6}$ alkyl, halo such as F, Cl, Br, or I, amino, or hydroxy;
- $R_7$=OH, halo such as F, Cl, Br, or I, or
  NR$_9$R$_{10}$ wherein $R_9$ and $R_{10}$ are the same or different and represent H, $C_{1-6}$ alkyl or $(CH_2)_nOA$, or $R_9$ is H and $R_{10}$ is a 4-membered, 5-membered, 6-membered, or 7-membered carbocyclic, mono or bicyclic ring or mono or bicyclic heterocyclic ring linked to the nitrogen of NR$_9$R$_{10}$ through an atom of the heterocycle other than the heterocyclic atom or $R_9$ and $R_{10}$ taken together with the nitrogen atom to which they are attached form part of a heterocycle which heterocycle is monocyclic or bicyclic.

The carbocycle and the heterocycle are optionally substituted at any position of the carbocyclic or heterocyclic group with COOR$_3$, CONHR$_{13}$, OA, $C_{1-6}$ alkyl, $C_3$–$C_6$ cycloalkyl, aralkyl, trifluoroalkyl, substituted $C_{1-6}$ alkyl, or N R$_{16}$R$_{17}$.

Substituents of the alkyl group are selected from OA, NR$_{16}$R$_{17}$, or a halogen atom. $R_{16}$ and $R_{17}$ are the same or different and represent H or $C_{1-6}$ alkyl, or where one of $R_{16}$ and $R_{17}$ is hydrogen and the other of $R_{16}$ and $R_{17}$ is $C_3$–$C_6$ cycloalkyl, or substituted $C_{1-6}$ alkyl or R16 and R17 taken together with the nitrogen atom form a heterocycle. When $R_{16}$ or $R_{17}$ is a substituted alkyl group, the substituent is selected from NR$_{16}$R$_{17}$, alkanoyl or aminoalkanoyl or $R_7$=NHOA, NHCOOR$_{11}$, or NH(CH$_2$)$_n$NR$_9$R$_{10}$;

or $R_7$=

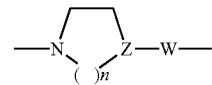

where n=1,2 or 3, Z=CH or N, and when Z=CH, W=NH or when Z=N, W is absent.

or

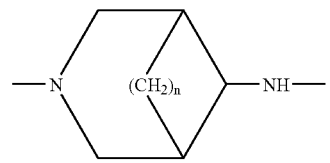

where n=0,1, or 2 such that this $R_7$ moiety is linked either to 2 core molecules of the Formula I to form a bis compound or the $R_7$ moiety has one of its link bonds linked to the core formula of Formula I and the second of its link bonds is linked to a phenyl carboxylic acid or ester moiety thereof, the phenyl carboxylic acid or ester being optionally substituted by the usual aromatic substituents, such as C1–C3 alkyl linear or branched, aralkyl such as benzyl, amino, alkylamino, alkanoylamino, ∝-aminoalkanoylamino, hydroxy, alkoxy, alkanoyloxy, ∝-aminoalkanoyloxy, or halogen atoms, such as fluoro, chloro, bromo.

- A=H, $C_{1-6}$ alkyl, glycosyl, aralkyl, $C_{1-6}$ alkanoyl or aminoalkanoyl. The aminoalkanoyl group may be an aminoacid residue derived from one of the one of the 20 naturally occurring amino acids or the optically active isomers thereof, or the racemic mixtures thereof. The amino residue is derived from alanine, arginine, asp aragine, asp artic acid, cysteine, glutamine, glutamic acid, glycine, histidine, isoleucine, leucine, lysine, methionine, phenylalanine, proline, serine, threonine, tryptophan, tyrosine or valine.
- A may also be $C_6H_{11}O_6$, $SO_3H$, or $PO_3H_2$,
- $R_{11}$=H, $C_{1-6}$ alkyl, $C_{3-6}$ cycloalkyl, or heterocyclic group,
- X=CH, C—F, C—Cl, C—CH$_3$, C—CF$_3$, C—OCH$_3$, C—OCHF$_2$, C—OCF$_3$, N or when X is equal to C it forms together with the nitrogen atom of the adjacent ring an optionally substituted 4-membered, 5-membered ring, 6-membered ring, 7-membered ring, containing carbon atoms and optionally one or more Y atoms representing one or more nitrogen, oxygen or sulfur atoms, such ring being further optionally substituted by a $C_{1-6}$ alkyl group; and their pharmaceutically acceptable salts, hydrates, polymorphs and pseudopolymorphs.

Where there are centres of asymmetry, the absolute stereochemistry can be either R- or S-configuration and any combination of configuration. Even racemic materials and diastereomers fulfil the structural generic descriptions.

Another object of the invention is to provide a process for preparing the novel efflux pump inhibitors of the formula I of the invention.

A further object of the invention is to provide pharmaceutical compositions comprising the compounds of the invention. A composition contains one or more compounds of formula I or salt, hydrate, polymorph or pseudopolymorph therefore. In addition to one or more compounds of formula I or a salt, hydrate, polymorph or pseudopolymorph thereof, a composition of this invention may also include another antibiotic or antimicrobial compound.

Yet another object of the invention relates to method of treatment of infections using the said compounds of the invention or compositions comprising them. Treatment comprises oral, parenteral administration and/or topical application of an effective amount of the compound of the invention or its compositions, whether single or in combination with an antibiotic or antimicrobial agent or two or more compounds of this invention.

Yet a further object of the invention includes a method of suppressing growth of a bacterium or a fungus expressing an efflux pump, comprising contacting said bacterium or fungus with an efflux pump inhibitor in the presence of a concentration of antibacterial or antifungal agent below the minimum inhibitory concentration (MIC) of said bacterium or fungus.

Yet a further object of the invention includes methods for treating the infections in humans and animals, caused by sensitive and resistant microbial strains using an antimicrobial agent and an efflux pump inhibitor in an amount sufficient to reduce efflux pump activity, wherein said efflux pump inhibitor increases the susceptibility of said microbe to said antimicrobial agent.

Yet a further object of the invention includes a method for prophylactic treatment of a human or animal, comprising administering to said human or animal at risk of a microbial infection an efflux pump inhibitor, wherein said efflux pump inhibitor decreases the pathogenicity of a microbe in said human or animal.

Yet a further object of the invention includes a method for prophylactic treatment of human or animal, comprising administering to said human or animal at risk of a microbial infection an antimicrobial agent and an efflux pump inhibitor, wherein said efflux pump inhibitor increases the susceptibility of a microbe to said antimicrobial agent.

Yet a further object of the invention includes a method of treatment using the efflux pump inhibitor compounds of the invention by administering, systemically or topically, optically pure compounds of the invention or stereochemically pure forms of the invention or their salts, hydrates, polymorphs, or pseudopolymorphs thereof to the affected human or animal, thereby avoiding the toxic effects associated with racemic mixtures of the compounds of the invention.

Yet a further object of the invention is to enhance the antimicrobial activity of an antimicrobial agent against a microbe by contacting the microbe with an antimicrobial agent and an efflux pump inhibitor.

DETAILED DESCRIPTION OF THE INVENTION

The present invention describes heterocyclic compounds of the formula I as novel microbial efflux pump inhibitors

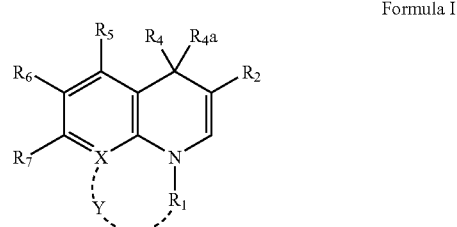

Formula I wherein, $R_1$=H, $C_{1-6}$ alkyl, $C_{3-6}$ cycloalkyl or optionally substituted aryl, aralkyl, arylaminoalkyl, aryloxyalkyl or arylS(O)$_t$alkyl, where t=0,1 or 2, or when X is C and the nitrogen atom to which $R_1$ is linked forms an optionally substituted 4-, 5-, 6- or 7-membered ring with X of the adjacent ring, the ring optionally containing one or more hetero atoms selected from nitrogen, oxygen or sulfur atoms, said heteroatom(s) represented by Y, prererably $R_1$ is —$CH_2CH_2$—, $CH_2Y$—, $CH_2CH_2CH_2$—, $CH_2CH_2Y$—, $CH_2CH_2CH_2CH_2$— and $CH_2CH_2CH_2Y$— where Y represents for NH, O, or S. If the ring is substituted, the substituent is $C_{1-6}$ alkyl group.

$R_2$=H, CHO, COOR$_3$, or CONHR$_{13}$, where $R_{13}$=H or the NHR$_{13}$ of CONHR$_{13}$ is the residue of one of the 20 naturally occurring amino acids: alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof, or combinations of these amino acids to give dipeptidyl or tripeptidyl or polypeptidyl residues.

$R_3$=H, $C_{1-6}$ alkyl, $C_{3-6}$ cycloalkyl, aryl, aralkyl, arylaminoalkyl, aryloxyalkyl, arylS(O)$_t$alkyl, where t=0,1 or 2, $(CH_2)_nCH(R_{14})OC(=O)R_{15}$, $(CH_2)_nCH(R_{14})C(=O)OR_{15}$ wherein n=0–6, $R_{14}$=H, or $CH_3$; and $R_{15}$=$C_2H_5$, or $C(CH_3)_3$ or $R_3$ is

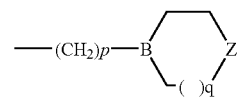

wherein B=CH or N, and when B=CH, Z=NH or NCH$_3$, and when B=N, Z=CH, O, NH, S or NCH$_3$; p=0–2; q=0–2, $R_4$=H, $R_{4a}$=H, or $R_4$ and $R_{4a}$ taken together are oxo (=O), or thio (=S).

$R_5$=H, $C_{1-5}$ alkyl, amino, alkylamino, or acylamino.

$R_6$=H, $C_{1-6}$ alkyl, halo such as F, Cl, Br, or I, amino, or hydroxy;

$R_7$=OH, halo such as F, Cl, Br, or I, or

NR$_9$R$_{10}$ wherein R$_9$ and R$_{10}$ are the same or different and represent H, $C_{1-6}$ alkyl or $(CH_2)_nOA$, or $R_9$ is H and $R_{10}$ is a 4-membered, 5-membered, 6-membered, or 7-membered carbocyclic, mono or bicyclic ring or mono or bicyclic heterocyclic ring linked to the nitrogen of $NR_9R_{10}$ through an atom of the heterocycle other than the heterocyclic atom or $R_9$ and $R_{10}$ taken together with the nitrogen atom to which they are attached form part of a heterocycle which heterocycle is monocyclic, bicyclic.

When $R_9$ is H and $R_{10}$ is a 4-membered ring, it is preferred that the ring is a ring such as 2-azetidinyl, when $R_{10}$ is a 5-membered ring, it is preferred that the ring is a ring such as 2- (or 3-) pyrrolidinyl, or 2- (or 3-) furyl, or 2-(or 3-) thienyl, or 2-(or 4-)imidazolyl, or oxazolyl or pyrazolyl, or thiazolyl, or when $R_{10}$ is a 6-membered ring, it is preferred that the ring is a ring such as 2-(or 3-, or 4-) piperidinyl, or 2-(or 3-) piperazinyl, or 2-(or 3-) morphoilnyl or 2-(or 4-)pyrimidinyl, and when $R_{10}$ is a 7-membered heterocycle it is preferred that the heterocycle is a heterocycle such as azepinyl, oxazinyl, or thiazinyl, or a bicyclic heterocycle such as tetrahydroisoquinolinyl, quinuclidinyl, or 3-azabicyclol-[3.1.0]hex-yl.

When $R_9$ and $R_{10}$ taken together with the nitrogen atom to which they are attached form part of a heterocycle which heterocycle is monocyclic, it is preferred that the heterocycle is such as azetidine, pyrrolidine, furan, thiophene, imidazole, oxazole, pyrazole, thiazole, piperidine, piperazine, pyrimidine, azepine, oxazine, thiazine, or bicyclic such as isoquinoline, quinuclidine, amino-3-azabicyclo[3.1.0]hexane.

The carbocycle and the heterocycle are optionally substituted at any position of the heterocyclic group with $COOR_3$ $CONHR_{13}$, OA, $C_{1-6}$ alkyl, aralkyl, trifluoroalkyl, substituted alkyl, or N $R_{16}R_{17}$.

Substituents of the alkyl group are selected from OA, $NR_{16}R_{17}$, or a halogen atom. $R_{16}$ and $R_{17}$ are the same or different and represent H or $C_{1-6}$ alkyl, or where one of $R_{16}$ and $R_{17}$ is hydrogen and the other of $R_{16}$ and $R_{17}$ is $C_3$–$C_6$ cycloalkyl, or substituted alkyl or R16 and $R_{17}$ taken together with the nitrogen atom form a heterocycle. When $R_{16}$ or $R_{17}$ is a substituted alkyl group, the substituent is selected from $NR_6R_{17}$, alkanoyl or aminoalkanoyl or $R_7$=NHOA, NHCOOR$_{11}$, $NH(CH_2)_nNR_9R_{10}$ or $R_7$=

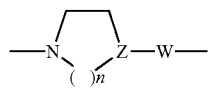

where n=1,2 or 3, Z=CH or N, and when Z=CH, W=NH or on when Z=N, W has no meaning.

or

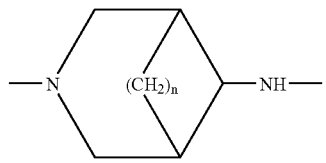

where n=0,1, or 2 such that this $R_7$ moiety is linked either to 2 core molecules of the Formula I to form a bis compound or the $R_7$ moiety has one of its link bonds linked to the core formula of Formula I and the second of its fink bonds is linked to a phenyl carboxylic acid or ester moiety thereof, optionally substituted by the usual aromatic substituents, such as C1–C3 alkyl linear or branched, aralkyl such as benzyl, amino, alkylamino, alkanoylamino, ∝-aminoalkanoylamino, hydroxy, alkoxy, alkanoyloxy, ∝-aminoalkanoyloxy, or halogen atoms, such as fluoro, chloro, bromo.

A=H, $C_{1-5}$ alkyl, glycosyl, aralkyl, $C_{1-6}$ alkanoyl or aminoalkanoyl. The aminoalkanoyl group may be an aminoacid residue derived from one of the one of the 20 naturally occurring amino acids or the optically active isomers thereof, or the racemic mixtures thereof. The amino residue is derived from alanine, arginine, asparagine, aspartic acid, cysteine, glutamine, glutamic acid, glycine, histidine, isoleucine, leucine, lysine, methionine, phenylalanine, proline, serine threonine, trytophan, tyrosine or valine.

A may also be $C_6H_{11}O_6$, $SO_3H$, or $PO_3H_2$, $R_{11}$=H, $C_{1-6}$ alkyl, $C_{3-6}$ cycloalkyl, or heterocyclic group such as a 4-membered ring, it is preferred that the ring is a ring such 2-azetidinyl, a 5-membered ring such as 2- (or 3-) pyrrolidinyl, or 2- (or 3-) furyl, or 2-(or 3-) thienyl, or 2-(or 4-) imidazolyl, or oxazolyl or pyrazolyl, or thiazolyl, or a 6-membered ring such as 2-(or 3-, or 4-) piperidinyl, or 2-(or 3-) piperazinyl, or 2-(or 3-) morpholinyl, or 2-(or 4-)pyrimidinyl, or a 7-membered heterocycle such as azepinyl, or oxazinyl, or thiazinyl, or a bicyclic heterocycle such as tetrahydroisoquinolinyl, or quinuclidinyl, or 3-azabicyclol-[3.1.0]hex-yl X=CH, C—F, C—Cl, C—CH$_3$, C—CF$_3$, C—OCH$_3$, C—OCHF$_2$, C—OCF$_3$, N or when X is equal to C it forms together with the nitrogen atom of the adjacent ring a 5-membered ring, 6-membered ring, 7-membered ring, optionally containing besides carbon atoms additional Y atoms representing one or more nitrogen, oxygen or sulfur atoms, such ring being further optionally substituted by a $C_{1-6}$ alkyl group; and their pharmaceutically acceptable salts, hydrates, polymorphs and pseudopolymorphs.

It is preferred that R4 and R4a are combined together to form an oxo group and R6 is hydrogen or fluorine.

Where there are centres of asymmetry, the absolute stereochemistry can be either R- or S-configuration and any combination of configuration. Even racemic materials and diastereomers fulfil the structural generic descriptions.

The term "alkyl" refers to a branched or unbranched $C_1$–$C_6$ aliphatic hydrocarbon group.

The term "aralkyl" refers to a $C_1$–$C_6$ alkyl group substituted with an aryl group which aryl group is defined below. One example of an aralkyl group is a benzyl group.

The terms "arylaminoalkyl", "aryloxyalkyl", and "arylS(O)$_t$alkyl refers to an aryl group as defined below that is bonded through an NH, oxygen, or sulfur or S(O)$_t$ to an alkyl group as defined above.

The term "aryl" refers to an aromatic group which has at least one ring having conjugated a electron system and includes both carbocyclic aryl (e.g., phenyl, naphthyl) and heterocyclic aryl groups (e.g. pyridyl, pyrimidyl, pyrazinyl, thienyl, furyl, pyrrolyl, pyrazolyl, imidazolyl, thiazolyl and oxazolyl). The aryl group is preferably 5 to 14 carbons, more preferably 5 to 10 carbons. Aryl moieties includes monocyclic, bicyclic, and tricyclic rings, where each ring has preferably five or six members and are 6π (or 6 pi)-annelated ring system or substituted 6π annelated ring systems composed of a mix of carbocyclic and heterocyclic units (e.g. benzo, pyrido, pyrimido, pyrazino, thieno, furano, pyrrolo, pyrazolo, imidazolo, thiazolo and oxazolo). The term "6π-annelated ring system" refers to a ring which has 6π electron and is considered arom tic. The ring may have 6 items in its backbone, such as pyridine, pyrimidine, benzene, or it may have less than 6 items in its backbone, such as pyrrole, pyrazole, furan, thiazole, oxazole or thiophene, aryl moiety may be optionally monosubstituted or disubstituted independently with lower linear or branched $C_1$–$C_6$ alkyl or hydroxyl, alkoxy, alkylthio, halogen, haloalkyl, mercapto, amino, mono linear or branched $C_1$–$C_3$alkylamino, di linear or branched $C_1$–$C_3$alkylamino, phenyl, substituted phenyl or optionally substituted phenylamino wherein the phenyl is substituted by usual aromatic substituents, such as $C_1$–$C_3$ alkyl linear or branched, aralkyl such as benzyl, amino, alkylamino, alkanoylamino, ∝-aminoalkanoylamino, hydroxy, alkoxy, alkanoyloxy, ∝-aminoalkanoyloxy, or halogen atoms, such as fluoro, chloro, or bromo. An example of a bicyclic ring system is for instance pyrazolopyridinyl optionally further substituted e.g. by a phenyl group or a substituted phenyl group.

"Alkylamino" is for example $NHCH_3$, $N(CH_3)_2$, $NHC_2H_5$, $N(C_2H_5)_2$, $NHC_3H_7$, $N(C_3H_7)_2$ and "Acylamino" is for example $NHCOCH_3$, $NHCOOC_2H_5$ or $NHC(=O)O(CH_3)_3$.

"Alkanoyl" is for example acetyl, propionyl, ethoxycarbonyl, t-butoxycarbonyl,

—$(CH_2)_nCHR_{14}$ $OC(=O)R_{15}$ is for example acetoxymethyl, pivaloxymethyl, pivaloyloxyethyl, pyrrolidinylethyl, piperidinylethyl, morpholinylethyl.

—$(CH_2)_nCHR_{14}$ $C(=O)OR_{15}$ is for example methoxycarbonylmethyl, ethoxycarbonylmethyl.

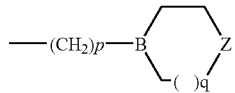

is for example pyrrolidinylethyl, piperidinylethyl, morpholinylethyl

The preferred acid addition salts are those of hydrochloride, hydrobromide, hydroiodide, sulphate, sulfonate, sulfamate, phosphate and salts of organic acids such as acetate, lactate, succinate, oxalate, maleate, fumarate, malate, tartrate, citrate, ascorbate, gluconate, benzoate, cinnamate, methane sulphonate and p-toluene sulphonate. Preferred alkali addition salts are lithium, sodium, potassium salts, and alkaline earth salts are magnesium, calcium salts, or ammonium, or organic amines such as diethanolamine, N-methylglucamine, guanidine or heterocyclic amines such as choline, piperidine, N-methyl-4-hydroxypiperidine, hydroxyethylpyrrolidine, hydroxyethylpiperidine, morpholine, hydroxyethylmorpholine, piperazine, N-methyl piperazine and the like or basic amino acids such as optically pure or racemic isomers of arginine, lysine, histidine, tryptophan and the like.

A number of compounds of this invention are disclosed in our PCT patent application number PCT/IN99/00016 and in our U.S. patent applications Ser. Nos. 09/566,875, 09/640,947, 09/850,669 and 60/286,291. The subject matter of PCT application PCT/IN99/00016 and of U.S. applications Ser. Nos. 09/566,875 09/566,875, 09/640,947, 09/850,669 and 60/286,291 are incorporated herein by reference.

A list of preferred compounds of the invention as novel microbial efflux pump inhibitors is provided below:

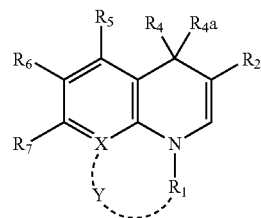

Formula I $R_1=C_2H_5$, $C_3H_5$, $CH(CH_3)CH_2CH_2SC_6H_5$, $C_6H_4(2\text{-}CF_3)$,
where (2-CF3) means that the CF3 group is attached at the 2 position, $C_6H_4(4\text{-}CF_3)$
where (4-CF3) means that the CF3 group is attached at the 2 position, $C_6H_4(4\text{-}F)$,
where (4-F) means that the F item is attached at the 4 position, and $C_6H_3(2,4\text{-}F_2)$)
where (2,4-F2) means that there are 2 fluorine atoms, one at the 2 position and the other at the 4 position.

X . . Y . . $N=C$—$CH_2CH_2CH(CH_3)$, $C$—$OCH_2CH(CH_3)$, $C$—$OCH_2CH_2CH(CH_3)$ $R2=COOH$, $COOC_2H_5$, $COOCH(CH_3)_2$, $COO(CH_2)_3CH_3$, $COOCH_2C_6H_5$, $COOCH_2COOC_2H_5$, $COO(CH_2)_2$-morpholino,

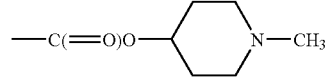

COphe-lys-Ome, where phe-lys-Ome is the methylester of the dipeptide from phenylalanine and lysine.

R4, R4a=O
R5=H, $CH_3$, or $NH_2$,
R6=H, or F
R7=F, Br, pyrrolidin-3-yl-amino, pyrrolidin-3-alkoxycarbonylamino, piperidin-4-yl-amino, pentaalkylpiperidin-4-yl-alkylamino, [1∝,5∝,6∝]-3-azabicyclo[3.1.0]hex-6-yl-amino, quinuclidinyl-3-yl-amino, 3-aminopyrrolidinyl, 5-aminopyrrolidinyl, aminopyrrolidinyl optionally further mono/poly substituted with $C_1$–$C_6$ alkyl, (mono/poly aminoalkanoyl)aminopyrrolidinyl; alkoxycarbonyl (mono/poly aminoalkanoyl) aminopyrrolidinyl; acetamidopyrrolidinyl optionally further mono/poly substituted with $C_1$–$C_6$ alkyl, hydroxypyrrolidinyl, piperidinyl optionally further mono/poly substituted with $C_1$–$C_6$ alkyl, or halogen; aminopiperidinyl optionally further mono/poly substituted with $C_1$–$C_6$ alkyl, alkoxycarbonyl; aminopiperidinyl optionally further mono/ poly substituted with $C_1$–$C_6$ alkyl, mono/dialkylaminopiperidinyl optionally further mono/poly substituted with $C_1$–$C_6$ alkyl, acetamidopiperidin-1-yl, 1-phenyl-4,5,6,7-tetrahydropyrazolo[4,3-c]pyridin-1-yl, mono/polyalkylpiperidinyl, carboxyamidopiperidinyl optionally further mono/ poly substituted with $C_1$–$C_6$ alkyl, hydroxypiperidinyl optionally further substituted with one or more $C_1$–$C_6$ alkyl or amino$C_1$–$C_6$alkyl, alkoxypiperidinyl; alkanoyloxypiperidinyl, ∝-aminoalkanoyloxypiperidinyl, alkoxycarbonyl-∝-aminoalkanoyloxypiperidinyl, alkoxycarbonyl-∝-aminoalkanoyaminopiperidinyl, hydroxypiperidinyl optionally further mono/poly substituted with $C_1$–$C_6$ alkyl, pyrrolidinyl-4-piperidinyl, 4-(piperidin-4-yl)-aminoalkylpiperidinyl, piperazinyl optionally further mono/poly substituted with $C_1$–$C_6$ alkyl, mono/polyalkylpiperazinyl; alkanoylpiperizine optionally further mono/poly substituted with $C_1$–$C_6$ alkyl, 4-(2-oxazolidinone-1-yl)-alkylpiperazine-1-yl; cyclopropylpiperazinyl; morpholino, mono/polyalkylmorpholino, 1,2,3,4-tetrahydroisoquinolin-2-yl, 6-amino-3-azabicyclo [3.1.0]hex-3-yl, 6-alkoxycarbonylamino-3-azabicyclo [3.1.0]hex-3-yl, 3-aralkyl-3-azabicyclo[3.1.0]hex-6-yl amino or 1-aryl,4,5,6,7-tetrahydropyrazolo[4,3-c]pyridin-1-yl Wherever stereoisomeric forms of the substituted heterocyclic moieties are possible, they are also here included.

X=C—H, C—OCH$_3$, C—F, N and when X is linked to N of the adjacent ring, it has the meanings as defmed above for X . . Y . . . N Compounds within the generic description as contained in formula I can be obtained by synthetic chemistry methods known to those skilled in the chemical arts. The methods described in our PCT application PCT/IN99/00016 and U.S. applications Ser. Nos. 09/566,875, 09/640,947, 09/850,669 and 60/286,291 are incorporated herein by reference.

The pharmaceutically acceptable acid addition salts of compounds I are prepared in a conventional manner by treating a solution or suspension of the free base I with about one chemical equivalent of a pharmaceutically acceptable acid. Conventional concentration and recrystallisation techniques are employed in isolating the salts. Illustrative of suitable acids are hydrochloric, hydrobromic, hydroiodic, sulphuric, sulfamic, sulfonic, phosphoric, acetic, lactic, succinic, oxalic, maleic, fumaric, malic, tartaric, citric, ascorbic, gluconic, benzoic, cinnamic, methanesulfonic and p-toluenesuffonic acid.

The pharmaceutically acceptable cationic salts of compounds I may be prepared by conventional methods from the corresponding acids e.g. by reaction with about one equimolar amount of a base. Examples of suitable cationic salts are those of alkali metals such as lithium, sodium or potassium, alkaline earth metals such as magnesium or calcium or ammonium or organic amines such diethanolamine, N-methylglucamine, guanidine or heterocyclic amines such as choline, piperidine, N-methyl-4-hydroxypiperidine, hydroxyethylpyrrolidine, hydroxyethylpiperidine, morpholine, hydroxyethylmorpholine, piperazine, N-methyl piperazine and the like or basic amino acids such as optically pure or racemic isomers of arginine, lysine, histidine, tryptophan and the like.

The hydrates, pseudopolymorphs and polymorphs are prepared by methods known in the art. Detailed descriptions of different methods to generate hydrates, solvates, pseudopolymorphs and polymorphs and to characterise them are described in chapters 5 and 6 of the book entitled "Polymorphism in Pharmaceutical Solids" edited by Harry G Brittain (Marcel Dekker Inc., New York), pp. 183–278, 1999.

The following is a list of compounds that inhibit the efflux pump of different organisms. The list of compounds and organisms is not inclusive. There are compounds on this list that will inhibit the efflux pump of other organisms.

Some Specific efflux pump inhibitor compounds of the invention are:

Some Preferred Compounds of the Invention Displaying Inhibition of the Efflux Pump of *Staphylococcus aureus* 1199 B (Nor A$^+$)

1. 1-Ethyl-6-fluoro-1,4-dihydro-7-(1',2',3',4'-tetrahydroisoquinolin-2-yl)-4-oxo-quinoline-3-carboxylic acid and its salts.
2. 1-Ethyl-6,8-fluoro-1,4-dihydro-7-(4'-acetoxypiperidin-1-yl)-4-oxo-quinoline-3-carboxylic acid and its salts.
3. 1-Ethyl-6,8-fluoro-1,4-dihydro-7-(4'-{2'-(2'-oxazolidin-1-yl) ethyl}piperizin-1-yl)-4-oxo-quinoline-3-carboxylic acid and its salts.
4. 1-Ethyl-6,8-difluoro-1,4-dihydro-7-{(1∝,5∝,6∝)-6-amino-3-azabicyclo[3.1.0]-hex-3-yl}-4-oxo-quinoline-3-carboxylic acid and its salts.
5. 5-Amino-1-ethyl-6,8-difluoro-1,4-dihydro-7-(3'-amino-5'-methyl pyrrolidin-1-yl)-4-oxo-quinoline-3-carboxylic acid and its salts.
6. 5-Amino-1-ethyl-6,8-difluoro-1,4-dihydro-7-(4'-aminopiperidin-1-yl)-4-oxo-quinoline-3-carboxylic acid and its salts.
7. 5-Amino-1-ethyl-6,8-difluoro-1,4-dihydro-7-{4'-(acetamido)piperidin-1-yl}-4-oxo-quinoline-3-carboxylic acid and its salts.
8. 5-Amino-1-ethyl-6,8-difluoro-1,4-dihydro-7-{(1∝,5∝,6∝)-6'-(t-butoxycarbonyl amino)-3-azabicyclo[3.1.0]-hex-3-yl}-4-oxo-quinoline-3-carboxylic acid and its salts.
9. 1-Cyclopropyl-6-fluoro-1,4-dihydro-7-(3'-acetamido-5'-methylpyrrolidin-1-yl)-4-oxo-quinoline-3-carboxylic acid and its salts.
10. 1-Cyclopropyl-6-fluoro-1,4-dihydro-7-(3'-amino-5'-methylpyrrolidin-1-yl)-4-oxo-quinoline-3-carboxylic acid and its salts.
11. 1-Cyclopropyl-6-fluoro-1,4-dihydro-7-(4'-acetoxypiperidin-1-yl)-4-oxo-quinoline-3-carboxylic acid and its salts.
12. 1-Cyclopropyl-6-fluoro-1,4-dihydro-7-{4'-(dimethylamino)piperidin-1-yl)-4-oxo-quinoline-3-carboxylic acid and its salts.
13. 1-Cyclopropyl-6-fluoro-1,4-dihydro-7-(3',5'-dimethylpiperidin-1-yl)-4-oxo-quinoline-3-carboxylic acid and its salts.
14. 1-Cyclopropyl-6-fluoro-1,4-dihydro-7-(4'-hydroxy-3',5'-dimethylpiperidin-1-yl)-4-oxo-quinoline-3-carboxylic acid and its salts.
15. 1-Cyclopropyl-6-fluoro-1,4-dihydro-7-(3',4',5'-trimethylpiperazin-1-yl)-4-oxo-quinoline-3-carboxylic acid and its salts.
16. 1-Cyclopropyl-6-fluoro-1,4-dihydro-7-(3',5'-dimethyl-4'-ethylpiperazin-1-yl)-4-oxo-quinoline-3-carboxylic acid and its salts.
17. 1-Cyclopropyl-6-fluoro-1,4-dihydro-5-methyl-7-(4'-ethoxypiperidin-1-yl)-4-oxo-quinoline-3-carboxylic acid and its salts.
18. 1-Cyclopropyl-6-fluoro-1,4-dihydro-5-methyl-7-(3',3'-dimethylpiperazin-1-yl)-4-oxo-quinoline-3-carboxylic acid and its salts.
19. 1-Cyclopropyl-6-fluoro-8-methoxy-1,4-dihydro-7-{4'-(dimethylamino)-3'-methyl piperidin-1-yl}-4-oxo-quinoline-3-carboxylic acid and its salts.
20. 1-Cyclopropyl-6-fluoro-8-methoxy-1,4-dihydro-7-(4'-hydroxy-3'-isobutylpiperidin-1-yl)-4-oxo-quinoline-3-carboxylic acid and its salts.
21. 1-Cyclopropyl-6-fluoro-8-methoxy-1,4-dihydro-7-(4'-hydroxy-3',3'-dimethylpiperidin-1-yl)-4-oxo-quinoline-3-carboxylic acid and its salts.
22. 1-Cyclopropyl-6-fluoro-8-methoxy-1,4-dihydro-7-(4'-hydroxy-3,3'-dimethylpiperidin-1-yl)-4-oxo-quinoline-3-carboxylic acid and its salts.
23. 1-Cyclopropyl-6-fluoro-8-methoxy-1,4-dihydro-7-(3'-methylpiperazin-1-yl)-4-oxo-quinoline-3-carboxylic acid and its salts.
24. 5-Amino-1-cyclopropyl-6-fluoro-8-methoxy-1,4-dihydro-7-(cis-4'-amino-3',5'-dimethylpiperidin-1yl)-4-oxo-quinoline-3-carboxylic acid and its salts.

25. 1-Cyclopropyl-6,8-difluoro-5-methyl-1,4-dihydro-7-(4'-hydroxy-3'-aminomethylpiperidin-1-yl)-4-oxo-quinoline-3-carboxylic acid and its salts.
26. 5-Amino-1-cyclopropyl-6,8-difluoro-1,4-dihydro-7-(5'amino-2'-methyl-pyrrolidin-1-yl)-4-oxo-quinoline-3-carboxylic acid and its salts.
27. 5-Amino-1-cyclopropyl-6,8-difluoro-1,4-dihydro-7-{3'-(L-Ala-L-Ala)aminopyrrolidin-1-yl}-4-oxo-quinoline-3-carboxylic acid and its salts.
28. 5-Amino-1-cyclopropyl-6,8-difluoro-1,4-dihydro-7-{4'-(di-n-butylamino)piperidin-1-yl)-4-oxo-quinoline-3-carboxylic acid and its salts.
29. 5-Amino-1-cyclopropyl-6,8-difluoro-1,4-dihydro-7-{4'-(t-butoxycarbonyl-L-Ala-L-Ala)aminopiperidin-1-yl}-4-oxo-quinoline-3-carboxylic acid and its salts.
30. 5-Amino-1-cyclopropyl-6,8-difluoro-1,4-dihydro-7-(4'-propionoxypiperidin-1-yl)-4-oxo-quinoline-3-carboxylic acid and its salts.
31. 5-Amino-1-cyclopropyl-6,8-difluoro-1,4-dihydro-7-(4'-hydroxy-3',3'-dimethyl-piperidin-1-yl)-4-oxo-quinoline-3-carboxylic acid and its salts.
32. 5-Amino-1-cyclopropyl-6,8-difluoro-1,4-dihydro-7-{4'-(1-pyrrolidinyl)piperidin-1-yl)-4-oxo-quinoline-3-carboxylic acid and its salts.
33. 5-Amino-1-cyclopropyl-6,8-difluoro-1,4-dihydro-7-{4'-[(piperidin-4-yl)aminomethyl]-piperidin-1-yl}-4-oxo-quinoline-3-carboxylic acid and its salts.
34. 5-Amino-1-cyclopropyl-6,8-difluoro-1,4-dihydro-7-{(1,2',2',6',6'-pentamethylpiperidin-4-yl)methylamino}-4-oxo-quinoline-3-carboxylic acid and its salts.
35. 5-Amino-1-cyclopropyl-6,8-difluoro-1,4-dihydro-7-(3', 5'-dimethylmorpholin-1-yl)-4-oxo-quinoline-3-carboxylic acid and its salts.
36. 5-Amino-1-cyclopropyl-6,8-difluoro-1,4-dihydro-7-(4'-cyclopropylpiperazin-1-yl)-4-oxo-quinoline-3-carboxylic acid and its salts.
37. 5-Amino-1-cyclopropyl-6,8-difluoro-1,4-dihydro-7-(3',5'-dimethyl-4-pivaloylpiperazin-1-yl)-4-oxo-quinoline-3-carboxylic acid and its salts.
38. Ethyl 6,8-difluoro-7-(4-hydroxypiperidin-1-yl)-1-(1-phenylthio-3(S)-but-3-yl)-1,4-dihydro-4-oxo-quinoline-3-carboxylate
39. 1-(2'-Trifluoromethylphenyl)-6-fluoro-1,4-dihydro-7-(3',3',4'-trimethylpiperazin-1-yl)-4-oxo-quinoline-3-carboxylic acid and its salts.
40. 5-Amino-1-(2'-trifluoromethylphenyl)-6,8-difluoro-1,4-dihydro-7-(morpholin-1-yl)-4-oxo-quinoline-3-carboxylic acid and its salts.
41. 5-Amino-1-(2'-trifluoromethylphenyl)-6,8-difluoro-1,4-dihydro-7-(3',5'-dimethylmorpholin-1-yl)-4-oxo-quinoline-3-carboxylic acid and its salts.
42. 5-Amino-1-(2'-trifluoromethylphenyl)-6,8-difluoro-1,4-dihydro-7-(3',5'-dimethylpiperazinyl-1-yl)-4-oxo-quinoline-3-carboxylic acid and its salts.
43. 5-Amino-1-(4'-trifluoromethylphenyl)-6,8-difluoro-1,4-dihydro-7-(3'-aminopyrrolidin-1-yl)-4-oxo-quinoline-3-carboxylic acid and its salts.
44. 1-(4'-Fluorophenyl)-6-fluoro-1,4-dihydro-7-{4'-ethylamino)piperidin-1-yl)-4-oxo-quinoline-3-carboxylic acid and its salts.
45. 1-(2',4'-Difluorophenyl)-6-fluoro-1,4-dihydro-7-(3', 5'-dimethylpiperidin-1-yl)-4-oxo-quinoline-3-carboxylic acid and its salts.
46. 5-Amino-1-(2',4'-difluorophenyl)-6,8-difluoro-1,4-dihydro-7-(3'-hydroxy-5'-methylpyrrolidin-1-yl)-4-oxo-quinoline-3-carboxylic acid and its salts.
47. 5-Amino-1-(2',4'-difluorophenyl)-6,8-difluoro-1,4-dihydro-7-(3',3'-dimethylpiperazinyl-1-yl)-4-oxo-quinoline-3-carboxylic acid and its salts.
48. 1-Cyclopropyl-6-fluoro-1,4-dihydro-7-{(3'-aminoethoxycarbonyl)pyrrolidin-3-yl}-4-oxo-1,8-naphthyridine-3-carboxylic acid and its salts.
49. 1-Cyclopropyl-6-fluoro-1,4-dihydro-7-(pyrrolidin-3-yl-amino)-4-oxo-naphthyridine-3-carboxylic acid and its salts.
50. 1-(2',4'-Difluorophenyl)-6-fluoro-1,4-dihydro-7-(piperidin-4-yl-amino)-4-oxo-1,8-naphthyridine-3-carboxylic acid and its salts.
51. Ethyl-1-(2',4'-difluorophenyl)-6-fluoro-1,4-dihydro-7-{[1∝,5∝,6∝]-3-N-benzyl-3-azabicyclo[3.1.0]hex-6-yl-amino}-4-oxo-1,8-naphthyridine-3-carboxylate and its salts
52. 1-(2,4-difluorophenyl)-6-fluoro-7-(1-phenyl-4,5,6,7-tetrahydropyrazolo[4,3-c]pyridin-1-yl-1,4-dihydro-4-oxo-1,8-naphthyridine-3-carboxylic acid and its salts.
53. (S)-(–)-9-Fluoro-6,7-dihydro-8-(4'-carboxamidopiperidin-1-yl)-5-methyl-1-oxo-1H,5H-benzo[i,j]quinolizine-2-carboxylic acid and its salts.
54. (R)-(+)-9-Fluoro-6,7-dihydro-8-(4'-hydroxypiperidin-1-yl)-5-methyl-1-oxo-1H,5H-benzo[i,j]quinolizine-2-carboxylic acid L-arginine salt
55. (S)-(–)-9-Fluoro-6,7-dihydro-8-(4'-hydroxy-3',3'-dimethylpiperidin-1-yl)-5-methyl-1-oxo-1H,5H-benzo[i,j]quinolizine-2-carboxylic acid and its salts.
56. (S)-(–)-N-methylpiperidin-1-yl-9-fluoro-6,7-dihydro-8-(4'-hydroxypiperidin-1-yl)-5-methyl-1-oxo-1H,5H-benzo[i,j]quinolizine-2-carboxylate.
57. (S)-(–)-Morpholinoethyl-9-fluoro-6,7-dihydro-8-(4'-hydroxypiperidin-1-yl)-5-methyl-1-oxo-1H,5H-benzo[i,j]quinolizine-2-carboxylate and its salts
58. Ethoxycarbonylmethyl (R)-(+)-9-fluoro-6,7-dihydro-8-(4'-hydroxypiperidin-1-yl)-5-methyl-oxo-1H,5H-benzo[i,j]quinolizine-2-carboxylate Some Preferred Bis Compounds of the Invention Displaying Inhibition of the Efflux Pump of *Staphylococcus aureus* 1199 B (Nor A$^+$)

1. N-1-{7-(1-cyclopropyl-6-fluoro-1,4-dihydro-4-oxo-quinoline-3-carboxylic acid)}-N-3-amino-{7-(1-(2,4-difluorophenyl)-6-fluoro-1,4-dihydro-4-oxo-1,8-naphthyridine-3-carboxylic acid)}-pyrrolidine.
2. N-1-{7-(1-cyclopropyl)-6-fluoro-1,4-dihydro-4-oxo-1,8-naphthyridine-3-carboxylic acid)}-N-3-amino-{7-(1-cyclopropyl)-6-fluoro-1,4-dihydro-4-oxo-1,8-naphthyridine-3-carboxylic acid)}-pyrrolidine
3. N-1-{7-(1-cyclopropyl)-6-fluoro-1,4-dihydro-4-oxo-1,8-naphthyridine-3-carboxylic acid)}-N-3-amino-{7-(1-cyclopropyl-6,8-difluoro-5-amino-1,4-dihydro-4-oxo-quinoline-3-carboxylic acid)}-pyrrolidine
4. N-1-{7-(1-cyclopropyl)-6-fluoro-1,4-dihydro-4-oxo-1,8-naphthyridine-3-carboxylic acid)}-N-4-{7-(1-cyclopropyl-6,8-difluoro-5-amino-1,4-dihydro-4-oxo-quinoline-3-carboxylic acid)}-piperazine
5. N-1-{7-(1-cyclopropyl-6-fluoro-5-methyl-1,4-dihydro-4-oxo-quinolone-3-carboxylic acid)}-N-3-amino-{7-(1-(2,4-difluorophenyl)-6-fluoro-1,4-dihydro-4-oxo-1,8-naphthyridine-3-carboxylic acid)}-pyrrolidine
6. N-1-{7-(1-cyclopropyl-6-fluoro-5-methyl-1,4-dihydro-4-oxo-quinolone-3-carboxylic acid)}-N-4-amino{7-(1-cyclopropyl-6,8-difluoro-5-amino-1,4-dihydro-4-oxo-quinoline-3-carboxylic acid)}-piperidine
7. N-1-{7-(1-cyclopropyl-6-fluoro-5-methyl-1,4-dihydro-4-oxo-quinolone-3-carboxylic acid)}-N-3- amino{7-(1-cyclopropyl-6,8-difluoro-5-amino-1,4-dihydro-4-oxo-quinoline-3-carboxylic acid)}-pyrrolidine
8. N-1-{7-(1-(2,4-difluorophenyl)-6-fluoro-1,4-dihydro-4-oxo-1,8-naphthyridine-3-carboxylic acid)}-N-4-{7-(1-cyclopropyl-6-fluoro-1,4-dihydro-4-oxo-quinoline-3-carboxylic acid)}-piperazine
9. N-3-azabycyclo{7-(1-(2,4-difluorophenyl)-6-fluoro-1,4-dihydro-4-oxo-1,8-naphthyridine-3-carboxylic acid)}-[1∝,5∝,6∝]-N-6-amino-{7-1-(2,4-difluorophenyl)-6-fluoro-1,4-dihydro-4-oxo-1,8-naphthyridine-3-carboxylic acid)}-3.1.0]hexane
10. N-1-{7-(1-cyclopropyl-6,8-difluoro-5-amino-1,4-dihydro-4-oxo-quinolone-3-carboxylic acid)}-N-4-amino-{ethyl 2,3,6-trifluorophenyl-4-carboxylate}-piperidine Some Preferred Compounds of the Invention Displaying Inhibition of the Efflux Pumps of *Pseudomonas aeruainosa* 23587

1. 1-Cyclopropyl-6-fluoro-1,4-dihydro-5-methyl-7-(4'-methoxypiperidin-1-yl)-4-oxo-quinoline-3-carboxylic acid and its salts.
2. 7-Bromo-1-cyclopropyl-6-fluoro-5-methyl-1,4-dihydro-4-oxo-quinoline-3-carboxylic acid and its salts.
3. 1-Cyclopropyl-6-fluoro-8-methoxy-1,4-dihydro-7-(4'-amino-3'-methylpiperidin-1-yl)-4-oxo-quinoline-3-carboxylic acid and its salts.
4. 5-Amino-1-cyclopropyl-6-fluoro-8-methoxy-1,4-dihydro-7-(4'-amino-3'-methylpiperidin-1-yl)-4-oxo-quinoline-3-carboxylic acid and its salts.
5. 5-Amino-1-cyclopropyl-6-fluoro-8-methoxy-1,4-dihydro-7-{3,3-dimethyl-4'-ethylaminopiperidin-1-yl}-4-oxo-quinoline-3-carboxylic acid and its salts.
6. 1-Cyclopropyl-6-fluoro-8-methoxy-1,4-dihydro-7-(4'-amino-3'-3'-dimethylpiperidin-1-yl)-4-oxo-quinoline-3-carboxylic acid and its salts.
7. 1-Cyclopropyl-6-fluoro-8-methoxy-1,4-dihydro-7–14'-(dimethylamino)piperidin-1-yl]-4-oxo-quinoline-3-carboxylic acid and its salts
8. 1-Cyclopropyl-6-fluoro-8-methoxy-1,4-dihydro-7-(4'-hydroxy-4'-methylpiperidin-1-yl)-4-oxo-quinoline-3-carboxylic acid and its salts.
9. 1-Cyclopropyl-6-fluoro-8-methoxy-1,4-dihydro-7-(3',3'-dimethyl-4'-hydroxypiperidin-1-yl)-4-oxo-quinoline-3-carboxylic acid and its salts.
10. 1-Cyclopropyl-6,8-difluoro-5-methyl-1,4-dihydro-7-(3'-aminomethyl-4'-hydroxypiperidin-1-yl)-4-oxo-quinoline-3-carboxylic acid and its salts.
11. 5-Amino-1-cyclopropyl-6,8-difluoro-1,4-dihydro-7-(3'-aminomethyl-4'-hydroxypiperidin-1-yl)-4-oxo-quinoline-3-carboxylic acid and its salts.
12. 1-Ethyl-6,8-difluoro-1,4-dihydro-7-(3'-5'-dimethylpiperazin-1-yl)-4-oxo-quinoline-3-carboxylic acid and its salts.
13. 1-Cyclopropyl-6-fluoro-1,4-dihydro-7-(4'-ethyl-3'-methylpiperazin-1-yl)-4-oxo-quinoline-3-carboxylic acid and its salts.
14. 1-Cyclopropyl-6-fluoro-1,4-dihydro-7-(3'-5'-dimethyl-4'-ethylpiperazin-1-yl)-4-oxo-quinoline-3-carboxylic acid and its salts.
15. 1-Ethyl-6,8-difluoro-1,4-dihydro-7-{(1∝,5∝,6∝)-6'-amino-3'-azabicyclo[3.1.0]hex-3'-yl}-4-oxo-quinoline-3-carboxylic acid and its salts.
16. 5-Amino-1-(2',4'-difluorophenyl)-6,8-difluoro-1,4-dihydro-7-(3'-aminopyrrolidin-1-yl)-4-oxo-quinoline-3-carboxylic acid and its salts.
17. 5-Amino-1-cyclopropyl-6,8-difluoro-1,4-dihydro-7-{(3'-amimoethoxycarbonylpyrrolidin-3-yl}-4-oxo-quinoline-3-carboxylic acid and its salts.
18. 8-Cyclopropyl-6-fluoro-1,4-dihydro-7-(pyrrolidin-3'-ylamino)-4-oxo-naphthyridine-3-carboxylic acid and its salts.
19. 1-(2',4'-Difluorophenyl)-6-fluoro-1,4-dihydro-7-(piperidin-4'-ylamino)-4-oxo-naphthyridine-3-carboxylic acid and its salts.
20. 1-Cyclopropyl-6-fluoro-1,4-dihydro-7-(4'-amino-3'-ethylpiperidin-1-yl)-4-oxo-naphthyridine-3-carboxylic acid and its salts.
21. (S)-(−)-9-Fluoro-6,7-dihydro-8-(4'-hydroxypiperidin-1-yl)-5-methyl-1-oxo-1H,5H-benzo[i,j]quinolizine-2-carboxylic acid 0.2 hydrate.
22. (S)-(−)-9-Fluoro-6,7-dihydro-8-(4'-hydroxypiperidin-1-yl)-5-methyl-1-oxo-1H,5H-benzo[i,j]quinolizine-2-carboxylic acid. choline salt.
23. (S)-(−)-9-Fluoro-6,7-dihydro-8-(4'-hydroxypiperidin-1-yl)-5-methyl-1-oxo-1H,5H-benzo[i,j]quinolizine-2-carboxylic acid. 1-Hydroxyethylpyrrolidine salt.
24. (S)-(−)-9-Fluoro-6,7-dihydro-8-(4'-hydroxypiperidin-1-yl)-5-methyl-1-oxo-1H,5H-benzo[i,j]quinolizine-2-carboxylic acid. Diethanolamine salt.
25. (S)-(−)-9-Fluoro-6,7-dihydro-8-(4'-hydroxypiperidin-1-yl)-5-methyl-1-oxo-1H,5H-benzo[i,j]quinolizine-2-carboxylate. L-histidine salt.
26. (RS)-(±)-9-Fluoro-6,7-dihydro-8-{4'-(D-phenylalanyloxy)piperidin-1-yl}-5-methyl-1-oxo-1H,5H-benzo[i,j]quinolizine-2-carboxylic acid hydrochloride.
27. (RS)-(±)-9-Fluoro-6,7-dihydro-8-{4'-(L-α-aspartyloxy)piperidin-1-yl}-5-methyl-1-oxo-1H,5H-benzo[i,j] quinolizine-2-carboxylic acid hydrochloride.
28. (RS)-(±)-9-Fluoro-6,7-dihydro-8-{4'-(L-leucyloxy)piperidin-1-yl}-5-methyl-1-oxo-1H,5H-benzo[i,j] quinolizine-2-carboxylic acid dihydrochloride.
29. (S)-(−)-9-Fluoro-6,7-dihydro-8-{4'-(D-leucyloxy)piperidin-1-yl}-5-methyl-1-oxo-1H,5H-benzo[i,j]quinolizine-2-carboxylic acid hyrdochloride.
30. (S)-(−)-9-Fluoro-6,7-dihydro-8-{4'-(L-alanyloxy)piperidin-1-yl}-5-methyl-1-oxo-1H,5H-benzo[i,j]quinolizine-2-carboxylic acid hydrochloride.
31. (S)-(−)-Morpholinoethyl-9-fluoro-6,7-dihydro-8-(4'-hydroxypiperidin-1-yl)-5-methyl-1-oxo-1H,5H-benzo[i,j]quinolizine-2-carboxylate and its salts.
32. (R)-(+)-8,9-difluoro-6,7-dihydro-5-methyl-1-oxo-1H,5H-benzo[i,j]quinolizine-2-[S-phenylalanyl-S-lysine methyl ester]carboxamide.
33. (RS)-(±)-9-Fluoro-6,7-dihydro-8-(trans-4'-hydroxy-3'-methylpiperidin-1-yl)-5-methyl-1-oxo-1H,5H-benzo[i,j]quinolizine-2-carboxylic acid and its salts
34. (RS)-(±)-9-Fluoro-6,7-dihydro-8-(cis-4'-hydroxy-3'-methylpiperidin-1-yl)-5-methyl-1-oxo-1H,5H-benzo[i,j]quinolizine-2-carboxylic acid and its salts.
35. (S)-(−)-9-Fluoro-6,7-dihydro-8-(trans-4'-hydroxy-3'-methylpiperidin-1-yl)-5-methyl-1-oxo-1H,5H-benzo[i,j]quinolizine-2-carboxylic acid and its salts.
36. 7H-Pyrido[1,2,3-de]-1,4-benzoxazine-9-fluoro-2,3-dihydro-3-methyl-10-(4'-hydroxy-3'-ethylpiperidin-1'-yl)-7-oxo-6-carboxylic acid and its salts.
37. 10-Fluoro-11-[(1∝,5∝,6∝)-6-amino-3-azabicyclo[3.1.0]hex-3-yl]-3,4-dihydro-4(S)-methly-8-oxo-2H,8H-pyrido[1,2,3-ef]-1,5-benzoxazepine-7-carboxylic acid. hydrochloride.

Some Preferred Compounds of the Invention Displaying Inhibition of the Efflux Pumps of *Escherischia coli* 2051

1. 7-Bromo-1-cyclopropyl-6-fluoro-5-methyl-1,4-dihydro-4-oxo-quinoline-3-carboxylic acid and its salts.
2. 1-Cyclopropyl-6-fluoro-8-methoxy-1,4-dihydro-7-(4'-amino-3'-methylpiperidin-1-yl)-4-oxo-quinoline-3-carboxylic acid and its salts.
3. 1-Cyclopropyl-6-fluoro-8-methoxy-1,4-dihydro-7-(4'-amino-3'-3'-dimethylpiperidin-1-yl)-4-oxo-quinoline-3-carboxylic acid and its salts.
4. S-(−)-9-Fluoro-6,7-dihydro-8-(4'-hydroxypiperidin-1-yl)-5-methyl-1-oxo-1H,5H-benzo[i,j]quinolizine-2-carboxylic acid 0.2 hydrate.
5. S-(−)-9-Fluoro-6,7-dihydro-8-(4'-hydroxypiperidin-1-yl)-5-methyl-1-oxo-1H,5H-benzo[i,j]quinolizine-2-carboxylic acid. Choline salt.
6. S-(−)-9-Fluoro-6,7-dihydro-8-(4'-hydroxypiperidin-1-yl)-5-methyl-1-oxo-1H,5H-benzo[i,j]quinolizine-2-carboxylic acid. 1-Hydroxyethylpyrrolidine salt.
7. S-(−)-9-Fluoro-6,7-dihydro-8-(4'-hydroxypiperidin-1-yl)-5-methyl-1-oxo-1H,5H-benzo[i,j]quinolizine-2-carboxylic acid. Diethanolamine salt.
8. (S)-(−)-9-Fluoro-6,7-dihydro-8-{4'-(D-leucyloxy)piperidin-1-yl}-5-methyl-1-oxo-1H,5H-benzo[i,j]quinolizine-2-carboxylic acid hydrochloride.
9. (S)-(−)-Morpholinoethyl-9-fluoro-6,7-dihydro-8-(4'-hydroxypiperidin-1-yl)-5-methyl-1-oxo-1H,5H-benzo[i,j]quinolizine-2-carboxylate and its salts
10. (R)-(+)-8,9-difluoro-6,7-dihydro-5-methyl-1-oxo-1H,5H-benzo[i,j]quinolizine-2-[S-phenylalanyl-S-lysine methyl ester]carboxamide.
11. S-(−)-9-Fluoro-6,7-dihydro-8-(trans-4'-hydroxy-3'-methylpiperidin-1-yl}-5-methyl-1-oxo-1H,5H-benzo[i,j]quinolizine-2-carboxylic acid and its salts.
12. 10-Fluoro-11-[(1α,5α,6α)-6-amino-3-azabicyclo[3.1.0]hex-3yl]-3,4-dihydro-4(S)-methyl-8-oxo-2H,8H-pyrido[1,2,3-ef]-1,5-benzoxazipin-5-yl-7-carboxylic acid hydrochloride.

Some Preferred Compounds of the Invention Displaying Inhibition of the Mef Efflux Pump of *Streptococcus pneumoniae* 3514 and *Streptococcus pyogenes* 26-00

1. 1-Cyclopropyl-6-fluoro-8-methoxy-1,4-dihydro-7-(4'-amino-3'-methylpiperidin-1-yl)-4-oxo-quinoline-3-carboxylic acid and its salts.
2. 5-Amino-1-cyclopropyl-6-fluoro-8-methoxy-1,4-dihydro-7-{4'-(methylamino)-3',3'-dimethylpiperidin-1-yl}-4-oxo-quinoline-3-carboxylic acid and its salts.
3. i-Propyl 1-cyclopropyl-6-fluoro-8-methoxy-1,4-dihydro-7-(4'-amino-3',3'-dimethylpiperidin-1-yl}-4-oxo-quinoline-3-carboxylate and its salts.
4. n-Butyl 1-cyclopropyl-6-fluoro-8-methoxy-1,4-dihydro-7-(4'-amino-3',3'-dimethylpiperidin-1-yl}-4-oxo-quinoline-3-carboxylate and its salts.
5. Ethoxycarbonylmethyl 1-cyclopropyl-6-fluoro-8-methoxy-1,4-dihydro-7-(4'-amino-3',3'-dimethylpiperidin-1-yl)-4-oxo-quinoline-3-carboxylate and its salts.
6. Benzyl 1-cyclopropyl-6-fluoro-8-methoxy-1,4-dihydro-7-{4'-(t-butoxycarbonylamino)-3',3'-dimethylpiperidin-1-yl)-4-oxo-quinoline-3-carboxylate and its salts.
7. 1-Cyclopropyl-6-fluoro-8-methoxy-1,4-dihydro-7-{4'-N-(t-butoxycarbonyl-L-alanyl)amino-3',3'-dimethylpiperidin-1-yl}-4-oxo-quinoline-3-carboxylic acid hydrochloride.
8. 1-Cyclopropyl-6-fluoro-8-methoxy-1,4-dihydro-7-(4'-L-alanylamino-3',3'-dimethylpiperidin-1-yl}-4-oxo-quinoline-3-carboxylic acid hydrochloride.
9. 1-Cyclopropyl-6-fluoro-8-methoxy-1,4-dihydro-7-{3',3'-dimethyl-4'-(t-butoxy-carbonylvalinylamino)piperidin-1yl}-4-oxo-quinoline-3-carboxylic acid and its salts.
10. 1-Cyclopropyl-6-fluoro-8-methoxy-1,4-dihydro-7-(3',3'-dimethyl-4'-(L)-valylaminopiperidin-1-yl}-4-oxo-quinoline-3-carboxylic acid hydrochloride.
11. 1-Cyclopropyl-6-fluoro-8-methoxy-1,4-dihydro-7-{4'-(L)-aspartylamino-3',3'-dimethylpiperidin-1-yl}-4-oxo-quinoline-3-carboxylic acid hydrochloride
12. 1-Ethyl-6,8-difluoro-1,4-dihydro-7-(4'-ethylaminopiperidin-1'-yl)-4-oxo-quinoline-3-carboxylic acid and its salts.
13. 5-Amino-1-cyclopropyl-6,8-difluoro-1,4-dihydro-7-(4'-amino-3'-methylpiperidin -1-yl)-4-oxo-quinoline-3-carboxylic acid and its salts.
14. 5-Amino-5-cyclopropyl-6,8-difluoro-1,4-dihydro-7-(quinuclidinyl-3-yl-amino)-4-oxo-quinoline-3-carboxylic acid and its salts.
15. 5-Amino-1-cyclopropyl-6,8-difluoro-1,4-dihydro-7-{(1α,5α,6α)-6-amino-N-benzyl-3-azabicyclo[3.1.0]hex-6-yl}-4-oxo-quinoline-3-carboxylic acid and its salts.
16. 1-(3'-Fluorophenyl)-6-fluoro-1,4-dihydro-7-(4'-methylpiperazin-1'-yl)-4-oxo-quinoline-3-carboxylic acid and its salts.
17. 1-(2,4-Difluorophenyl)-6-fluoro-1,4-dihydro-7-(4'-ethylaminopiperidin-1'-yl)-4-oxo-quinoline-3-carboxylic acid and its salts.
18. 1-(2',4'-Difluorophenyl)-6-fluoro-5-methyl-1,4-dihydro-7-(4'-aminopiperidin-1'-yl)-4-oxo-quinoline-3-carboxylic acid and its salts.
19. 1-(2',4'-Difluorophenyl)-6-fluoro-5-methyl-1,4-dihydro-7-(4'-methylaminopiperidin-1'-yl)-4-oxo-quinoline-3-carboxylic acid and its salts.
20. 1-Cyclopropyl-6-fluoro-1,4-dihydro-7-(3'-aminopyrrodin-1'-yl)-4-oxo-1,8-naphthyridine-3-carboxylic acid and its salts.
21. 1-Cyclopropyl-6-fluoro-1,4-dyhydro-7-{(1α,5α,6α)-6-amino-N-benzyl-3-azabicyclo[3.1.0]hex-6-yl}-4-oxo-1,8-naphythyridine-3-carboxylic acid and its salts.
22. 1-(2,4-Difluorophenyl)-6-fluoro-1,4-dihydro-7-(3'-aminopyrrolidin-1'-yl)-4-oxo-1,8-naphthyridine-3-carboxylic acid and its salts.
23. 1-(2,4-Difluorophenyl)-6-fluoro-1,4-dihydro-7-{(1α,5α,6α)-6-amino-N-benzyl-3-azabicyclo[3.1.0]hex-6-yl}-4-oxo-1,8-naphthyridine-3-carboxylic acid and its salts.
24. 1-(2,4-Difluorophenyl)-6-fluoro-1,4-dihydro-7-(3',3'-dimethyl-4'-hydroxypiperdin-1'-yl)-4-oxo-1,8-naphthyridine-3-carboxylic acid and its salts.
25. (RS)-(±)-9-Fluoro-6,7-dihydro-8-{4'-(L-α-aspartyloxy)piperidin-1-yl}-5-methyl-1-oxo-1H,5H-benzo[i,j]quinolizine-2-carboxylic acid hydrochloride.
26. 7H-Pyrido[1,2,3-de]-1,4-benzoxazine-9-fluoro-2,3-dihydro-3-methyl-10-(3'-ethyl 4'-hydroxypiperidin-1'-yl)-7-oxo-6-carboxylic acid and its salts.
27. 7H-Pyrido[1,2,3-de]-1,4-benzoxazine-9-fluoro-2,3-dihydro-3-methyl-10-(3'-aminomethyl-4'-hydroxypiperidin-1'-yl)-7-oxo-6-carboxylic acid and its salt.
28. 1-Cyclopropyl-6,8-difluoro-5-methyl-1,4-dihydro-7-(3',3'-dimethyl-4'-ethylaminopiperidin-1-yl)-4-oxo-quinoline-3-carboxylic acid and its salt.
29. 1-cyclopropyl-6,7,8-trifluoro-5-methyl-1,4-dihydro-4-oxo-quinoline-3-carboxylic acid.

30. (S)-(−)-9-Fluoro-6,7-dihydro-8-(3',3'-dimethyl-4'-ethylaminopiperidin-1-yl)-5-methyl-1-oxo-1H,5H-benzo[i,j]auinolizine-2-carboxylic acid and its salts.
31. 1-Cyclopropyl-6-fluoro-1,4-dihydro-7-(3'-aminomethyl-4'-hydroxypiperidin 1-yl)-4-oxo-quinoline-3-carboxylic acid and its salts.
32. 1-Cyclopropyl-6-fluoro-1,4-dihydro-7-(4'-dimethylamino-3'-methylpiperidin-1-yl)-4-oxo-quinoline-3-carboxylic acid and its salts.
33. 5-Amino-1-cyclopropyl-6-fluoro-8-methoxy-1,4-dihydro-7-{4'-cyclopropylaminopiperidin-1-yl}-4-oxo-quinoline-3-carboxylic acid and its salts
34. 1-Cyclopropyl-6-fluoro-8-methoxy-1,4-dihydro-7-(4'-(t-butoxycarbonyl(L)-Ala-Ala)amino-3',3'-dimethylpiperidin-1-yl}-4-oxo-quinoline-3-carboxylic acid hydrochloride.
35. 5-Amino-1-cyclopropyl-6-fluoro-8-methoxy-1,4-dihydro-7-{4'-ethylamino-3',5'-dimethylpiperidin-1-yl}-4-oxo-quinoline-3-carboxylic acid and its salts.
36. Ethyl 1-(2,4-difluorophenyl)-6-fluoro-1,4-dihydro-7-(4-amino-3-ethylpiperidin-1-yl)-4-oxo-1,8-naphthyridine-3-carboxylate
37. 1-(2,4-difluorophenyl)-6-fluoro-1,4-dihydro-7-(4-amino-3,5-dimethylpiperidin-1-yl)-4-oxo-1,8-naphthyridine-3-carboxylic acid and its salts.
38. Ethyl 1-(2,4-difluorophenyl)-6-fluoro-5-methyl-1,4-dihydro-7-(4-amino-3,3-dimethylpiperidin-1-yl)-4-oxo-1,8-naphthyridine-3-carboxylate
39. (S)-(−)-9-fluoro-6,7-dihydro-8-(4'-hydroxy-3'-fluoropiperidin-1-yl)-5-methyl-1-oxo-1H,5H-benzo[i,j]quinolizine-2-carboxylic acid and its salts.
40. 10-Fluoro-11-(4-aminopiperidin-1-yl)-3,4-dihydro-4(S)-methyl-8-oxo-2H,8H-pyrido[1,2,3-ef]-1,5-benzoxazipin-7-carboxylic acid and its salt.
41. (RS)-(±)-6,7-dihydro-8-(trans-4'-hydroxy-3'-methylpiperidin-1-yl)-5-methyl-1-oxo-1H,5H-benzo[i,j]quinolizine-2-carboxylic acid and its salts.
42. (RS)-(±)-6,7-dihydro-8-(cis-4'-hydroxy-3'-methylpiperidin-1-yl)-5-methyl-1-oxo-1H,5H-benzo[i,j]quinolizine-2-carboxylic acid and its salts.
43. (RS)-(±)-6,7-dihydro-8-(4'-hydroxy-3',3'-dimethylpiperidin-1-yl)-5-methyl-1-oxo-1H,5H-benzo[i,j]quinolizine-2-carboxylic acid and its salts.

Particularly appropriate examples of a microbe appropriate for the use of an efflux pump inhibitor are pathogenic bacterial species, such as *Streptococcus pneumoniae, Streptococcus pyogenes, Pseudomonas aeruginosa, Escherischia coli, Staphylococcus aureus* which can be intrinsically resistant to commonly used antibacterial agents. Exposing these bacteria to an efflux pump inhibitor can significantly slow the export of an antibacterial agent from the interior of the cell or the export of siderophores. For instance, overexpression of the norA multidrug transporter has been reported for strains of *S. aureus* for fluoroquinolone resistance both in-vitro (Yoshida et. al., 1990; Kaatz et. al., 1990) and in-vivo (Trucksis et. al., 1991). Therefore, if another antibacterial agent is administered in conjunction with the efflux pump inhibitor, the antibacterial agent, which would otherwise be maintained at a very low intracellular concentration by the export process, can accumulate to a concentration which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species including those described above may contain similar broad substrate pumps, which actively export a variety of antimicrobial agents, and thus can also be appropriate targets.

In addition as suggested above, for some microbial, e.g., bacterial, species, efflux pump inhibitors can decrease the virulence of the microbe, for example, by inhibiting the transport of factors important for pathogenicity. Again using *P. aeruginosa* as an example, inhibition of an efflux pump in this bacterium inhibits the uptake of iron, which is important for pathogenicity. The mechanism of bacterial iron transport involves molecules called siderophores, which are synthesised and exported by bacterial cells via efflux pumps. These siderophores bind tightly to iron scavenged from the host, and are then taken up by the bacteria. In this way, the iron needed for bacterial metabolism is obtained, and an infection can be maintained.

Therefore, illustrating the utility of efflux pump inhibitors, inhibiting the efflux pump of *Streptococcus pneumoniae, Streptococcus pyogenes Pseudomonas aeruginosa, Escherischia coli, Staphylococcus aureus* allows obtaining one or more of the following biological effects:

1. *Streptococcus pneumoniae, Streptococcus pyogenes, Pseudomonas aeruginosa, Escherischia coli, Staphylococcus aureus* strains will become susceptible to antibiotics that could not be used for treatment of the respective bacterial infections, or become more susceptible to antibiotics which do inhibit the respective bacterial growth.
2. *Streptococcus pneumoniae, Streptococcus pyogenes, Pseudomonas aeruginosa, Escherischia coli, Staphylococcus aureus* strains will become more susceptible to antibiotics currently used for treatment of the respective bacterial infections.
3. Virulence of *Streptococcus pneumoniae, Streptococcus pyogenes, Pseudomonas aeruginosa, Escherischia coli, Staphylococcus aureus* will be attenuated because the availability of an essential siderephore bearing element will be hampered.
4. The inhibition of the pumps or of one of the components of the pumps may be lethal or prevent growth.

Obtaining even one of these effects provides a potential therapeutic treatment for infections by these bacteria. Also, as previously mentioned, similar pumps are found in other microorganisms. Some or all of the above effects can also be obtained with those microbes, and they are therefore also appropriate targets for detecting or using efflux pump inhibitors. Thus, the term "microbes" include, for example, bacteria, fungi, yeasts, and protozoa.

As indicated, the bacterium to be inhibited through the use of an efflux pump inhibitor can be from other bacterial groups or species, such bacterial groups of species including but not limited to one of the following:

*Pseudomonas aeruginosa, Pseudomonas fluorescens, Pseudomonas acidovorans, Pseudomonas alcaligenes, Pseudomonas putida, Stenotrophomonas maltophilia, Burkholderia capacia, Aeromonas hydrophilia, Escherichia coli, Citrobacter freundil, Salmonella tryphimurium, Salmonella typhi, Salmonella paratyphi, Salmonella enteritidis, Shigella dysenteriae, Shigella flexneri, Shigella sonnet, Enterobacter cloacae, Enterobacter aerogenes, Klebsiella pneumoniae, Klebsiella oxytoca, Serratia, marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus duicreyi, Pasteurella*

*multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Morazella, Gardenerella vaginalis, Bacteroides fragilis, Bacteroides distasonis, Bacteroides* 3452A homology group, *Bacteroides distasonis, Bacteroides ovalus, Bacteroides thetaiotaomicron, Bacteroides uniformis, Bacteroides eggerthii, Bacteroides splanchnicus, Clostridium diffile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis* and *Staphylococcus saccharolyticus.*

The term "efflux pump" refers to a protein assembly which exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump which spans the outer membrane. Certain efflux pumps will include a polypeptide which has at least 50% amino acid sequence similarity with a polypeptide which is part of the *Pseudomonas aeruginosa* mexA/mexB/oprM efflux pump or the efflux pump overexpressed by *P. aeruginosa* strain K385, or the efflux pump overexpressed by *P. aeruginosa* strain PAO40998E. Due to the described sequence similarity of a component polypeptide of the efflux pump, such an efflux pump is termed a *Pseudomonas aeruginosa*-type efflux pump.

An "efflux pump inhibitor" is a compound which specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity. Of particular interest in this invention, are compounds which inhibit the export or activity of efflux pumps which have a broad substrate range which includes antibacterial agents. The term *Streptococcus pneumoniae*-type efflux pump inhibitor refers to an efflux pump inhibitor which inhibits a *Streptococcus pneumoniae*-type efflux pump. The term *Pseudomonas aeruginosa*-type efflux pump inhibitor"refers to an efflux pump inhibitor which inhibits a *Pseudomonas aeruginosa*-type efflux pump. *Escherischia coli*, -type efflux pump. The term *Escherischia coli*-type efflux pump inhibitor refers to an efflux pump inhibitor which inhibits an *Escherischia coli*-type efflux pump. The term *Staphylococcus aureus*-type efflux pump inhibitor refers to an efflux pump inhibitor which inhibits a *Staphylococcus aureus*-type efflux pump.

In another aspect, this invention provides a method for treating a microbial infection, e.g., a bacterial infection, in an animal by administering to an animal suffering from such an infection an efflux pump inhibitor as described above in an amount sufficient to reduce efflux pump activity.

In a preferred embodiment, the inhibitor is one which decreases the pathogenicity of the microbe.

Such a decrease in pathogenicity can be obtained, for example, by interfering with essential bacterial element acquisition by inhibiting the transport of siderophores. The pathogenicity may also be reduced by reducing or eliminating the microbial products which cause tissue-damaging effects to the host. Other methods of reducing pathogenicity are, however, also within this aspect.

The host is an animal and may be, for example, chickens and turkeys, and in certain preferred embodiments in a mammal, e.g. a human.

In certain preferred embodiments, the microbial infection may be due to bacteria, which may, for example, be any of the bacterial species indicated above, but specifically including *Streptococcus pneumoniae, Pseudomonas aeruginosa, Escherischia coli, Staphylococcus aureus.*

In a related aspect, this invention provides a method of treating an animal suffering from a microbial infection by administering to the animal an efflux pump inhibitor in an amount sufficient to reduce efflux pump activity. In this aspect, the efflux pump inhibitor in one which reduces the in vivo viability of a microbe involved in the infection. By reducing the in vivo viability, the infected animal can more readily clear its body of the infection, or the microbes may even be killed. In particular embodiments the animal is a mammal. Also in particular embodiments, the microbe may be from one of a variety of pathogenic bacterial species, specifically including those listed above.

The term "in vivo viability" refers to the ability of a microbe, e.g., a bacterium, to survive or grow in a host, such as an animal. Therefore, an efflux pump inhibitor which reduces the in vivo viability of a microbe may stop the growth of the microbe and/or kill the microbe. Such efflux pump inhibitors, therefore, are antimicrobial agents.

In a further related aspect, this invention includes a method for prophylactic treatment of an animal, e.g., a mammal. In this method, an efflux pump inhibitor which reduces the pathogenicity of a microbe is administered to a mammal at risk of a microbial infection, e.g., a bacterial infection.

In a related aspect, the invention provides a method for treating a microbial infection in an animal, specifically including in a mammal, by treating an animal suffering from such an infection with an antimicrobial agent and an efflux pump inhibitor which increase the susceptibility of the microbe for that antimicrobial agent. In this way a microbe involved in the infection can be treated using the antimicrobial agent in smaller quantities, or can be treated with an antimicrobial agent which is not therapeutically effective when used in the absence of the efflux pump inhibitor. Thus, this method of treatment is especially appropriate for the treatment of infections using an antimicrobial agent alone due to a need for high dosage levels (which can cause undesirable side effects), or due to lack of any clinically effective antimicrobial agents. However, it is also appropriate for treating infections involving microbes which are susceptible to particular antimicrobial agents as a way to reduce the dosage of those particular agents. This can reduce the risk of side effects, but can also reduce the selection effect for highly resistant microbes resulting from the consistent high level use of a particular antimicrobial agent. In particular embodiment the microbe is a bacterium, which may, for example, be from any of the groups or species indicated above. Also in particular embodiments various antibacterial agents can be used. These include quinolones, tetracyclines, glycopeptides, aminoglycosides, beta-lactams, rifamycins, coumermycins, macrolides, and chloramphenicol. In particular embodiments an antibiotic of the above classes can be, for example, one of the following:

Beta-Lactam Antibiotics

Imipenem, meropenem, saneftrinem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriazone, cefurozime, cefuzonam, cephaaceterile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, amiclllin, azlocillin, carbenicillin, benzylpenicillin, carfecillin, cloxacillin, dicloxacillin, methicliloin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, Cefozopran, ME1228, KP-736, CP-6232, Ro 09-1227, OPC-20000, LY206763

Macrolides azithromycin, clarithromycin, erythromycin, oleandomycin, rokitamycin, rosaramicin, roxithromycin, troleandomycin, telithromycin and other ketolides.

Quinolones

Amifloxacin, cinoxacin, ciprofloxacin, enoxacin, fleroxacin, flumequine, loMefloxacin, nalidixic acid, norfloxacin, ofloxacin, levofloxacin, oxolinic acid, pefloxacin, difloxacin, marbofloxacin, rosoxacin, temafloxacin, tosufloxacin, sparfloxacin, clinafloxacin, trovafloxacin, alatrofloxacin, grepafloxacin, moxifloxacin, gatifloxacin, gemifloxacin, nadifloxacin, PD131628, PD140248, Q-35, AM-1155, NM394, T-3761, rufloxacin, OPC-17116, DU-6859a (identified in Sato, K. et. al., 1992, Antimicrob Agents Chemnother. 37:1491–98), DV-7751a (identified in Tanaka, M. et. al., 1992 Antimicrob Agents Chemother 37:2212–18).

Tetracyclines

Chlortetracycline, demeclocyline, doxycycline, lymecycline, methacycline, minocycline, oxytetracycline, tetracycline, Aminoglycosides Amikacin, arbekacin, butirosin, dibekacin, fortimicins, gentamicin, kanamycin, netilmicin, ribostanycin, sisomicin, spectinomycin, streptomycin, tobramycin, clindamycin, lincomycin.

Oxazolidinones

Linezolid, Eperezolid

Each of the above compounds have been reported in the literature. Other antibiotic compounds which may be identified which are effluxed by particular bacteria can also be utilised with the efflux pump inhibitors of this invention.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

As used herein, the term "treating" refers to administering a pharmaceutical composition for prophylactic and/or therapeutic purposes. The term "prophylactic treatment" refers to treating an organism such as a human patient, who is not yet infected, but who is susceptible to, or otherwise at risk of, a particular infection. The terms "susceptible" and "risk" do not refer to the status of organisms of that type generally, but rather refers to a significantly enhanced risk. Such risk may for example be due to a specific exposure to a particular potentially infective agent, to a generally weakened physical condition, or immune system deficiency. Preferably, for humans the enhanced risk is sufficient such that a prudent doctor familiar with the treatment of the potential infection would find prophylactic treatment medically warranted. The term "microbial infection" refers to a disease state or some adverse condition(s), such as the presence of a pathogenic microorganism in a body fluid like blood, urine, cerebrospinal or organ tissue, which are otherwise sterile or free of pathogenic microorganisms. The term "therapeutic treatment" refers to administering treatment to a patient already suffering from an infection. Thus, in preferred embodiments, treating is the administration to a mammal (either for therapeutic or prophylactic purposes) of therapeutically effective amounts of a potentiator and an antibacterial (or antimicrobial) agent in combination (either simultaneously or serially). The term "potentiator" refers to a compound such as an efflux pump inhibitor which has the ability to increase the concentration of existing antibiotics in a microbial cell.

By "therapeutically effective amount" or "pharmaceutically effective amount" is meant an amount of an efflux pump inhibitor, or amounts individually of an efflux pump inhibitor and an antimicrobial agent, as disclosed for this invention, which have a therapeutic effect, which generally refers to the inhibition to some extent of the normal metabolism of microbial cells causing or contributing to a microbial infection. The doses of efflux pump inhibitor and antimicrobial agent which are useful in combination as a treatment are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective if a microbial infection existed.

A therapeutic effect relieves, to some extent, one or more of the symptoms of the infection, and includes curing an infection. "Curing" means that the symptoms of active infections are eliminated, including the elimination of excessive numbers of viable microbes of those involved in the infection. However, certain long-term or permanent effects of the infection may exist even after a cure is obtained (such as extensive tissue damage).

The term "microbial infection" refers to the invasion of the host mammal by pathogenic microbes. This includes the excessive growth of microbes which are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population (s) is damaging the cells or other tissue of a mammal. Specifically, this description applies to a bacterial infection.

The term "administration" or "administering" refers to a method of giving a dosage of an antimicrobial pharmaceutical composition to a mammal, where the method is, e.g., topical, oral, intravenous, intraperitoneal, or intramuscular. The preferred method of administration can vary depending on various factors e.g., the components of the pharmaceutical composition, the site of the potential or actual bacterial infection, the microbe involved, and the severity of an actual microbial infection.

The term "mammal" is used in its usual biological sense. Thus, it specifically includes humans, cattle, horses, dogs, and cats, but also includes many other species.

This invention also features a method of enhancing the antimicrobial activity of an antimicrobial agent against a microbe, in which such a microbe is contacted with an efflux pump inhibitor, e.g., a non-tetracycline specific efflux pump inhibitor, to an efflux pump in the cell, and an antibacterial agent. The efflux pump inhibitor is a compound as described above. Thus, this method makes an antimicrobial agent more effective against a cell which expresses an efflux pump when the cell is treated with the combination of an antimicrobial agent and efflux pump inhibitor. In particular embodiments the microbe is a bacterium or a fungus, such as any of those described above; the antibacterial agent can be selected from a number of structural classes of antibiotics including, e.g., beta-lactams, glycopeptides, aminoglycosides, quinolones, tetracyclines, rifamycins, coumermycins, macrolides, and chloramphenicol. In particular embodiments an antibiotic of the above classes can be as stated above.

In a further aspect this invention provides pharmaceutical compositions effective for treatment of an infection of an animal, e.g., a mammal, by a microbe, such as a bacterium or a fungus. The composition includes a pharmaceutically acceptable carrier and an efflux pump inhibitor as described above. In preferred embodiments, such compositions contain efflux pump inhibitors, which are themselves effective antimicrobial agents, even in the absence of another antimicrobial agent (i.e., have intrinsic antimicrobial activity). Thus, pharmaceutical composition including such efflux pump inhibitors can be used either alone or in conjunction with another antimicrobial agent.

Also in preferred embodiments, the efflux pump inhibitors in pharmaceutical compositions of this aspect are efflux pump inhibitors which enhance the effectiveness of an antimicrobial agent other than the efflux pump inhibitor, so such compositions would generally be used in combination with such other antimicrobial agent. The invention also provides pharmaceutical compositions similarly effective for treatment of an infection of a mammal which include an efflux pump inhibitor and an antimicrobial agent. Similarly, the invention provides antimicrobial formulations which include an antimicrobial agent, an efflux pump inhibitor, and a carrier. In preferred embodiments, the antimicrobial agent is an antibacterial agent.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, $8^{th}$ Ed., Pergamon Press.

In yet another aspect, the invention provides a method of suppressing growth of a microbe, e.g., a bacterium, expressing an efflux pump, e.g., a non-tetracycline-specific efflux pump. As illustrated by the case where the microbe is a bacterium, the method involves containing that bacterium with an efflux pump inhibitor, e.g., a non-tetracycline-specific efflux pump inhibitor, in the presence of a concentration of antibacterial agent below the MIC of the bacterium. This method is useful, for example, to prevent or cure contamination of a cell culture by a bacterium possessing an efflux pump. However, it applies to any situation where such growth suppression is desirable.

In another related aspect, the invention provides a method for reducing a population of a microbe, e.g., a bacterial strain, involving contacting the population with an efflux pump inhibitor which inhibits a component of an efflux pump expressed in the microbe in that population, which is essential for the growth of the microbe expressing that efflux pump. In particular embodiments, that component is cytoplasmic membrane component. As indicated above, such efflux pump inhibitors may act in various ways, including, but not limited to, acting directly on the essential component, or acting to inhibit the expression of that component.

The term "reducing a population" means that the microbes of that population are being killed. This is distinguished from the action of a static agent, e.g., a bacteriostatic agent, which prevents the bacteria from growing and multiplying but does not kill the microbes. Accordingly, in the context of this aspect, an "essential component" of an efflux pump is one which is essential to the in vivo survival of the microbe, i.e., the survival in a host.

In yet another aspect, this invention provides a method for enhancing growth of an animal by administering an efflux pump inhibitor to the animal, which inhibits an efflux pump expressed in a bacterial strain in the animal, and which inhibits the growth of the bacterial strain. Such a growth enhancing effect may result from the reduced energy consumption by the bacteria, which increases the food energy available to the animal. This method is appropriate, for example, for use with cattle, swine, and fowl such as chickens and turkeys.

In an additional aspect, the invention provides novel compounds having efflux pump activity. These compounds have chemical structures as described above.

As indicated above, while the present invention is presently exemplified by activity against bacteria, compounds of the present invention also have activity against other microbes, for example against yeasts and/or other fungi. Thus, the above aspects also include embodiments in which described compounds are active or effective against such other microbes.

In further aspect, the invention provides a method of making a pharmaceutical composition comprising the steps of identifying an efflux pump inhibitor having a chemical structure of the formula I; synthesizing said efflux pump inhibitor and preparing a pharmaceutical composition containing said efflux pump inhibitor. The efflux pump inhibitor may have the chemical structure as described above. The pharmaceutical composition may also contain one or more antimicrobial agents, e.g., as identified above, and one or more carriers, diluents, and excipients. Further, in preferred embodiments, the efflux inhibitor compound is active against a microbe, e.g., a bacterium, as identified above.

Identification of Efflux Pump Inhibitors

Identification of efflux pump inhibitors having structures as described for the present invention was performed using screening methods known to those skilled in the art of biological techniques and are described in detail below. In particular, the screening method based on inhibition of microbial growth in the presence of a subinhibitory concentration of an antibacterial agent which is normally effluxed by the test microbe and a concentration of a test compound was used for identifying some of the active compounds disclosed herein. In this method, inhibition of growth of the microbe is indicative that export of the antibacterial agent is inhibited by the test compound, and that the test compound is therefore an efflux pump inhibitor. The mode of action of the test compound so identified can then be confirmed as inhibiting active efflux. However, other screening methods for detecting efflux pump inhibitors can also be used.

Synthesis of Derivatives of Efflux Pump Inhibitors from Screening

The inventors have screened a library of synthetic chemicals and identified several compounds that effectively inhibit the respective efflux pumps of *Staphylococcus aureus* 1199B NorA$_+$, *Streptococcus pneumoniae* 3514, *Pseudomonas aeruginosa* 23587, *Escherischia coli* 2051. Some of these compounds were found to be also effective against presently unidentified multidrug transporters of other microorganisms.

The library of compounds was obtained by synthesis according to methods as described in our copending applications PCT application PCT/IN99/00016, U.S. application Ser. Nos. 09/566,875, 09/640,947, and 09/850,669 and by methodologies described in a later section below.

Exemplary compounds of the present invention were synthesised by methods as described in the examples below. Those skilled in the art will understand how to synthesise additional compounds within the scope of this invention based on the described syntheses and the knowledge of those skilled in the art of chemical synthesis.

The following examples illustrate methods of screening, which have led to the identification of efflux pump inhibitors. They, however, do not limit the scope of methods that can be used for screening or the kinds of efflux pump inhibitors that can be found by such varied methods.

Screening of Efflux Pump Inhibitors—In-vivo

Inhibitors of the bacterial efflux pumps are generally initially characterised in vitro. Those which show effective inhibition of the pump(s) and which show synergistic activity with antibiotics are selected for evaluation in vivo. Efficacy testing will be done using standard procedures. Primary efficacy evaluation may be done using the murine septicemia model (M. G. Bergeron, 1978, Scand. J. Infect. Dis. Suppl. 14:189–206; S. D. Davis, 1975, Antimicrob. Agents Chemother. 8:50–53). In this model a supra-lethal dose of bacteria is used to challenge the rodents. Treatment is initiated, varying either or both time(s) of treatment and dose of antibiotic. In these experiments both the antibiotic and the efflux pump inhibitor doses are varied. A positive result is indicated by significant increase in protection from the lethal infection by the combination of the potentiator (the efflux pump inhibitor) and the antibiotic versus the antibiotic alone.

A second efficacy model which is used is the mouse soft tissue infection model (Vogelman et. al. 1988, J. Infect. Dis. 157:287–298). In this model anaesthetised mice are infected with an appropriate titer of bacteria in the muscle of the hind thigh. Mice are either neutropenic (cyclophosphamide treated at 125 mg/kg on days −4, −2, and 0) or immunocompetent. The infecting dose is commonly $10^5$–$10^6$ colony forming units per animal. Treatment with the combination of the efflux pump inhibitor and/or antibiotics follows infection, or can occur before infection. The proliferation (or death) of the bacteria within the thigh muscle is monitored over time. Effective combinations show greater activity than the antibiotic alone. Activity is defined as reduction in growth rate of the test bacteria in the murine tissue.

Pharmaceutical Compositions and Modes of Administration

The particular compound that is an efflux pump inhibitor can be administered to a patient either by itself, or in combination with an antimicrobial, e.g., antibacterial, agent, or in pharmaceutical compositions where it is mixed with a suitable carrier(s) or excipient(s) or diluent(s). A combination of an efflux pump inhibitor with an antimicrobial agent can be of at least two different types. In one, a quantity of an efflux pump inhibitor is combined with a quantity of an antimicrobial agent in a mixture, e.g., in a solution or powder mixture. In such mixtures, the relative quantities of the inhibitor and the antimicrobial agent may be varied as appropriate for the specific combination and expected treatment. In a second type of combination an inhibitor and an antimicrobial agent can be covalently linked in such manner that the linked molecules can be cleaved within the cell. However, the term "in combination" can also refer to other possibilities, including serial administration of an inhibitor and other antimicrobial agent. In addition, an efflux pump inhibitor and/or another antimicrobial agent may be administered in pro-drug forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage and dosage form employed and the route of administration utilised. It is preferable that the therapeutic serum concentration of an efflux pump inhibitor should be in the range of 0.1–100 mcg/mL, more preferably 0.1–50 mcg/ml, even more preferably 0.1–20 mcg/ml, even more preferably 1.0–50 mcg./mL or most preferably 1.0–20 mcg/mL.

For any compounds used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful dosage in humans. Levels in plams may be measured, e.g. by HPLC.

In particular preferred embodiments, the efflux inhibitor in a pharmaceutical composition has a structure as shown by the generic structures described above.

The exact formulation, route of administration and dosage can be chosen by the individual physician in view of the patients condition. (See e.g. Fingl et. al., in The Pharmacological Basis of Therapeutics, 1975, Ch. 1, p. 1). It should be noted that the attending physician would know how and when to terminate, interrupt or adjust administration due to toxicity, or to organ dysfunctions. Conversely, the attending physician would also know to adjust treatment to higher levels if the clinical response were not adequate, (precluding toxicity). The severity of the condition may, for example, be evaluated, in part, by standard prognostic evaluation methods. Further, the does and perhaps dose frequency will also vary according to the age, body weight and response of the individual patient. A programme comparable to that discussed above may be used in veterinary medicine.

Depending on the specific infection being treated, such agents may be formulated and administered systemically or locally. Techniques for formulation and administration may be found in Remington's Pharmaceutical Sciences, $19^{th}$ ed., Mack Publishing Co., Easton, Pa. (1990). Suitable routes may include oral, rectal, transdermal, vaginal, transmucosal, or intestinal administration; parentral delivery, including intramuscular, subcutaneous, intramedullary, injections, as well as intrathecal, direct intraventricular, intravenous, intraperitonial, intranesal, or intraocular injections just to name a few.

The pharmaceutical compositions are prepared according to conventional procedures used by persons skilled in the art to make stable and effective compositions. In the solid, liquid, parenteral and topical dosage forms, an effective amount of the active compound or the active ingredient is any amount, which produces the desired results.

For the purpose of this invention the pharmaceutical compositions may contain the active compounds of the invention, their derivatives, salts or hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emolients, wetting agents, disintegrants, surface active agents and lubricants which are usually employed to prepare such drugs depending on the type of dosage form.

Any suitable route of administration may be employed for providing the patient with an effective dosage of the compound of the invention, their derivatives, salts or hydrates thereof. For example, oral, rectal, parenteral (subcutaneous, intramuscular, intravenous), transdermal, topical and like forms of administration may be employed. Dosage forms include (solutions, suspensions, etc) tablets, pills, powders, troches, dispersions, suspensions, emulsions, solutions, capsules, injectable preparations, patches, ointments, creams, lotions, shampoos and the like.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

The compositions of the present invention include compositions such as suspensions, solutions, elixirs, aerosols, and solid dosage forms. Carriers as described in general above are commonly used in the case of oral solid preparations (such as powders, capsules and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatine solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol.

The tablet, if desired, can be coated, and made into sugar-coated tablets, gelatine-coated tablets, enteric-coated tablets, film-coated tablets, or tablets comprising two or more layers.

If desired, tablets may be coated by standard aqueous or nonaqueous techniques.

In moulding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, gelatine, and semisynthetic glycerides.

A second preferred method of administration is parenteraily for intramuscular, intravenous or subcutaneous administration.

A third preferred route of administration is topically, for which creams, ointments, shampoos, lotions, dusting powders and the like are well suited.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

The antimicrobial pharmaceutical composition may further contain ordinary dissolving aids, buffers, pain-alleviating agents, and preservatives, and optionally colouring agents, perfumes, flavours, sweeteners, and other drugs.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

It will be apparent to those skilled in the art that many modifications, both to materials and methods may be practised without departing from the purpose and scope of this invention.

Preparations of intermediates and of exemplary compounds of the invention

The compounds of the present invention may be readily prepared in accordance with the following synthesis schemes, as illustrated in the specific examples provided. However, those skilled in the art will recognise that other synthetic pathways for forming the compounds of this invention can be utilised, and that the following is provided merely by way of example and is not limiting to the present invention. It will be further recognised that various protecting and deprotecting strategies will be employed which are standard in the art (see e.g., "Protective Groups in Organic Synthesis", by Green and Wuts). Those skilled in the art will recognise that the selection of any particular protecting group (e.g. amine, hydroxy and carboxyl protecting groups) will depend on the stability of the protected moiety with regard to the subsequent reaction conditions and will understand the appropriate selection.

General Procedures for Preparing the Compounds of the Invention.

A 7-halo quinolone of the structure shown below

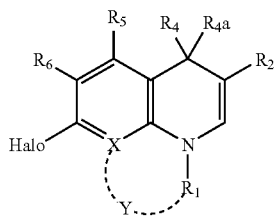

where halo represents F, Cl, or Br, $R_2$ represents COOH, COOCH$_3$, COOC$_2$H$_5$, $R_2$, $R_4$ and $R_{4a}$ taken together represents a difluoroboron coordination complex shown as —C(=O)OB(F$_2$) . . . O= or R2, R4 and R4a taken together represents a diacetoxyboron coordination complex shown as —C=O(O)B(OAc)$_2$ and $R_1$, $R_4$, $R_{4a}$, $R_5$, $R_6$, X and Y are as hereinbefore described is treated with an appropriate amine of the formula R9R10NH, where $R_9$ and $R_{10}$ have the meanings hereinbefore described in an organic solvent such as acetone, alcohol, acetonitrile, dimethyl sulphoxide, N,N-dimethylformamide preferably acetonitrile or dimethyl sulphoxide, optionally in the presence of a base such as triethylamine, pyridine, 1,5-diazabicyclo[4.3.0]non-5-ene (DBN), diazabicyclo[5.4.0]undec-7-ene (DBU) preferably triethylamine at 50° C.–120° C., preferably 70° C.–90° C. for 4–24 hr. When R2 represents COOCH3 or COOC2H5 or R2, R4 and R4a represent —C(=O)OB(F$_2$) . . . O= or C=O(O)B(OAc)$_2$ or —C(=O)OB(Oac)$_2$, the product obtained is hydrolised by aqueous alkali preferably sodium hydroxide or a base preferably triethylamine in solution in a solvent such as ethanol.

a) The compounds I of the invention which are esters at a carboxylic acid group may be prepared by treating the free acid of compounds of formula I in solution in an appropriate solvent, preferably N,N-dimethyl formamide, with the corresponding halo compound, preferably chloro or bromo-compound, in the presence of a base, preferably anhydrous potassium carbonate, at an elevated temperature, preferably 50° C. for an extended period of time, preferably 6 hours.

b) The compounds of the invention which are esters at a carboxylic acid group may be prepared by treating the free acid of compound of formula I in solution in an appropriate solvent, preferably N,N-dimethylacetamide, with the corresponding hydroxy compound, in the presence of a base, preferably triethylamine, in presence of a catalyst, preferably 4-N,N-dimethylaminopyridine, and in the presence of a dehydrating agent, preferably N,N-dicyclohexylcarbodiimide at an elevated temperature, preferably 100° C. for an extended period of time, preferably 24 hours.

c) The compounds of formula I of the invention which are amides at a carboxylic acid groups may be prepared by coupling the free acid of compound of formula I with ammonia or an appropriate amine or an amino acid appropriately protected at the acid functionality of the amino acids with a protecting group. The —COOH protecting groups for amino acids are known in the art. Examples of suitable —COOH protecting groups for amino acids are methyl, ethyl, t-butyl and benzyl groups. The —COOH protecting group is removed by hydrolysis or by hydrogenation. The coupling of a —COOH group of compound of formula I with the amino group of the amino acid is also known in the art. The reaction may be conducted with or without a solvent at a range of temperatures in the presence of a coupling agent.

d) The compounds of the invention which are amides at an NH2 or an NH group are prepared by coupling the free amino group of a compound of formula I or by coupling the free NH bearing compound of formula I with an appropriate acylating agent such as an acyl anhydride or an acyl chloride in the presence of a condensing agent such as a base e.g. triethylamine or aqueous sodium hydroxide optionally in the presence of a solvent such as N,N-dimethyl acetamide at an elevated temperature of 50° C.–100° C. for an extended period of time upto 24 hours. For compound that contain two NH2 groups, two NH groups or one NH2 and one NH group, it may be necessary when so desired to use a protecting group on the NH2 group or NH group which is desired to remain unreactive. Protecting groups for NH2 and NH groups are well known to those skilled in the art.

e) The compounds of the invention which are esters of a free hydroxy group may be prepared by treating the free hydroxy compound of formula I with an organic acid, an organic dibasic acid or appropriate N-protected amino acid or polypeptide as defined above. Nitrogen protecting groups are known in the art. Examples of suitable nitrogen protecting groups are C$_1$–C$_6$ acyl, C$_2$–C$_6$ alkoxycarbonyl optionally substituted benzyloxycarbonyl, aryloxycarbonyl, silyl, trityl, tetrahydropyranyl, vinyloxycarbonyl, O-nitrophenylsulfonyl, diphenylphosphinyl, p-toluenesulfonyl, and benzyl. The nitrogen protecting group is removed by methods known in the art such as hydrogenation or hydrolysis. The ester forming reaction may be conducted with or without a solvent at a range of temperatures in the presence of a suitable condensing agent, known to those skilled in the art.

f) The compounds of the invention which are alkyl ethers of a free hydroxy group may be prepared by treating the compound bearing the free hydroxy group with an alkyl halide in an organic solvent in the presence of a base or a condensing agent at temperatures upto the boiling point of the solvent for a period of time upto 24 hours, by methods known to those skilled in the art.

g) The compounds of the invention which are mono or dialkyl derivatives of a free amino group may be prepared by treating the compound bearing the free amino group with appropritae molar amounts of an alkylhalide in an organic solvent optionally in the presence of a base or a condensing agent at temperatures upto the boiling point of the solvent for a period of time up to 24 hours, by methods known to those skilled in the art.

h) General Method for making aminoacid esters at the 8-(4'-hydroxypiperidine substituent of RS-/R-/S-9-Fluoro-6,7-dihydro-8-(4'-hydroxypiperidin-1-yl)-5-methyl-1-oxo-1H,5H-benzo[i,j]quinolizine-2-carboxylic acid Nadifloxacin (1 mm, 360 mg), and triethylamine (1 mm, 0.145 ml) was dissolved in dimethylacetamide (15 ml). t-Butyloxycarbonyl aminoacid (1.2 mm) and dimethylaminopyridine (1.2 mm, 150 mg) were added, followed by dicyclohexylcarbodiimide under ice cooling. After 30 minutes at 0° C., the mixture was stirred at room temperature overnight. Dicyclohexylurea was filtered and the mixture was diluted with ethylacetate, transferred in a separating funnel, washed with 0.5 N hydrochloric acid, 1 N sodiumbicarbonate and brine,dried over sodium sulphhate and evaporated to give t-butoxycarbonylaminoacyloxy derivative of RS-/R-/S-9-fluoro-6,7-dihydro-8-(4'-hydroxypiperidin-1-yl)-5-methyl-1-oxo-1H,5H-benzo[i,j]quinolizine-2-carboxylic acid Trifluoroacetic acid (10 ml) was added to the product obtained in the previous step. After 30 mins at room temperature, the acid was evaporated and the trifluoroacetate salt was precipitated by addition of ether. If need be the product could be purified by high pressure liquid chromatography on a C8 or C18 column. Dissolving the trifluoroacetate salt in 0.1 N hydrochloride acid and freeze drying provided the hydrochloride salt.

i) General Method for making an amide derivative at the 2-carboxyl substituent of RS-/R-/S-9-Fluoro-6,7-dihydro-8-(4'-hydroxypiperidin-1-yl)-5-methyl-1-oxo-1H,5H-benzo[i,j]quinolizine-2-carboxylic acid using an alpha amino acid RS-/R-/S-9-Fluoro-6,7-dihydro-8-(4'-hydroxypiperidin-1-yl)-5-methyl-1-oxo-1H,5H-benzo[i,j]quinolizine-2-carboxylic acid (1 mm, 360 mg), and triethylamine (1 mm, 0.145 ml) were are dissolved in dimethylacetamide (15 ml). Isobutylchloroformate (1 mm, 0.13 ml) was added under ice cooling, After 5 min a solution of amino acid ester hydrochloride (2 mm) and triethylamine (2 mm, 0.28 ml) in dimethylacetamide (10 ml) was added followed by dimethylaminopyridine (1 mm, 125 mg) and the mixture was stirred at room temperature overnight. The mixture was then diluted with ethyl acetate, transferred in a separating funnel, washed with 0.5 N hydrochloric acid, 1 N sodium bicarbonate and brine, dried over sodiumsulphate and evaporated to give the ester of the respective amide from RS-/R-1S-9-Fluoro-6,7-dihydro-8-(4'-hydroxypiperidin-1-yl)-5-methyl-1-oxo-1H,5H-benzo[i,j]quinolizine-2-carboxylic acid.

The ester was dissolved in methanol, 1 N sodium hydroxide (1.1 eqivalent) was added. The mixture was acidified, extracted with ethylacetate, washed with brine, dried over sodiumsulphate and evaporated to provide the title compound. If need be the product may be purified by high pressure liquid chromatography on a C8 or C18 column. Optionally, dissolving the acid in water with one equivalent sodiumbicarbonate followed by freeze drying provided the sodium salt of the title compound.

j) The pharmaceutically acceptable acid addition salts of compounds I are prepared in a conventional manner by treating a solution or suspension of the free base I with about one chemical equivalent of a pharmaceutically acceptable acid. Conventional concentration and recrystalisation techniques are employed in isolating the salts. Illustrative of suitable acids are hydrochloric, hydrobromic, hydroiodic, sulphuric, sulfamic, sulfonic, phosphoric, acetic, lactic, succinic, oxalic, maleic, fumaric, malic, tartaric, citric, ascorbic, gluconic, benzoic, cinnamic, methanesulfonic and p-toluenesulfonic acid.

k) The pharmaceutically acceptable cationic salts of compounds of formula I may be prepared by conventional methods from the corresponding acids e.g. by reaction with about one equimolar amount of a base. Examples of suitable cationic salts are those of alkali metals such as lithium, sodium or potassium, alkaline earth metals such as magnesium or calcium or ammonium or organic amines such diethanolamine, N-methylglucamine, guanidine or heterocyclic amines such as choline, piperidine, N-methyl-4-hydroxypiperidine, hydroxyethylpyrrolidine, hydroxyethylpiperidine, morpholine, hydroxyethylmorpholine, piperazine, N-methylpiperazine and the like or basic amino acids such as optically pure or racemic isomers of arginine, lysine, histidine, tryptophan and the like.

The following examples describe the methods of synthesis of the compounds of the invention.

Some Preferred Compounds of the Invention Displaying Inhibition of the Efflux Pump of *Staphylococcus aureus* 1199 B (Nor A$^+$)

EXAMPLE 1

1-Ethyl-6-fluoro-1,4-dihydro-7-(1',2',3',4'-tetrahydroisoquinolin-2-yl)-4-oxo-quinoline-3-carboxylic acid A mixture of 1-ethyl-6,7-difluoro-1,4-dihydro-4-oxo-quinolone-3-carboxylic acid (2.5 g, 8.3 mmole), 1,2,3,4-tetrahydroisoquinoline (1.67 g, 16,7 mmole) and triethylamine (0.5 ml) in DMSO (15 ml) was stirred at 140° C. for 24 hr and concentrated in vacuum and the residue thus obtained was triturated with 25 ml water. The solid separated was filtered and dried to furnish the required product. Yield 2.0 g (62%), m.p. 220° C. $C_{21}H_{19}FN_2O_3$, m/z 385 (M+1).

EXAMPLE 2

1-Ethyl-6,8-fluoro-1,4-dihydro-7-(4'-acetoxypiperidin-1-yl)-4-oxo-quinoline-3-carboxylic acid A mixture of 1-ethyl-6,7-difluoro-1,4-dihydro-4-oxo-quinolone-3-carboxylic acid (2.5 g, 8.3 mmole), 1,2,3,4-tetrahydroisoquinoline (1.67 g, 16,7 mmole) and triethylamine (0.5 ml) in DMSO (15 ml) was stirred at 140° C. for 24 hr and concentrated in vacuum and the residue thus obtained was triturated with 25 ml water. The solid separated was filtered and dried to furnish the required product. Yield 56%, m.p. 220–22° C. $C_{21}H_{19}FN_2O_3$, m/z 395 (M+1).

EXAMPLE 3

1-Ethyl-6,8-fluoro-1,4-dihydro-7-(4'-{2'-(2'-oxazolidin-1yl)ethyl}piperazin-1-yl)-4-oxo-quinoline-3-carboxylic acid A mixture of 1-ethyl-6,7-difluoro-1,4-dihydro-4-oxo-quinolone-3-carboxylic acid (2.5 g, 8.3 mmole), 1,2,3,4-tetrahydroisoquinoline (1.67 g, 16,7 mmole) and triethylamine (0.5 ml) in DMSO (15 ml) was stirred at 140° C. for 24 hr and concentrated in vacuum and the residue thus obtained was triturated with 25 ml water. The solid separated was filtered and dried to furnish the required product. Yield 42%, m.p. 192–94° C. $C_{21}H_{24}F_2N_4O_5$, m/z 451 (M+1).

EXAMPLE 4

1-Ethyl-6,8-difluoro-1,4-dihydro-7-{(1α,5α,6α)-6-amino-3-azabicyclo[3.1.01]-hex-3-yl}-4-oxo-quinoline-3-carboxylic acid The condensation of (1α,5α,6α)-6-t-butoxycarbonylamino-3-azabicyclo[3.1.0]-hexane with 1-Ethyl-6,7,8-trifluoro-1,4-dihydro-4-oxo-quinoline-3-carboxylic acid was carried in similiar manner as described in example 1 which on hydrolysis with conc. HCl furnished titled product. Yield 60%, m.p 224–26° C., $C_{17}H_{17}F_2N_3O_3$, m/z 350 (M+1).

EXAMPLE 5

5-Amino-1-ethyl-6,8-difluoro-1,4-dihydro-7-(3'-amino-5'-methylpyrrolidin-1-yl)-4-oxo-quinoline-3-carboxylic acid The condensation of 5-amino-1-ethyl-6,7,8-trifluoro-1,4-dihydro-4-oxo-quinolne-3-carboxylic acid with 3-amino-5-methylpyrrolidine in a similar manner as described in example 1 give the titled product. Yield 41%, m.p 238–40° C., $C_{17}H_{19}F_2N_4O_3$, m/z 393 (M+1).

EXAMPLE 6

5-Amino-1-ethyl-6,8-difluoro-1,4-dihydro-7-(4'-aminopiperidin-1-yl)-4-oxo-quinoline-3-carboxylic acid It was prepared according to procedure described in example 5 where 4-aminopiperidine was used in place of 3-amino-5-methylpyrrolidine. Yield 67%, m.p 204–06° C., $C_{20}H_{28}F_2N_4O_3$, m/z 411 (M+1).

EXAMPLE 7

5-Amino-1-ethyl-6,8-difluoro-1,4-dihydro-7-{4'-(acetamido)piperidin-1-yl}-4-oxo-quinoline-3-carboxylic acid It was prepared in a similar manner as described in example 5 where 4-(acetamido)piperidine was used in place of 3-amino-5-methylpyrrolidine. Yield (45%), m.p 280–82° C., $C_{19}H_{22}F_2N_4O_5$, m/z 425 (M+1).

EXAMPLE 8

5-Amino-1-ethyl-6,8-difluoro-1,4-dihydro-7-[(1α,5α,6α)-6'-(N-t-butoxycarbonylamino)-3-azabicyclo[3.1.0]-hex-3-yl}-4-oxo-quinoline-3-carboxylic acid It was prepared according to procedure described in example 5 where (1α,5α,6α)-6-(N-t-butoxycarbonylamino)-3-azabicyclo[3.1.0]-hexane was used in place of 3-amino-5-methylpyrrolidine and the t-butoxycarbonyl protecting group in the product was removed using conc. HCl . . . Yield 92 mg (47%), m.p 220–22° C., $C_{22}H_{26}F_2N_4O_4$, m/z 449 (M+1).

EXAMPLE 9

1-Cyclopropyl-6-fluoro-1,4-dihydro-7-(3'-acetamido-5'-methylpyrrolidin-1-yl)-4-oxo-quinoline-3-carboxylic acid The condensation of 1-cyclopropyl-6-fluoro-7-chloro-1,4-dihydro-4-oxo-quinoline-3-carboxylic acid with 3-acetamido-5-methylpyrrolidine in a similar manner as described in example 1 give the titled product. Yield (68%), m.p 270–72° C., $C_{20}H_{22}FN_3O_4$, m/z 388 (M+1).

EXAMPLE 10

1-Cyclopropyl-6-fluoro-1,4-dihydro-7-(3'-amino-5'-methylpyrrolidin-1-yl)-4-oxo-quinoline-3-carboxylic acid It was prepared in a similar manner as described in example 9 where 3-amino-5-methylpyrrolidin was used in place of 3-acetamido-5-methylpyrrolidine to furnish the titled product. Yield (41%), m.p 346° C., $C_{18}H_{20}FN_3O_3$, m/z 346 (M+1).

EXAMPLE 11

1-Cyclopropyl-6-fluoro-1,4-dihydro-7-(4'-acetoxypiperidin -1-yl)-4-oxo-quinoline-3-carboxylic acid It was prepared in a similar manner as described in example 9 where 4-acetoxypiperidine was used in place of 3-acetamido-5-methylpyrrolidine. Yield 50%, m.p 258–60° C., $C_{21}H_{17}F_5N_4O_3$, m/z 469 (M+1).

EXAMPLE 12

1-Cyclopropyl-6-fluoro-1,4-dihydro-7-(4'-(N-dimethylamino)piperidin-1-yl)-4-oxo-quinoline-3-carboxylic acid It was prepared in a similar manner as described in example 9 where 4-(N-dimethylaminopiperidine was used in place of 3-acetamido-5-methylpyrrolidine. Yield 59%, m.p 284–86° C., $C_{21}H_{23}FN_2O_5$, m/z 403 (M+1)

EXAMPLE 13

1-Cyclopropyl-6-fluoro-1,4-dihydro-7-(3',5'-dimethylpiperidin-1-yl)-4-oxo-quinoline-3-carboxylic acid It was prepared in a similar manner as described in example 9 where 3,5-dimethylpiperidine was used in place of 3-acetamido-5-methylpyrrolidine. Yield 23%, m.p 212–14° C., $C_{20}H_{23}FN_2O_3$, m/z 359 (M+1).

EXAMPLE 14

1-Cyclopropyl-6-fluoro-1,4-dihydro-7-(4'-hydroxy-3',5'-dimethylpiperidin-1-yl)-4-oxo-quinoline-3-carboxylic acid It was prepared in a similar manner as described in example 9 where 4-hydroxy-3,5-dimethylpiperidine was used in place of 3-acetamido-5-methylpyrrolidine. Yield 38%, m.p 178–80° C., $C_{20}H_{23}FN_2O_4$, m/z 375 (M+1).

EXAMPLE 15

1-Cyclopropyl-6-fluoro-1,4-dihydro-7-(3',4',5'-trimethylpiperazin-1-yl)-4-oxo-quinoline-3-carboxylic acid It was prepared in a similar manner as described in example 9 where 3,4,5-trimethylpiperazine was used in place of 3-acetamido-5-methylpyrrolidine. Yield 48%, m.p 200–02° C., $C_{20}H_{24}FN_3O_3$, m/z 373 (M+1).

EXAMPLE 16

1-Cyclopropyl-6-fluoro-1,4-dihydro-7-(3',5'-dimethyl-4'-ethylpiperazin-1-yl)-4-oxo-quinoline-3-carboxylic acid It was prepared in a similar manner as described in example 9 where (3,5-dimethyl-4-ethylpiperazine was used in place of 3-acetamido-5-methylpyrrolidine. Yield 79%, m.p 215–20° C., $C_{21}H_{26}FN_3O_3$, m/z 388 (M+1).

EXAMPLE 17

1-Cyclopropyl-6-fluoro-1,4-dihydro-5-methyl-7-(4'-ethoxypiperidin-1-yl)-4-oxo-quinoline-3-carboxylic acid The condensation of 1-cyclopropyl-6,7-difluoro-5-methyl-1,4-dihydro-4-oxo-quinoline-3-carboxylic acid with 4-ethoxypiperidine in a similar manner as described in example 1 give the titled product. Yield 40%, m.p 180–82° C., $C_{21}H_{21}FN_2O_4$, m/z 388 (M+1).

EXAMPLE 18

1-Cyclopropyl-6-fluoro-1,4-dihydro-5-methyl-7-(3',3'-dimethylpiperazin -1-yl)-4-oxo-quinoline-3-carboxylic acid It was prepared in a similar manner as described in example 17 where 3,3-dimethylpiperazine was used in place of 4-ethoxypiperidine. Yield 50%, m.p 238–42° C., $C_{20}H_{24}FN_3O_3$, m/z 374 (M+1).

EXAMPLE 19

1-Cyclopropyl-6-fluoro-8-methoxy-1,4-dihydro-7-{4'-(N-dimethylamino)-3'-methylpiperidin-1-yl}-4-oxo-quinoline-3-carboxylic acid A mixture of [1-cyclopropyl-6,7-difluoro-1,4-dihydro-8-methoxy-4-oxo-quinoline-3-carboxylate-$O^3$, $O^4$]difluoroboron chelate (100 mg, 0.29 mmole) and 4-(N-dimethylamino)-3-methylpiperidine (100 mg, 0.7 mmole) in acetonitril (5 ml) was stirred at 80° C. for 6 hr and cooled. Solvent was removed borate complex was heated under reflux using triethylamine (0.1 ml) in ethanol (5 ml) solvent was removed and solid obtained was purified on silica column to furnish the required product. Yield 74%, $C_{22}H_{28}FN_3O_4$, m.p. 180–82° C. m/z 417 (M+1).

EXAMPLE 20

1-Cyclopropyl-6-fluoro-8-methoxy-1,4-dihydro-7-(4'-hydroxy-3'-isobutylpiperidin-1-yl)-4-oxo-quinoline-3-carboxylic acid It was prepared in a similar manner as described in example 19 where 4-hydroxy-3-isobutylpiperidine was used in place of 4-(N-dimethylamino)-3-methylpiperidine. Yield (59%), m.p. 190–92° C., $C_{23}H_{29}FN_7O_5$, m/z 433 (M+1).

EXAMPLE 21

1-Cyclopropyl-6-fluoro-8-methoxy-1,4-dihydro-7-(4'-hydroxy-3',3'-dimethylpiperidin-1-yl)-4-oxo-quinoline-3-carboxylic acid It was prepared in a similar manner as described in example 19 where 4-hydroxy-3,3-dimethylpiperidine was used in place of 4-(N-dimethylamino)-3-methylpiperidine. Yield 29%, m.p 240–42° C., $C_{21}H_{25}FN_2O_4$, m/z 405 (M+1).

EXAMPLE 22

1-Cyclopropyl-6-fluoro-8-methoxy-1,4-dihydro-7-(4'-hydroxy-3',5'-dimethylpiperidin-1-yl)-4-oxo-quinoline-3-carboxylic acid It was prepared according to procedure described in example 19 where 4-hydroxy-3,5-dimethylpiperidine was used in place of 4-(N-dimethylamino)-3-methylpiperidine. Yield 27%, m.p 230–32° C., $C_{21}H_{27}FN_3O_4$, m/z 405 (M+1).

EXAMPLE 23

1-Cyclopropyl-6-fluoro-8-methoxy-1,4-dihydro-7-(3'-methylpiperazin-1-yl)-4-oxo-quinoline-3-carboxylic acid It was prepared in a similar manner as described in example 19 where 3-methylpiperazine was used in place of 4-(N-dimethylamino)-3-methylpiperidine. Yield (48%), m.p 260–61° C., $C_{19}H_{22}FN_3O_4$, m/z 375 (M+1).

EXAMPLE 24

5-Amino-1-cyclopropyl-6-fluoro-8-methoxy-1,4-dihydro-7-(cis-4'-amino-3',5'-dimethylpiperidin-1-yl)-4-oxo-quinoline-3-carboxylic acid The condensation of 5-amino-1-cyclopropyl-6,7-difluoro-1,4-dihydro-4-oxo-quinoline-3-carboxylic acid with cis-4-amino-3,5-dimethylpiperidine in a similar manner as described in example 1 gave the titled product. Yield 37%, m.p 248–50° C., $C_{21}H_{27}FN_4O_4$, m/z 419 (M+1).

EXAMPLE 25

1-Cyclopropyl-6,8-difluoro-5-methyl-1,4-dihydro-7-(4'-hydroxy-3'-aminomethylpiperidin-1-yl)-4-oxo-quinoline-3-carboxylic acid It was prepared in a similar manner as described in example 24 where 4-hydroxy-3-aminomethylpiperidine was used in place of cis-4-amino-3,5-dimethylpiperidine. Yield 42%, m.p 270–75° C., $C_{20}H_{23}F_2N_3O_4$, m/z 408 (M+1).

EXAMPLE 26

5-Amino-1-cyclopropyl-6,8-difluoro-1,4-dihydro-7-(5'-amino-2'-methyl-pyrrolidin-1-yl)-4-oxo-quinoline-3-carboxylic acid The condensation of 5-amino-1-cyclopropyl-6,7,8-trifluoro-1,4-dihydro-4-oxo-quinoline-3-carboxylic acid with 5-amino-2-methyl-pyrrolidine in a similar manner as described in example 1 gave the titled product. Yield 40%, m.p 224–30° C., $C_{18}H_{20}F_2N_4O_3$, m/z 379. (M+1)

EXAMPLE 27

5-Amino-1-cyclopropyl-6,8-difluoro-1,4-dihydro-7-{3'-(L-Ala-L-Ala amino)pyrrolidin-1-yl}-4-oxo-quinoline-3-carboxylic acid It was prepared in a similar manner as described in example 26 where 3-(L-Ala-L-Ala amino)pyrrolidine was used in place of 5-amino-2-methyl-pyrrolidine. Yield 50%, m.p 234–36° C., $C_{23}H_{27}F_2N_6O_5$, m/z 506. (M+1)

EXAMPLE 28

5-Amino-1-cyclopropyl-6,8-difluoro-1,4-dihydro-7-{4'-(N-di-n-butylamino)piperidin-1-yl}-4-oxo-quinoline-3-carboxylic acid It was prepared in a similar manner as described in example 26 where 4-(N-di-n-butylamino)piperidine was used in place of 5-amino-2-methyl-pyrrolidine. Yield (63%), m.p >320° C., $C_{26}H_{36}F_2N_4O_3$, m/z 491. (M+1)

EXAMPLE 29

5-Amino-1-cyclopropyl-6,8-difluoro-1,4-dihydro-7-{4'-(-t-butoxycarbonylamino-L-Ala-L-Ala)aminopiperidin-1-yl}-4-oxo-quinoline-3-carboxylic acid A mixture of 5-Amino-1-cyclopropyl-6,8-difluoro-1,4-dihydro-7-{4-aminopiperidin-1-yl}-4-oxo-quinoline-3-carboxylic acid (200 mg, 0.52 mmole), t-butoxycarbonylamino-L-Ala-L-Ala (134 mg, 0.52 mmole) and 2-Ethoxy-N-ethoxycarbonyl-1,2-dihydroquinoline (EEDQ) (128 mg 0.52 mmole) in dry methylene dichloride for 2 hr, washed with water (10 ml) and organic layer was separated, dried over $Na_2SO_4$ and concentrated to give titled product. Yield 54%, m.p 164–68° C., $C_{29}H_{39}F_2N_6O_7$, m/z 622 (M+1).

EXAMPLE 30

5-Amino-1-cyclopropyl-6,8-difluoro-1,4-dihydro-7-(4'-propionoxypiperidin-1-yl)-4-oxo-quinoline-3-carboxylic acid It was prepared in a similar manner as described in example 26 where 4-propionoxypiperidine where was used in place of 5-amino-2-methyl-pyrrolidine.

Yield 46%, m.p 224–26° C., $C_{21}H_{23}F_2N_3O_5$, m/z 436. (M+1)

EXAMPLE 31

5-Amino-1-cyclopropyl-6,8-difluoro-1,4-dihydro-7-(4'-hydroxy-3',3'-dimethyl-piperidin-1-yl)-4-oxo-quinoline-3-carboxylic acid It was prepared in a similar manner as described in example 26 where 4-hydroxy-3,3-dimethylpiperidine was used in place of 5-amino-2-methyl-pyrrolidine Yield 71%, m.p 236–38° C., $C_{20}H_{23}F_2N_3O_4$, m/z 408. (M+1)

EXAMPLE 32

5-Amino-1-cyclopropyl-6,8-difluoro-1,4-dihydro-7-{4'-(1-pyrrolidinyl)piperidin-1-yl)-4-oxo-quinoline-3-carboxylic acid It was prepared in a similar manner as described in example 26 where 4-(1-pyrrolidinyl)piperidine was used in place of 5-amino-2-methyl-pyrrolidine Yield 59%, m.p 224–26° C., $C_{22}H_{26}F_2N_4O_3$, m/z 433. (M+1)

EXAMPLE 33

5-Amino-1-cyclopropyl-6,8-difluoro-1,4-dihydro-7-4'-[N-(piperidin-4-yl)aminomethyl]-piperidin-1-yl}-4-oxo-quinoline-3-carboxylic acid It was prepared in a similar manner as described in example 26 where 4-[N-(piperidin-4-yl)aminomethyl]piperidine was used in place of 5-amino-2-methyl-pyrrolidine.

Yield 60%, m.p 300(d) ° C., $C_{24}H_{31}F_2N_5O_3$, m/z 476. (M+1)

EXAMPLE 34

5-Amino-1-cyclopropyl-6,8-difluoro-1,4-dihydro-7-{N-1-2',2',6',6'-pentamethyl]piperidin-4-yl)methylamino-4-oxo-quinoline-3-carboxylic acid and its salt It was prepared in a similar manner as described in example 26 where amino-[N-1,N-4-2,2,6,6-hexamethyl]piperidine was used in place of 5-amino-2-methyl-pyrrolidine.

Yield 41%, m.p 200–02° C., $C_{24}H_{32}F_2N_4O_3$, m/z 463. (M+1)

EXAMPLE 35

5-Amino-1-cyclopropyl-6,8-difluoro-1,4-dihydro-7-(3',5'-dimethylmorpholin-1-yl)-4-oxo-quinoline-3-carboxylic acid It was prepared in a similar manner as described in example 26 where 3,5-dimethylmorpholine was used in place of 5-amino-2-methyl-pyrrolidine. Yield 30%, m.p 286–88° C., $C_{19}H_{21}F_2N_3O_4$, m/z 412. (M+1)

EXAMPLE 36

5-Amino-1-cyclopropyl-6,8-difluoro-1,4-dihydro-7-(4'-cyclopropylpiperazin-1-yl)-4-oxo-quinoline-3-carboxylic acid It was prepared in a similar manner as described in example 26 where 4-cyclopropylpiperazine was used in place of 5-amino-2-methyl-pyrrolidine Yield 46%, m.p 260 (d) ° C., $C_{20}H_{22}F_2N_4O_3$, m/z 485. (M+1)

EXAMPLE 37

5-Amino-1-cyclopropyl-6,8-difluoro-1,4-dihydro-7-(3',5'-dimethyl-4-pivaloylpiperazin-1-yl)-4-oxo-quinoline-3-carboxylic acid It was prepared in a similar manner as described in example 26 where 3,5-dimethyl-4-pivaloylpiperazine was used in place of 5-amino-2-methyl-pyrrolidine. Yield 30%, m.p 290–94° C., $C_{24}H_{25}F_2N_4O_4$, m/z 472 (M+1).

EXAMPLE 38

Ethyl 6,8-Difluoro-7-(4-hydroxypiperidin-1-yl)-1-(1-phenylthio-3(S)-but-3-yl)-1,4-dihydro-4-oxo-quinoline-3-carboxylate A mixture of ethyl 6,7,8-trifluoro-1-(1-phenylthio-3(S)-but-3-yl)-1,4-dihydro-4-oxo-quinoline-3-carboxylate (100 mg, 0.229 mmol), 4-hydroxypiperidine (46 mg, 0.45 mmol) and driethylamine (46 mg, 0.45 mmol) was stirred in acetonitrile (5.0 ml) at 85° C. (bath temperature) for 12 h. After completion of the reaction (monitored by tlc), the solvent was evaporated under reduced pressure. Diluted with water (20 ml) and extracted with chloroform (3×30 ml) and evaporated to give the crude product, which on silica gel column purification using 5% MeOH in chloroform gave 100 mg (84%) of the product as viscous liquid. $^1$H NMR (200 MHz, CDCl$_3$): δ 1.40 (t, J=7.0 Hz, 3H, —CH$_2$CH$_3$), 1.60 (d, J=6.0 Hz, 3H, —CHCH$_3$), 1.65–1.81 (m, 4H, 2×—CH$_2$), 1.95–2.15 (4H, 2×—CH$_2$—), 2.70 (quint., 1H, H—C2'), 2.90 (quint, 1H, H—C2'), 3.09–3.10 (m, 2H, —CH$_2$S—), 3.08–3.98 (m, 1H, —CHOH), 4.39 (q, 2H, —CH$_2$CH$_3$), 5.20–5.39 (m, 1H, —CHCH$_3$), 7.20 (s, 5H, arom), 7.95 (dd, J=12.5, 2.0 Hz, 1H, H—C5), 8.45 (s, 1H, H—C2); (ESMS m/z 517 (MH$^+$, 100%).

EXAMPLE 39

1-(2'-Trifluoromethylphenyl)-6-fluoro-1,4-dihydro--7-(3',3',4'-trimethylpiperazin-1-yl)-4-oxo-quinoline-3-carboxylic acid The condensation of with 1-(2'-trifluoromethylphenyl)-6,7-difluoro-1,4-dihydro-4-oxo-quinoline-3-carboxylic acid 3,3,4-trimethylpiperazine in a similar manner as described in example 1 gave the titled product. Yield 24%, m.p 238–42° C., $C_{24}H_{23}F_4N_3O_2$, m/z 478. (M+1)

EXAMPLE 40

5-Amino-1-(2'-trifluoromethylphenyl)-6,8-difluoro-1,4-dihydro-7-(morpholin-1-yl)-4-oxo-quinoline-3-carboxylic acid The condensation of 5-amino-1-(2'-trifluoromethylphenyl)-6,7,8-trifluoro-1,4-dihydro-4-oxo-quinoline-3-carboxylic acid with morpholine in a similar manner as described in example 1 gave the titled product. Yield 52%, m.p 228–30° C., $C_{21}H_{16}F_5N_3O_4$, m/z 470. (M+1)

EXAMPLE 41

5-Amino-1-(2'-trifluoromethylphenyl)-6,8-difluoro-1,4-dihydro-7-(3',5'-dimethylmorpholin-1-yl)-4-oxo-quinoline-3-carboxylic acid It was prepared in a similar manner as described in example 39 where 3,5-dimethylmorpholine was used in place morpholine. Yield 49%, m.p 270–72 ° C., $C_{23}H_{20}F_5N_3O_4$, m/z 498. (M+1)

EXAMPLE 42

5-Amino-1-(2'-trifluoromethylphenyl)-6,8-difluoro-1,4-dihydro-7-(3',5'-dimethylpiperizine-1-yl)-4-oxo-quinoline-3-carboxylic acid It was prepared in a similar manner as described in example 39 where 3,5-dimethylpiperazine was used in place of morpholine. Yield 60%, m.p 190(d) ° C., $C_{23}H_{21}F_5N_4O_3$, m/z 497. (M+1)

EXAMPLE 43

5-Amino-1-(4'-trifluoromethylphenyl)-6,8-difluoro-1,4-dihydro-7-(3'-aminopyrrolidin-1-yl)-4-oxo-quinoline-3-carboxylic acid It was prepared in a similar manner as described in example 39 where 3-aminopyrrolidine was used in place of morpholine. Yield 50%, m.p 258–60° C., $C_{21}H_{17}F_5N_4O_3$, m/z 469 (M+1).

EXAMPLE 44

1-(4'-Fluorophenyl)-6-fluoro-1,4-dihydro-7-{4'-ethylamino)piperidin-1-yl)-4-oxo-quinoline-3-carboxylic acid The condensation of 1-(4'-fluorophenyl)-6,7-difluoro-1,4-dihydro-4-oxo-quinoline-3-carboxylic acid with 4-ethylaminopiperidine in a similar manner as described in example 1 gave the titled product. Yield 51%, m.p 270–72° C., $C_{23}H_{23}F_2N_3O_3$, m/z 428. (M+1)

EXAMPLE 45

1-(2',4'-Difluorophenyl)-6-fluoro-1,4-dihydro-7-(3',5'-dimethylpiperidin-1-yl)-4-oxo-quinoline-3-carboxylic acid The condensation of with 1-(2',4'-difluorophenyl)-6,7-difluoro-1,4-dihydro-4-oxo-quinoline-3-carboxylic acid with 3,5-dimethylpiperidine in a similar manner as described in example 1 gave the titled product. Yield 43%, m.p 224–26° C., $C_{23}H_{21}F_3N_2O_3$, m/z 431. (M+1)

EXAMPLE 46

5-Amino-1-(2',4'-difluorophenyl)-6,8-difluoro-1,4-dihydro-7-(3'-hydroxy-5'-methylpyrrolidin-1-yl)-4-oxo-quinoline-3-carboxylic acid The condensation of 5-Amino-1-(2',4'-difluorophenyl)-6,7,8-trifluoro-1,4-dihydro-4-oxo-quinoline-3-carboxylic acid with 3-hydroxy-5-methylpyrrolidine in a similar manner as described in example 1 gave the titled product. Yield 64%, m.p ° C., $C_{21}H_{17}F_4N_3O_4$, m/z 453. (M+1)

EXAMPLE 47

5-Amino-1-(2',4'-difluorophenyl)-6,8-difluoro-1,4-dihydro-7-(3',3'-dimethylpiperazin-1-yl)-4-oxo-quinoline-3-carboxylic acid It was prepared in a similar manner as described in example 45 where 3,3-dimethylpiperazine was used in place of 3-hydroxy-5-methylpyrrolidine. Yield 41%, m.p 212–14° C., $C_{22}H_{20}F_4N_4O_3$. m/z 465. (M+1)

EXAMPLE 48

1-Cyclopropyl-6-fluoro-1,4-dihydro-7-{(3'-aminoethoxycarbonyl)pyrrolidin-3-yl}-4-oxo-naphthyridine-3-carboxylic acid 1-cyclopropyl-6,7-difluoro-1,4-dihydro-4-oxo-naphthyridine-3-carboxylic acid (0.1 g, 0.32 mmole) and (3-N-ethoxycarbonyl)aminopyrrolidine (0.14 g, 14 mmole) in acetonitril (5 ml) was stirred at 80° C. for 4 hr and cooled. Solvent was concentrated to dryness. Water (25 ml) was added to reaction mixture and solid obtained was purified to give the required product. Yield 23%, m.p. 254–56° C., $C_{19}H_{21}FN_4O_5$, m/z 406. (M+1)

EXAMPLE 49

1-Cyclopropyl-6-fluoro-1,4-dihydro-7-(pyrrolidin-3-yl-amino)-4-oxo-1,8naphthyridine-3-carboxylic acid It was prepared in a similar manner as described in example 47 where 3-aminopyrrolidin was used in place of (3-N-ethoxycarbonyl)aminopyrrolidine. Yield 42%, m.p 122–24° C., $C_{16}H_{17}FN_4O_3$, m/z 333. (M+1)

EXAMPLE 50

1-(2',4'-Difluorophenyl)-6-fluoro-1,4-dihydro-7-(piperidin-4-yl-amino)-4-oxo-1,8-naphthyridine-3-carboxylic acid Ethyl 1-(2,4-difluorophenyl)-6,7-difluoro-1,4-dihydro-4-oxo-naphthyridine-3-carboxylate (0.5 g, 1.3 mmole) and (3-N-ethoxycarbonyl)aminopyrrolidine (0.3 g, 1.74 mmole) in acetonitril (5 ml) was stirred at 80° C. for 3 hr and cooled. Solvent was concentrated to dryness and 5% aqueous NaOH (10 ml) was added to reaction mixture and stirred for 2 hr, acidified with conc. HCl solid separated was filtered, dried to furnish the required product. Yield 74%, m.p >320° C., $C_{20}H_{17}F_3N_4O_3$, m/z 419. (M+1)

EXAMPLE 51

Ethyl-1-(2',4'-difluorophenyl)-6-fluoro-1,4-dihydro-7-{[1α,5α,6α]-3-N-benzyl-3-azabicyclo[3.1.01]hex-6-yl-amino}-4-oxo-1,8-naphthyridine-3-carboxylate and its salt Ethyl 1-(2,4-difluorophenyl)-6,7-difluoro-1,4-dihydro-4-oxo-naphthyridine-3-carboxylate (2 g, 5.2 mmole) and 6-amino-(1α,5α,6α)-3-N-benzyl-3-azabicyclo[3.1.0]hexane (1.16 g, 5.1 mmole) in acetonitrile (5 ml) was stirred at 80° C. for 3 hr and cooled. Solvent was concentrated to dryness and added water (15 ml), solid separated was filtered, dried to furnish the required product. Yield 36%, m.p 187–90° C., $C_{29}H_{25}F_3N_4O_3$, mz 535. (M+1)

EXAMPLE 52

Ethyl 6-fluoro-7-[1-Phenyl-4,5,6,7-tetrahydropyrazolo[4.3-c]pyridin-1-yl]-1-(2,4-difluorophenyl)-4-oxo-1,4-dihydro-1,8-naphthyridine-3-carboxylate A mixture of trova core (500 mg, 1.30 mmol), 4-hydroxypiperidine (200 mg, 1.30 mmol) and triethylamine (260 mg, 2.61 mmol) was stirred in acetonitrile (5.0 ml) at 85° C. (bath temperature) for 6 h. After completion of the reaction (monitored by tlc), the solvent was evaporated under reduced pressure. Diluted with water (20 ml) and extracted with chloroform (3×30 ml) and evaporated to give the crude product, which on silica gel column purification using 5% MeOH in chloroform gave titled product as a yellowish solid. Yield 70%, m.p 85–90° C., ESMS m/z 546 (MH$^+$, 100%).

EXAMPLE 53

(S)-(−)-9-Fluoro-6,7-dihydro-8-(4'-carboxamidopineridin-1-yl)-5-methyl-1-oxo-1H,5H-benzo[i,j]quinolizine-2-carboxylic acid (O-B)-diacetoxy-{S-(−)-8,9-difluoro-5-methyl-6,7-dihydro-1-oxo-1H,5H-benzo[i,j]quinolizine-2-carboxylic acid}borane was heated with 4-carboxamidopiperdine in acetonitile for 6 hr solvent was removed and borate complex was decomposed using 10 ml of 5% aqueous NaOH and stirred for 2 hr, acidified with conc. HCl. Solid separated was filtered, dried and purified on silica column to furnish required product. Yield 34%, m.p 0C, $C_{20}H_{22}FN_3O_4$, m/z 388 (M+1).

EXAMPLE 54

(S)-(−)-9-Fluoro-6,7-dihydro-8-(4'-hydroxypiperidin-1-yl)-5-methyl-1-oxo-1H,5H-benzo[i,j]quinolizine-2-carboxylic acid L-aryinine salt To a stirred suspension of (S)-(−)-9-Fluoro-6,7-dihydro-8-(4'-hydroxypiperidin-1-yl)-5-methyl-1-oxo-1H,5H-benzo[i,j]quinolizine-2-carboxylic acid (5 g, 0.0138 m) in acetone (50 ml) was added finely powdered L-arginine (2.51 g, 0.0138 m) then distilled water (20 ml) was added to it. Reaction mixture was warmed on water bath and two times water (5 ml) was added to it at the interval of 10 min. Clear solution was stirred for 1 hr. Solvent was removed under high vacuum and solid was dried overnight under high vacuum to furnish title product. Yield 96%, m.p 234–37° C., $C_{25}H_{35}FN_6O_6$, m/z) 535. (M+1)

EXAMPLE 55

S-(−)-9-Fluoro-6,7-dihydro-8-(4'-hydroxy-3',3'-dimethylpiperidin-1-yl)-5-methyl-1-oxo-1H,5H-benzo[i,j]quinolizine-2-carboxylic acid It was prepared in a similar manner as described in example 51 where 4-hydroxy-3,3-dimethylpiperidine was used in place 4-carboxamidopiperdine. Yield 42%, m.p 220° C., $C_{21}H_{25}FN_2O_4$, m/z 389. (M+1)

EXAMPLE 56

(S)-(−)-N-methylpiperidino-9-fluoro-6,7-dihydro-8-(4'-hydroxypiperidin-1-yl)-5-methyl-1-oxo-1H,5H-benzo[i,j]quinolizine-2-carboxylic acid A mixture of (S)-(−)-9-fluoro-6,7-dihydro-8-(4'-hydroxypiperidin-1-yl)-5-methyl-1-oxo-1H,5H-benzo[i,j]quinolizine-2-carboxylic acid a (0.5 g, 1.38 mmole), N,N-dimethylaminopyridine (0.203 g, 1.66 mmole), N,N-dicyclohexylcarbodiimde (0.286 g, 1.38 mmole), triethylamine (0.2 ml, 1.9 mmole), N-methyl-4-hydroxypiperidine (0.192 g, 1.66 mmole) were dissolved in N,N-dimethylacetamide (20 ml) stirred at 100° C. for 24 hr. Reaction mixture was cooled to room temp. and diluted with ethyl acetate (50 ml). Washed with 0.5N HCl and sat. NaHCO$_3$. Organic layer was dried over Na$_2$SO$_4$. Solvent removed and solid obtained was purified over silica column to furnish title product. Yield 56%, m.p 170–75° C., $C_{25}H_{32}FN_3O_4$, m/z 458. (M+1)

EXAMPLE 57

Ethoxy carbonylmethyl (R)-(+)-9-fluoro-6,7-dihydro-8-(4'-hydroxypiperidin-1-yl)-5-methyl-1-oxo-1H,5H-benzo[i,j]quinolizine-2-carboyxlate A mixture of (R)-(+)-9-fluoro-6,7-dihydro-8-(4'-hydroxypiperidin-1-yl)-5-methyl-1-oxo-1H,5H-benzo[i,j]quinolizine-2-carboxylic acid (0.5 g, 1.388 mmole) and anhydrous K$_2$CO$_3$ (0.192 g, 1.39 mmole) was suspended in dry N,N-dimethylformamide (20 ml) stirred at 50° C. for 7 hr. Ethylbromoacetate (0.35 g, 2.08 mmole) was added and reaction mixture was stirred for 17 hr. Solvent was removed and extracted with chloroform (25 ml×2). Organic layer was dried and solid obtained was crystallized from chloroform: hexane (2:8) to furnish title product. Yield 71%, m.p 130–35° C., $C_{23}H_{27}FN_2O_6$, m/z 447. (+1)

EXAMPLE 58

(S)-(−)-Morpholinoethyl-9-fluoro-6,7-dihydro-8-(4'-hydroxypiperidin-1-yl)-5-methyl-1-oxo-1H,5H-benzo[i,j]quinolizine-2-carboxylic acid A mixture of (S)-(−)-9-fluoro-6,7-dihydro-8-(4'-hydroxypiperidin-1-yl)-5-methyl-1-oxo-1H,5H-benzo[i,j]quinolizine-2-carboxylic acid a (0.5 g, 1.38 mmole), N,N-dimethylaminopyridine (0.203 g, 1.66 mmole), N,N-dicyclohexylcarbodiimde (0.286 g, 1.38 mmole), triethylamine (0.2 ml, 1.9 mmole), N-(2-hydroxyethyl)morpholine (0.218 g, 1.66 mmole) were dissolved in N,N-dimethylacetamide (20 ml) stirred at 100° C. for 24 hr. Reaction mixture was cooled to room temp. and diluted with ethyl acetate (50 ml). Washed with 0.5N HCl and sat. NaHCO$_3$. Organic layer was dried over Na$_2$SO$_4$. Solvent removed and solid obtained was purified over silica column to furnish title product. Yield 58%, m.p 245–50° C., $C_{25}H_{32}FN_3O_5$, m/z 474. (M+1)

Some Preferred Compounds of the Invention Displaying Inhibition of the Efflux Pumps of *Pseudomonas aerueinosa* 23587 and *E. coli* 2051

EXAMPLE 1

1-Cyclopropyl-6-fluoro-1,4-dihydro-5-methyl-7-(4'-methoxypiperidin-1-yl)-4-oxo-quinoline-3-carboxylic acid A mixture of 1-cyclopropyl-6,7-difluoro-1,4-dihydro-5-methyl--4-oxo-quinoline-3-carboxylic acid (500 mg, 1.3 mmole), 4-methoxypiperidin-1-yl (600 mg, 5 mmole) and triethylamine (0.2 ml) in DMSO (5 ml) was stirred at 140° C. for 24 hr and cooled. Solvent was concentrated to dryness triturated with water (25 ml) solid thus separated was filtered and dried to furnish the required product. Yield 57%, m.p 130–38° C., $C_{20}H_{23}FN_2O_4$, m/z 375 (M+1).

EXAMPLE 2

7-Bromo-1-cyclopropyl-6-fluoro-5-methyl-11 4-dihydro-4-oxo-quinoline-3-carboxylic acid and its salts The preparation of the compound is described in PCT WO 89/06649.

EXAMPLE 3

1-Cyclopropyl-6-fluoro-8-methoxy-1,4-dihydro-7-(4'-amino-3'-methylpiperidin-1-yl)-4-oxo-quinoline-3-carboxylic acid A mixture of [1-cyclopropyl-6,7-difluoro-1,4-dihydro-8-methoxy-4-oxo-quinoline-3-carboxylate-$O^3,O^4$]difluoroboron chelate (0.1 g, 0.29 mmole) and 4-amino-3-methylpiperidine (0.2 g, 1.75 mmole) in acetonitrile (20 ml) was refluxed for 6 hr. The reaction mixture was concentrated to dryness. The obtained residue was treated with triethylamine (3 ml) and ethanol (15 ml) and refluxed for 16 hr. The resulting mixture was concentrated to dryness; the solid thus obtained was triturated with water (10 ml), filtered, washed with water, dried and purified by preparative HPLC to furnish the required product. Yield 0.04 g (35%), m.p. 238–40° C., $C_{20}H_{24}FN_3O_4$, m/z 390 (M+1), PMR (CD$_3$OD): 0.84–1.42 (7H, m, 2×CH$_2$ & CH$_3$), 1.8–2.4 (3H, m, CH & CH$_2$), 3.02 (1H, m, N—CH), 3.18–3.72 (4H, m, 2×N—CH$_2$), 3.8 (3H, S, OCH$_3$), 4.18 (1H, m, c-CH), 7.82 (1H, d, H-5, J=16 Hz), 8.9 (1H, s, H-2).

EXAMPLE 4

5-Amino-1-cyclopropyl-6-fluoro-8-methoxy-1,4-dihydro-7-(4'-amino-3'-methylpiperidin-1-yl)-4-oxo-quinoline-3-carboxylic acid The condensation of 5-amino-1-cyclopropyl-6,7-difluoro-8-methoxy -1,4-dihydro-4-oxo-quinoline-3-carboxylic acid with 4-amino-3-methylpiperidine was carried out in a similar manner as described in example 1, gave the titled product. Yield 50%, m.p 260–62° C., $C_{20}H_{25}FN_4O_4$, m/z 405 (M+1).

EXAMPLE 5

5-Amino-1-cyclopropyl-6-fluoro-8-methoxy-1,4-dihydro-7-{3',3'-dimethyl-4'-ethylaminopiperidin-1-yl}-4-oxo-quinoline-3-carboxylic acid It was prepared in a similar manner as described in example 4 where 4-ethylamino-3,3-dimethylpiperidine was used in place of 4-amino-3-methylpiperidine. Yield 54%, m.p 205° C., $C_{23}H_{31}FN_4O_4$, m/z 447 (M+1).

EXAMPLE 6

1-Cyclopropyl-6-fluoro-8-methoxy-1,4-dihydro-7-(4'-amino-3'-3'-dimethylpiperidin-1-yl)-4-oxo-quinoline-3-carboxylic acid 1-cyclopropyl-6-fluoro-1,4-dihydro-8-methoxy-7-4'-N-benzyloxycarbonyl-amino-3',3'-dimethylpiperidin-1-yl}-4-oxo-quinoline-3-carboxylic acid (5.5 g, 9.3 mmole) was stirred with Conc. HCl (75 ml) for 2 hr at 30° C., concentrated to dryness, triturated with acetone and filtered. The obtained hydrochloride was dissolved in water-methanol, neutralized with triethylamine (2 ml), concentrated and crystalfisation from methanol furnished the required product. Yield 3.8 g (31%), m.p. 256–58° C., $C_{21}H_{26}FN_3O_4$, m/z 404 (M+1), It was prepared in a similar manner as described in Example 3, where 4-amino-3,3-dimethylpiperidine was used in place of 4-amino-3-methylpiperidine. Yield 0.24 g (10%), m.p. 258–60° C., $C_{21}H_{26}FN_3O_4$, m/z 404 (M+1).

EXAMPLE 7

1-Cyclopropyl-6-fluoro-8-methoxy-1,4-dihydro-7-{4'-dimethylaminopiperidin-1-yl}-4-oxo-quinoline-3-carboxylic acid The preparation of the compound is described in U.S. Pat. No. 4,822,801

EXAMPLE 8

1-Cyclopropyl-6-fluoro-8-methoxy-1,4-dihydro-7-(4'-hydroxy-4'-methylpiperidin-1-yl)-4-oxo-quinoline-3-carboxylic acid It was prepared in a similar manner as described in example 19 (NorA), where 4-hydroxy-4-methylpiperidine was used in place of 4-dimethylamino-3-methylpiperidine Yield 35%, m.p 220–24° C., $C_{20}H_{23}FN_2O_5$, m/z 390 (M+1).

EXAMPLE 9

1-Cyclopropyl-6-fluoro-8-methoxy-1,4-dihydro-7-(3',3'-dimethyl-4'-hydroxy-piperidin-1-yl)-4-oxo-quinoline-3-carboxylic acid It was prepared in a similar manner as described in example 19 (NorA), where 4-hydroxy-3,3-dimethylpiperidine was used in place of 4-eimethylamino-3-methylpiperidine Yield 56%, m.p 240–42° C., $C_{21}H_{25}FN_2O_5$, m/z 404 (M+1).

EXAMPLE 10

1-Cyclopropyl-6,8-difluoro-5-methyl-1,4-dihydro-7-(3'-aminomethyl-4'-hydroxy-piperidin-1-yl)-4-oxo-quinoline-3-carboxylic acid The condensation of 1-cyclopropyl-6,7,8-trifluoro-5-methyl-1,4-dihydro-4-oxo-quinoline-3-carboxylic acid with 3-aminomethyl-4-hydroxy-piperidine was carried out in a similar manner as described in example 1 gave the titled product. Yield 45.9%, m.p 270–75° C., $C_{20}H_{23}F_2N_3O_4$, m/z 408 (M+1).

EXAMPLE 11

5-Amino-1-(cyclopropyl)-6,8-difluoro-1,4-dihydro-7-(3'-aminomethyl-4'-hydroxy-piperidin-1-yl)-4-oxo-quinoline-3-carboxylic acid The condensation of 5-amino-1-cyclopropyl-6,7,8-trifluoro-1,4-dihydro-4-oxo-quinoline-3-carboxylic acid with 3-aminomethyl-4-hydroxy-piperidine was carried out in a similar manner as described in example 1, gave the titled product. Yield 52.8%, m.p 202–04° C., $C_{19}H_{22}F_2N_4O_4$, m/z 409 (M+1).

EXAMPLE 12

1-Ethyl-6,8-difluoro-1,4-dihydro-7-(3'-5'-dimethylpiperazin-1-yl)-4-oxo-quinoline-3-carboxylic acid The condensation of 1-ethyl-6,7,8-trifluoro-1,4-dihydro-4-oxo-quinoline-3-carboxylic acid with 3-5-dimethylpiperazine was carried out in a similar manner as described in example 1, gave the titled product. Yield 58%, m.p 230° C. (d), $C_{18}H_{22}F_2N_3O_3$, m/z 367 (M+1).

EXAMPLE 13

1-Cyclopropyl-6-fluoro-1,4-dihydro-7-(4'-ethyl-3'-methylpiperazin-1-yl)-4-oxo-quinoline-3-carboxylic acid The condensation of 1-cyclopropyl-6,7-difluoro-1,4-dihydro-4-oxo-quinoline-3-carboxylic acid with 4-ethyl-3-methylpiperazine was carried out in a similar manner as described in example 1 gave the titled product. Yield 51%, m.p 200° C., $C_{20}H_{24}FN_3O_3$, m/z 374 (M+1).

EXAMPLE 14

1-Cyclopropyl-6-fluoro-1,4-dihydro- -7-(3'-5'-dimethyl-4'-ethylpiperazin-1-yl)-4-oxo-quinoline-3-carboxylic acid It was prepared in a similar manner as described in example 13, where 3–5-dimethyl-4-ethylpiperazine was used in place of 4-ethyl-3-methylpiperazine. Yield 79%, m.p 215–20° C., $C_{21}H_{26}FN_3O_3$, m/z 388 (M+1).

EXAMPLE 15

1-Ethyl-6,8-difluoro-1,4-dihydro-7-[(1α,5α,6α)-6'-amino-3'-azabicyclo[3.1.01]hex-3-yl}-oxo-quinoline-3-carboxylic acid The condensation of (1α,5α,6α)-6-t-butoxycarbonylamino-3-azabicyclo[3.1.0]-hexane with 1-ethyl-6,7,8-trifluoro-1,4-dihydro-4-oxo-quinoline-3-carboxylic acid was carried in similar manner as described in example 1, which on hydrolysis with conc. HCl furnished titled product. Yield 22.4%, m.p 2243–26° C., $C_{17}H_{17}F_2N_3O_3$, m/z 350 (M+1).

EXAMPLE 16

5-Amino-1-(2',4'-difluorophenyl)-6,8-difluoro-1,4-dihydro-7-(3-aminopyrrolidine -1-yl)-4-oxo-quinoline-3-carboxylic acid The condensation of 5-amino-1-(2',4'-difluorophenyl)-6,7,8-trifluoro-1,4-dihydro-4-oxo-quinoline-3-carboxylic acid with 3-aminopyrrolidine was carried out in a similar manner as described in example 1, gave the titled product. Yield 71%, m.p 268° C. (d), $C_{20}H_{16}F_4N_4O_3$, m/z 437 (M+1).

EXAMPLE 17

5-Amino-1-cyclopropyl-6,8-difluoro-1,4-dihydro-7-{(3'-amino ethoxycarbonylpyrrolidin-3-yl)-4-oxo-quinoline-3-carboxylic acid The condensation of 5-amino-1-cyclopropyl-6,7,8-trifluoro-1,4-dihydro-4-oxo-quinoline-3-carboxylic acid was carried out with 3-amino ethoxycarbonylpyrrolidine in a similar manner as described in example 1 gave the titled product. Yield 68.3%, m.p 180–84° C., $C_{20}H_{21}F_2N_4O_5$, m/z 437 (M+1).

EXAMPLE 18

1-Cyclopropyl-6-fluoro-1,4-dihydro-7-(pyrrolidin-3'-ylamino)-4-oxo-naphthyridine-3-carboxylic acid.

Prepared according to example 48 in the list of compounds for the NorA pump.

EXAMPLE 19

1-(2',4'-Difluorophenyl)-6-fluoro-1,4-dihydro-7-(piperidin-4'-ylamino)-4-oxo-naphthyridine-3-carboxylic acid Prepared according to example 49 in the list of compounds for the NorA pump.

EXAMPLE 20

1-Cyclopropyl-6-fluoro-1,4-dihydro-7-(4'-amino-3'-ethylpiperidin-1-yl)-4-oxo-naphthyridine-3-carboxylic acid The condensation of 1-cyclopropyl-6,7-difluoro-1,4-dihydro-4-oxo-naphthyridine-3-carboxylic acid with 4-amino-3-ethylpiperidine was carried out in acetonitrile in a similar manner as described in example 1, gave the titled product. Yield 71%, m.p 218–20° C., $C_{19}H_{23}FN_4O_3$, m/z 375 (M+1).

EXAMPLE 21

S-(−)-9-Fluoro-6,7-dihydro-8-(4'-hydroxypiperidin-1-yl)-5-methyl-1-oxo-1H,5H-benzo[i,j]quinolizine-2-carboxylic acid 0.2 hydrate S-(−)-9-Fluoro-6,7-dihydro-8-(4'-hydroxypiperidin-1-yl)-5-methyl-1-oxo-1H,5H-benzo[i,j]quinolizine-2-carboxylic acid was crystallized from aqueous ethanol to furnish titled product. Yield 75%, m.p 244–46 ° C., $C_{19}H_{21}FN_2O_4$, m/z 361(M+1).

EXAMPLE 22

S-(−)-9-Fluoro-6,7-dihydro-8-(4'-hydroxypiperidin-1-yl)-5-methyl-1-oxo-1H,5H-benzo[i,j]quinolizine-2-carboxylic acid, choline salt S-(−)-9-Fluoro-6,7-dihydro-8-(4'-hydroxypiperidin-1-yl)-5-methyl-1-oxo-1H,5H-benzo[i,j]quinolizine-2-carboxylic acid (0.5 g, 1.388 mmole) was dissolved in methanol (50 ml) to it was added 45% w/w solution of choline base (0.374 ml, 1.388 mmole) and stirred at 50° C. for 5 hr, and concentrated to dryness. Yield 80%, m.p 190–92° C., $C_{24}H_{35}FN_3O_6$, m/z 482 (M+1)

EXAMPLE 23

S-(-9-Fluoro-6,7-dihydro-8-(4'-hydroxypiperidin-1-yl)-5-methyl-1-oxo-1H,5H-benzo[i,j]quinolizine-2-carboxylic acid, 1-hydroxyethylpyrrolidine salt It was prepared according to procedure described in example 22, where 1-hydroxyethylpyrrolidine (0.156 g, 1.388 mmole) was used in place of choline base. Yield 78%, m.p 252° C., $C_{25}H_{33}FN_3O_5$, m/z 476 (M+1).

EXAMPLE 24

S-(−)-9-Fluoro-6,7-dihydro-8-(4'-hydroxypiperidin-1-yl)-5-methyl-1-oxo-1H,5H-benzo[i,j]quinolizine-2-carboxylic acid, diethanolamine salt It was prepared according to procedure described in example 22, where diethanolamine (0.146 g, 1.388 mmole) was used in place of choline base. Yield 57%, m.p 255–60° C., $C_{23}H_3,FN_3O_6$, m/z 466 (M+1)

EXAMPLE 25

(S)-(−)-9-Fluoro-6,7-dihydro-8-(4'-hydroxypiperidin-1-yl)-5-methyl-1-oxo-1H,5H-benzo[i,j]quinolizine-2-carboxylic acid. (L) histidine salt It was prepared according to procedure described in example 22, where L-histidine (0.21 g, 1.38 mmole) was used in place of choline base. Yield 98%, m.p 278–84° C., $C_{31}H_{39}FN_8O_8$, m/z 671 (M+1)

EXAMPLE 26

(RS)-(±)-9-Fuoro-6,7-dihydro-8-{4'-(D-phenylalaninoxy)piperidin-1-yl}-5-methyl-1-oxo-1H,5H-benzo[i,j]quinolizine-2-carboxylic acid hydrochloride (RS)-(±)-9-Fuoro-6,7-dihydro-8-(4-hydroxypiperidin-1-yl)-5-methyl-1-oxo-1H,5H-benzo[i,j]quinolizine-2-carboxylic acid (360 mg, 1 mm), and triethylamine (0.145 ml, 1 mm) are dissolved in dimethylacetamide (15 ml. t-Butyloxycarbonyl (D)-phenylalanine (265 mg, 1 mm) and dimethylaminopyridine (125 mg, 1 mm) were added, followed by dicyclohexyl carbodiimide under ice cooling. Stirred 30 minutes at 0° C. then at room temperature overnight. Dicyclohexylurea was ifiltered and the mixture diluted with ethylacetate, transferred to a separating funnel, washed with 0.5 N HCl, 1N NaHCO$_3$ and brine, dried (Na$_2$SO$_4$) and evaporated to give Boc-aminoacidoxy-Nadifloxacin.

Trifluoroacetic acid (10 ml) was added to the product obtained. Stirred for 30 mins at room temp., the acid was evaporated and the TFA salt of amino acid ester was precipitated by addition of ether. Purified by RP-HPLC on a C18 column. Dissolved the TFA salt in 0.1 N HCl and freeze-dried provided the titled HCl salt. Yield 75%, m.p (hygroscopic) ° C., C$_{23}$H$_{26}$FN$_3$O$_7$, m/z 543 (M+1)

EXAMPLE 27

(RS)-(±)-9-Fluoro-6,7-dihydro-8-4'-(L-ot-aspartyloxy)piperidin-1-yl]-5-methyl-1-oxo-1H,5H-benzo[i,j]quinolizine-2-carboxylic acid hydrochloride It was prepared according to procedure described in example 26, where t-butoxycarbonyl (L)-asparticacid (133 mg, 1 mmole) was used in place t-Butyloxycarbonyl (D)-phenylalanine Yield 90%, m.p (hygroscopic) ° C., C$_{23}$H$_{26}$FN$_3$O$_7$, m/z 671 (M+1)

EXAMPLE 28

(RS)-(+)-9-Fluoro-6,7-dihydro-8-{4'-(L-leucyloxy) piperidin-1-yl}-5-methyl-1-oxo-1H,5H-benzo[i,j] quinolizine-2-carboxylic acid hydrochloride It was prepared according to procedure described in example 26, where t-butoxycarbonyl (L)-asparticacid (131 mg, 1 mmole) was used in place t-Butyloxycarbonyl (L)-leucine. Yield 43%, m.p 166° C., C$_{25}$H$_{32}$FN$_3$O$_5$, m/z 475.5 (M+1)

EXAMPLE 29

(S)-(−)-9-Fluoro-6,7-dihydro-8-{4'-(D-leucyloxy) piperidin-1-yl}-5-methyl-1-oxo-1H,5H-benzo[i,j] quinolizine-2-carboxylic acid hydrochloride It was prepared according to procedure described in example 26, where t-butoxycarbonyl (L)-asparticacid (131 mg, 1 mmole) was used in place t-Butyloxycarbonyl (L)-leucine. Yield 94%, m.p 220–23° C., C$_{25}$H$_{32}$FN$_3$O$_5$, m/z 671 (M+1)

EXAMPLE 30

(S)-(−)-9-Fluoro-6,7-dihydro-8-{4'-(L-alanyloxy) piperidin-1-yl}-5-methyl-1-oxo-1H,5H-benzo[i,j] quinolizine-2-carboxylic acid hydrochloride It was prepared according to procedure described in example 26, where t-butoxycarbonyl (L)-alanine (89 mg, 1 mmole) was used in place t-Butyloxycarbonyl (D)-phenylalainine. Yield 95%, m.p 160–65° C., C$_{22}$H$_{26}$FN$_3$O$_5$, m/z 467.5 (M+1).

EXAMPLE 31

(S)-(−)-Morpholinoethyl-9-fluoro-6,7-dihydro-8-(4'-hydroxypiperidin-1-yl)-5-methyl-1-oxo-1H,5H-benzo[i,j]quinolizine-2-carboxylate Prepared according to example 55 in the list of compounds for the NorA pump.

EXAMPLE 32

(R)-(+)-9,8-fluoro-8-fluoro-6,7-dihydro-5-methyl-1-oxo-1H,5H-benzo[i,j]quinolizine-2-carboxylate Methoxy phe-lys-OMe R-Nadifloxacin (285 mg, 1 mmole), and triethylamine (0.145 ml, 1 mmole) are dissolved in dimethylacetamide (15 ml). Isobutylchloroformate (0.13 ml, 1 mmole) is added under ice cooling, sirred for 5 min, a solution of S-Phe-S-Lysine (2-chlorobenzyloxycarbonyl 1)-methylester TFA (0.6 g, 1 mmole) and triethylamine (0.14 ml, 1 mmole) in DMAC (10 ml) was added followed by dimethylaminopyridene (125 mg, 1 mmole) and the mixture was stirred at room temperature overnight. The mixture was then diluted with ethyl acetate, transferred in a separating funnel, washed with 0.5 N HCl, 1N sodium bicarbonate and brine, dried (Na$_2$SO$_4$) and evaporated to dryness. The above product is dissolved in methanol-acetic acid-water (15–2–2 ml), and chlorobenzyloxycarbonyl protecting group was removed by bubbling hydrogen in presence of Palladium/charcoal. The catalyst was filtered and filtrates evaporated to gave syrup, which solidified on triturating with ether to gave the titled compound. The compound was purified by prep-B:PLC using water-acetonitrile-0.1% TFA system to get after freeze drying a white powder as trifluoro acetate salt. Yield 74%, m.p 80–82° C., C$_{30}$H$_{34}$F$_2$N$_4$O$_5$, m/z 467.5 (M+1).

EXAMPLE 33

(RS)-(+)-9-Fluoro-6,7-dihydro-8-(trans-4'-hydroxy-3'-methylpiperidin-1-yl)-5-methyl-1-oxo-1H,5H-benzo[i,j]quinolizine-2-carboxylic acid (O-B)-diacetoxy-{RS-(±)-8,9-difluoro-5-methyl-6,7-dihydro-1-oxo-1H,5H-benzo[i,j]quinolizine-2-carboxylic acid}borane (471 mg, 1.15 mmole) was heated with trans-4-hydroxy-3-methylpiperidine (400 mg, 3.47 mmole) in acetonitrile (15 ml) for 6 hr, solvent was removed, and borate complex was decomposed using of 5% aqueous NaOH (10 ml) and stirred for 2 hr, acidified with conc. HCl. Solid separated was filtered, dried and purified on silica column to furnish titled product. Yield 66%, m.p 150–52° C., C$_{20}$H$_{23}$FN$_2$O$_4$, m/z 375 (M+1).

EXAMPLE 34

(RS)-(+)-9-Fluoro-6,7-dihydro-8-(cis-4'-hydroxy-3'-methylpiperidin-1-yl}-5-methyl-1H,5H-benzo[i,j] quinolizine-2-carboxylic acid It was prepared according to procedure described in example 33, where cis-4-hydroxy-3-methylpiperidine was used in place of trans-4-hydroxy-3-methylpiperidine. Yield 48%, m.p 146–48° C., C$_{20}$H$_{23}$FN$_2$O$_4$, m/z 375 (M+1).

EXAMPLE 35

S-(−)-9-Fluoro-6,7-dihydro-8-(trans-4'-hydroxy-3'-methylpiperidin-1-yl]-5-methyl-1H,5H-benzo[i,j] quinolizine-2-carboxylic acid It was prepared according to procedure described in example 33, where (O-B)-diacetoxy-(S)-(−)-8,9-difluoro-5-methyl-6,7-dihydro-1-oxo-1H,5H-benzo[i,j]quinolizine-2-carboxylic acid}borane was used in place of OB diacetoxy was used in place of (O-B)-diacetoxy-{RS-(+)-8,9-difluoro- 5-methyl-6,7-dihydro-1-oxo-1H,5H-benzo[i,j]quinolizine-2-carboxylic acid}borane. Yield 42%, m.p 184–86° C., $C_{20}H_{23}FN_2O_4$, m/z 375 (M+1).

EXAMPLE 36

7H-Pyrido[1,2,3-de]-1,4-benzoxazine-9-fluoro-2,3-dihydro-3-methyl-10-(4'-hydroxy-3'-ethylpiperidin-1'-yl)-7-oxo-6-carboxylic acid The condensation of 7H-pyrido[1,2,3-de]-1,4-benzoxazine-9,10-difluoro-2,3-dihydro-3-methyl-7-oxo-6-carboxylic acid with 4-hydroxy-3-ethylpiperidine was carried out in a similar manner as described in example 1, gave the titled product. Yield 86%, m.p 178–80° C., $C_{20}H_{23}FN_2O_5$, m/z 391 (M+1).

EXAMPLE 37

10-Fluoro-11-[(1∝,5∝,6∝)-6-amino-3-azabicyclo[3.1.01]hex-3yl]-3,4-dihydro-4(S)-methyl-8-oxo-2H,8H-pyrido[1,2,3-ef]-1,5-benzoxazipin-7-carboxylic acid. HCl A mixture of 10,11-Difluoro-3,4-dihydro-4(S)-methyl-8-oxo-2H,8H-pyrido[1,2,3-de]-1,5-benzoxazepine-7-carboxylic acid (300 mg, 1.107 mmol), 6-amino-3-azabicyclo[3.1.0] hexane (201 mg, 1.017 mmol) and triethylamine (206 mg, 2.03 mmol) was stirred in acetonitrile (5 ml) at 85° C. for 96 hr. After completion of the reaction (monitored by tlc), the solvent was evaporated under reduced pressure. Diluted with water (20 ml) and extracted with chloroform (4×25 ml). The chloroform extracts were concentrated and the residue was dissolved in 2.0 N HCl (20 ml) and washed with ethyl acetate (2×20 ml) to remove the unreacted material if any. The aqueous layer was filtered and lyophilized to give titled product. Yield 48%, m.p. 200–204° C., $C_{19}H_{21}ClFN_3O_4$, m/z 411 (M+1).

Some Preferred Compounds of the Invention Displaying Inhibition of the Efflux Pumps of *E. coli* 2051

The compounds listed in Table 3 are common with the respective compounds in Table 2. Their preparation is described under the examples for the efflux pump inhibitors described under *Pseudomonas aeruginosa*.

Some preferred Compounds with EPI activity against Mef pumps of *Streptococcus pneumonia* 3514 and *Streptococcus pyoegenes* 26-00

EXAMPLE 1

1-Cyclopropyl-6-fluoro-8-methoxy-1,4-dihydro-7-(4'-amino-3'-methylpiperidin-1-yl)-4-oxo-quinoline-3-carboxylic acid It was prepared as described in example 3 in the list of EPIs active against *Pseudomonas aeruginosa*.

EXAMPLE 2

5-Amino-1-cyclopropyl-6-fluoro-8-methoxy-1,4-dihydro-7-{4'-(methylamino)-3',3'-dimethylpiperidin-1-yl}-4-oxo-quinoline-3-carboxylic acid The condensation of 5-amino-1-cyclopropyl-6,7-difluoro-8-methoxy-1,4-dihydro-4-oxo-quinoline-3-carboxylic acid with 4-methylamino-3,3-dimethylpiperidine was carried out in a similar manner as described in example 1 (NorA), gave the titled product. Yield 54%, m.p 250° C., $C_{22}H_{29}FN_4O_4$, m/z 433 (M+1).

EXAMPLE 3 i-Propyl 1-cyclopropyl-6-fluoro-8-methoxy-1,4-dihydro-7-(4'-amino-3',3'-dimethyl-piperidin-1-yl)-4-oxo-quinoline-3-carboxylate In a dry dimethylformaide (15 ml) was taken a mixture of 1-cyclopropyl-6-fluoro-8-methoxy-1,4-dihydro-7-(4'-t-butoxycarbonylamino-3',3'-dimethylpiperidin-1-yl)-4-oxo-quinoline-3-carboxylic acid (1 g, 1.98 mmole), $K_2CO_3$ (0.275 g, 1.98 mmole) was stirred at 70° C. for 7 hr. Added 1-iodopropane (0.5 g, 2.98 mmole) to reaction mixture and stirred at the same temperature for 16 hr. Solvent was concentrated up to dryness and (15 ml) water was added to it and extracted with chloroform (25 ml×2). Organic layer was separated, dried, concentrated, Which was hydrolysied with trifluoroacetic acid in methylene dichloride and purified on silica column to furnish titled product. Yield 45%, m.p 140–42° C., $C_{24}H_{32}FN_3O_4$, m/z 446 (M+1).

EXAMPLE 4 n-Butyl 1-cyclopropyl-6-fluoro-8-methoxy-1,4-dihydro-7-(4'-amino-3',3'-dimethyl-piperidin-1-yl)-4-oxo-quinoline-3-carboxylate It was in a similar manner as described in example 3, where 1-iodobutane was used in place of 1-iodopropane. Yield 55%, m.p 120–25° C., $C_{25}H_{34}FN_3O_4$, m/z 460 (M+1).

EXAMPLE 5

Ethoxycarbony methyl 1-Cyclopropyl-6-fluoro-8-methoxy-1,4-dihydro-7-(4'-amino-3',3'-dimethylpiperidin-1-yl)-4-oxo-quinoline-3-carboxylate It was in a similar manner as described in example 3, where Bromo ethyl acetate was used in place of 1-iodopropane. Yield 87%, m.p 135–40° C., $C_{25}H_{32}FN_3O_6$, m/z 489 (M+1).

EXAMPLE 6

Benzyl 1-cyclopropyl-6-fluoro-8-methoxy-1,4-dihydro-7-{4-N-t-butoxycarbonyl)-amino-3',3'-dimethylpiperidin-1-yl)-4-oxo-quinoline-3-carboxylate It was in a similar manner as described in example 3, where benzyl bromide was used in place of 1-iodopropane. Yield 67%, m.p 152–54 ° C., $C_{33}H_{40}FN_3O_6$, m/z 594 (+1).

EXAMPLE 7

1-Cyclopropyl-6-fluoro-8-methoxy-1,4-dihydro-7-{4'-N-(t-butoxycarbonyl-L-alanyl)-amino-3',3'-dimethylpiperidin-1-yl}-4-oxo-quinoline-3-carboxylic acid hydrochloride 1-Cyclopropyl-6-fluoro-8-methoxy-1,4-dihydro-7-{4'-amino-3',3'-dimethylpiperidin-1-yl}-4-oxo-quinoline-3-carboxylic acid (1.0 gm, 2.48 mmole), N-t-butoxycarbonyl-(L)-alanine (0.94 gm, 4.96 mmole) and 2-ethoxy-N-ethyoxycarbonyl dihydroquinoline (EEDQ) (061 gm, 2.48 mmole) were dissolved in dichromethane (300 ml) and the mixture is stirred at room temperature for 48 hr. The mixture is washed with water, separate the layer, dried and concentrated. Product purified by silica gel column to furnish titled product. Yield 84%, m.p 170–75° C., $C_{29}H_{39}FN_4O_7$, m/z 575 (M+1).

EXAMPLE 8

1-Cyclopropyl-6-fluoro-8-methoxy-1,4-dihydro-7-(4'-(L)-alaninylamino-3',3'-dimethylpiperidin-1-yl)-4-oxo-quinoline-3-carboxylic acid hydrochloride 1-Cyclopropyl-6-fluoro-8-methoxy-1,4-dihydro-7-{4'-(N-t-butoxycarbonyl-L-alanyl)amino-3',3'-dimethylpiperidin-1-yl}-4-oxo-quinoline-3-carboxylic acid (0.9 gm) is hydrolysed with 6N HCl (20 ml) at room temperature for 1 hr. The mixture concentrated to furnish the titled product. Yield 75%, m.p 245–50° C., $C_{24}H_{31}FN_4O_5$.HCl m/z 475 (M+1).

EXAMPLE 9

1-Cyclopropyl-6-fluoro-8-methoxy-1,4-dihydro-7-(3',3'-dimethyl-4'-N-(t-butoxycarbonyl-L-valyl)-aminopiperidin-1-yl}-4-oxo-quinoline-3-carboxylic acid and its salts 1-Cyclopropyl-6-fluoro-8-methoxy-1,4-dihydro-7-{4'-amino-3',3'-dimethylpiperidin-1-yl}-4-oxo-quinoline-3-carboxylic acid (1.0 gm, 2.48 mmole), N-t-butoxycarbonyl-(L)-valine (1.07 gm, 4.96 mmole) and 2-ethoxy-N-ethyoxycarbonyl dihydroquinoline (EEDQ) (0.61 gm, 2.48 mmole) were dissolved in dichromethane (300 ml) and the mixture is stirred at room temperature for 48 hr. The mixture is washed with water, separate the layer, dried and concentrated. Product purified by silica gel column to furnish titled product. Yield 37%, m.p 80–82° C., $C_{31}H_{43}FN_4O_7$, m/z 603 (+1).

EXAMPLE 10

1-Cyclopropyl-6-fluoro-8-methoxy-1,4-dihydro-7-(3',3'-dimethyl-4'-L-valinylaminopiperidin-1-yl}-4-oxo-quinoline-3-carboxylic acid hydrochloride 1-Cyclopropyl-6-fluoro-8-methoxy-1,4-dihydro-7-{4'-(N-t-butoxycarbonyl-L-valyl)amino-3',3'-dimethylpiperidin-1-yl)-4-oxo-quinoline-3-carboxylic acid (0.4 gm) is hydrolysed with 6N HCl (20 ml) at room temperature for 1 hr. The mixture concentrated to furnish the titled product. Yield 75%, m.p 150–55° C., $C_{26}H_{35}FN_4O_5$.HCl m/z 503 (M+1).

EXAMPLE 11

1-Cyclopropyl-6-fluoro-8-methoxy-1,4-dihydro-7-(4'-(L)-aspartylamino-3',3'-dimethylpiperidin-1-yl}-4-oxo-quinoline-3-carboxylic acid hydrochloride 1-Cyclopropyl-6-fluoro-8-methoxy-1,4-dihydro-7-{4'-amino-3',3'-dimethylpiperidin-1-yl}-4-oxo-quinoline-3-carboxylic acid (1.0 gm, 2.58 mmole), N-Boc-L-aspartic acid (1.15 gm, 4.96 mmole) and 2-ethoxy-N-ethyoxycarbonyl dihydroquinoline (EEDQ) (0.61 gm, 2.48 mmole) were dissolved in dichromethane (300 ml) and the mixture is stirred at room temperature for 48 hr. The mixture is washed with water, separate the layer, dried and concentrated. Which was hydrolysed with 6N HCl at room temperature for 1 hr and concentrate to furnish titled product. Yield 54%, m.p 250–55° C., $C_{25}H_{31}FN_4O_7$.HCl m/z 618 (M+1).

EXAMPLE 12

1-Ethyl-6,8-difluoro-1,4-dihydro-7-(4'-ethylaminouiperidin-1'-yl)-4-oxo-quinoline-3-carboxylic acid and its salts It was prepared in a similar manner as described in example 5 (NorA), where 4-ethylaminopiperidine was used in place of 3-amino-5-methylpyrrolidine. Yield 44%, m.p 260–62° C., $C_{19}H_{24}F_2N_4O_3$, m/z 395 (M+1)

EXAMPLE 13

5-Amino-1-cyclopropyl-6,8-difluoro-1,4-dihydro-7-(4'-amino-3'-methylpiperidin-1-yl)-4-oxo-quinoline-3-carboxylic acid It was in a similar manner as described in example 26 in the list of EPIs active against NorA, where 4-amino-3-methylpiperidine was used in place of 5-amino-2-methylpyrrolidine. Yield 55%, m.p 228–30° C., $C_{19}H_{22}F_2N_4O_6$, m/z 393 (M+1).

EXAMPLE 14

5-Amino-1-cyclopropyl-6,8-difluoro-1,4-dihydro-7-(3'-quinuclidinyl-3'-yl-amino)-4-oxo-quinoline-3-carboxylic acid and its salts It was prepared in a similar manner as described in example 26 in the list of EPIs active against NorA, where 3-aminoquinuclidine was used in place of 5-amino-2-methyl-pyrrolidine. Yield 53%, m.p 280–82° C., $C_{20}H_{22}F_2N_4O_3$, m/z 404 (M+1)

EXAMPLE 15

5-Amino-1-cyclopropyl-6,8-difluoro-1,4-dihydro-7-{(1α,5α,6α)-6-amino-N-benzyl-3-azabicyclo[3.1.0] hex-6-yl}-4-oxo-quinoline-3-carboxylic acid and its salts It was prepared in a similar manner as described in example 26 in the list of EPIs active against NorA, where {(1α,5α,6α)-6-amino-N-benzyl-3-azabicyclo[3.1.0]hexane was used in place of 5-amino-2-methyl-pyrrolidine. Yield 75%, m.p 270–72° C., $C_{25}H_{24}F_2N_4O_3$, m/z 467 (M+1)

EXAMPLE 16

1-(3'-Fluorophenyl)-6-fluoro-1,4-dihydro-7-(4'-methylpiperazin-1'-yl)-4-oxo-quinoline-3-carboxylic acid and its salts The condensation of 1-(3'-fluorophenyl)-6,7-difluoro-1,4-dihydro-4-oxo-quinoline-3-carboxylic acid with 4-methylpiperazine in a similar manner as described in example 1 in the list of EPIs active against NorA, gave the titled product. Yield 58%, m.p 298–02° C., $C_{21}H_{19}F_2N_3O_3$, m/z 400. (M+1)

EXAMPLE 17

1-(2',4'-Difluorophenyl)-6-fluoro-1,4-dihydro-7-(4'-ethylaminopiperidin-1'-yl)-4-oxo-quinoline-3-carboxylic acid It was in a similar manner as described in example 45 in the list of EPIs active against NorA, where 4-ethylaminopiperidine was used in place of 3,3-dimethylpiperidine. Yield 62%, m.p 240–42° C., $C_{23}H_{22}F_3N_3O_3$, m/z 446 (M+1).

EXAMPLE 18

1-(2',4'-Difluorophenyl)-6-fluoro-5-methyl-1,4-dihydro-7-(4'-aminopiperidin-1'-yl)-4-oxo-quinoline-3-carboxylic acid and its salts The condensation of 1-(2,4-difluorophenyl)-6,7,8-trifuoro-5-methyl-1,4-dihydro-4-oxo-quinoline-3-carboxylic acid with 4-aminopiperidine in a similar manner as described in example 1 in the list of EPIs active against NorA, gave the titled product. Yield 58%, m.p 236–38° C., $C_{22}H_{20}F_3N_3O_3$, m/z 432 (M+1)

EXAMPLE 19

1-(2',4'-Difluorophenyl)-6-fluoro-5-methyl-1,4-dihydro-7-(4'-methylaminopiperidin-1'-yl)-4-oxo-quinoline-3-carboxylic acid and its salts It was prepared in a similar manner as described in example 18, where 4-methylaminopiperidine was used in place of 4-aminopiperidine. Yield 52%, m.p 204–06° C., $C_{23}H_{22}F_3N_3O_3$, m/z 346 (M+1)

EXAMPLE 20

1-Cyclopropyl-6-fluoro-1,4-dihydro-7-(3'-aminopyrrolidin-3'-yl-4-oxo-1,8-naphthyridine-3-carboxylic acid It was prepared in a similar manner as described in example 47 in the list of EPIs active against NorA, where 3-aminopyrrolidine was used in place of 3-amino ethoxycarbonylpyrrolidine. Yield 47%, m.p 120–22° C., $C_{16}H_{17}FN_4O_3$, m/z 323 (M+1)

EXAMPLE 21

1-Cyclopropyl-6-fluoro-1,4-dihydro-7-{(1α,5α,6α)-6-amino-N-benzyl-3-azabicyclo[3.1.0]hex-6-yl}-4-oxo-1,8-naphthyridine-3-carboxylic acid It was prepared in a similar manner as described in example 47 in the list of EPIs active against NorA, where {(1α,5α,6α)-6-amino-N-benzyl-3-azabicyclo[3.1.0]hexane was used in place of 3-anino ethoxycarbonylpyrrolidine Yield 67%, m.p 290–92° C. $C_{24}H_{23}FN_4O_3$, m/z 434 (M+1)

EXAMPLE 22

1-(2,4-Difluorophenyl)-6-fluoro-1,4-dihydro-7-(3'-aminopyrrolidin-3'-yl)-4-oxo-1,8-naphthyridine-3-carboxylic acid It was prepared in a similar manner as described in example 49 in the list of EPIs active against NorA, where 3-aminopyrrolidine was used in place of 4-amino ethoxycarbonylpiperidine. Yield 97%, m.p 268–70° C., $C_{21}H_{19}F_3N_4O_3$, m/z 433 (M+1)

EXAMPLE 23

1-(2,4-Difluorophenl)-6-fluoro-1,4-dihydro-7-{(1α,5α,6α)-6-amino-N-benzyl-3-azabicyclo[3.1.0]hex-6-yl}-4-oxo-1,8-naphthyridine-3-carboxylic acid It was prepared in a similar manner as described in example 49 in the list of EPIs active against NorA, where {(1α,5α,6α)-6-amino-N-benzyl-3-azabicyclo[3.1.0]hexane was used in place of 4-amino ethoxycarbonpiperidine. Yield 74%, m.p. 236–38° C., $C_{27}H_{21}F_3N_4O_3$, m/z 507 (M+1)

EXAMPLE 24

1-(2,4-Difluorophenyl)-6-fluoro-1,4-dihydro-7-(3',3'-dimethyl-4'-hydroxypiperdin-1-yl)-4-oxo-naphthyridine-3-carboxylic acid It was prepared in a similar manner as described in example 49 in the list of EPIs active against NorA, where 4-hydroxy-3',3'-dimethylpiperdine was used in place of 3-amino ethoxycarbonylpyrrolidine Yield 76%, m.p 194–98° C., $C_{22}H_{20}F_3N_3O_4$, m/z 448 (M+1)

EXAMPLE 25

(RS)-(±)-9-Fluoro-6,7-dihydro-8-{4'-(L-α-aspartyloxy)piperidin-1-yl}-5-methyl-1-oxo-1H,5H-benzo[i,j]quinolizine-2-carboyxlic acid hydrochloride It was prepared in a similar manner as described in example 51 in the list of EPIs active against NorA, where 4-(L-α-aspartyloxy)piperidine was used in place of 4-carboxamidopiperdine. Yield 68%, m.p 210–12° C., $C_{23}H_26FN_3O_7$, m/z 513 (M+1).

EXAMPLE 26

7H-Pyrido[1,2,3-de]-1,4-benzoxazine-9-fluoro-2,3-dihydro-3-methyl-10-(4'-hydroxy-3'-ethylpiperidin-1'-yl)-7-oxo-6-carboxylic acid It was prepared as described in example in the list of EPIs active against *Pseudomonas aeruginosa*.

EXAMPLE 27

7H-Pyrido[1,2,3-de]-1,4-benzoxazine-9-fluoro-2,3-dihydro-3-methyl-10-(3'-aminomethyl-4'-hydroxypiperidin-1'-yl)-7-oxo-6-carboxylic acid It was prepared in a similar manner as described in example 26, where 3-aminomethyl-4-hydroxypiperidine was used in place of 4-hydroxy-3-ethylpiperidine. Yield 69%, m.p 278–80° C., $C_{19}H_{22}FN_3O_5$, m/z 392 (M+1).

EXAMPLE 28

1-Cyclopropyl-6,8-difluoro-5-methyl-1,4-dihydro-7-(3',3'-dimethyl-4'-ethylaminopiperidin-1-yl)-4-oxo-quinoline-3-carboxylic acid It was prepared in a similar manner as described in example 10 of *Pseudomonas aeruginosa*, where 3,3-dimethyl-4-ethylaminopiperidine was used in place of 3-aminomethyl-4-hydroxypiperidine. Yield 52%, m.p 156–58° C., $C_{23}H_{30}FN_3O_3$, m/z 415 (M+1).

EXAMPLE 29

1-cyclopropyl-6,7,8-trifluoro-5-methyl-1,4-dihydro-4-oxo-quinoline-3-carboxylic acid Known compound (PCT WO 89/06649)

EXAMPLE 30

(S)-(−)-9-Fluoro-6,7-dihydro-8-(3',3'-dimethyl-4'-ethylaminopiperidin-1-yl)-5-methyl-1-oxo-1H,5H-benzo[i,j]quinolizine-2-carboxylic acid It was prepared in a similar manner as described in example 51 in the list of EPIs active against NorA, where 3,3-dimethyl-4-ethylaminopiperidine was used in place 4-carboxamidopiperdine. Yield 51%, m.p 302–04° C., $C_{23}H_{30}FN_3O_3$, m/z 415. (M+1)

EXAMPLE 31

1-Cyclopropyl-6-fluoro-1,4-dihydro-7-(3'-aminomethyl-4'-hydroxypiperidin 1-yl)-4-oxo-quinoline-3-carboxylic acid It was prepared in a similar manner as described in example 13 in the list of EPIs active against *Pseudomonas aeruginosa*, where 3-aminomethyl-4-hydroxypiperidin was used in place 4-ethyl-3-methylpiperazine. Yield 63%, m.p 230–34° C., $C_{18}H_{21}FN_4O_4$, m/z 378. (M+1)

EXAMPLE 32

1-Cyclopropyl-6-fluoro-1,4-dihydro-7-(4'-dimethylamino-3'-methylpiperidin-1-yl)-4-oxo-quinoline-3-carboxylic acid It was prepared in a similar manner as described in example 13 in the list of EPIs active against *Pseudomonas aeruginosa*, where 4-dimethylamino-3-methylpiperidine was used in place 4-ethyl-3-methylpiperazine. Yield 41%, m.p 180–88° C., $C_{20}H_{24}FN_3O_3$, m/z 374. (M+1)

EXAMPLE 33

5-Amino-1-cyclopropyl-6-fluoro-8-methoxy-1,4-dihydro-7-(4'-cyclopropylaminopiperidin-1-yl)-4-oxo-quinoline-3-carboxylic acid It was in a similar manner as described in example 24 in the list of EPIs active against NorA, where 4-cyclopropylaminopiperidine was used in place of 3,3-dimethylpiperidine.Yield 65%, m.p 218–20° C., $C_{23}H_{29}F_2N_4O_4$, m/z 445 (M+1).

EXAMPLE 34

1-Cyclopropyl-6-fluoro-8-methoxy-1,4-dihydro-7-{-4'-(t-butoxycarbonyl (L)-Ala-Ala)amino 3',3'-dimethylpiperidin-1-yl}-4-oxo-quinoline-3-carboxylic acid 1-Cyclopropyl-6-fluoro-8-methoxy-1,4-dihydro-7-{4'-amino-3',3'-dimethylpiperidin-1-yl}-4-oxo-quinoline-3-carboxylic acid (1.0 gm, 2.48 mmole), 4-(N-t-butoxycarbonyl)-L-alanine (0.94 gm, 4.96 mmole) and 2-ethoxy-N-ethyoxycarbonyl dihydroquinoline (EEDQ) (0.61 gm, 2.48 mmole) were dissolved in dichromethane (300 ml) and the mixture is stirred at room temperature for 48 hr. The mixture is washed with water, separate the layer, dried and concentrated. Product purified by silica gel column to furnish titled product. Yield 84%, m.p. 170–75° C., $C_{29}H_{39}FN_4O_7$, m/z 575 (M+1).

EXAMPLE 35

5-Amino-1-cyclopropyl-6-fluoro-8-methoxy-1,4-dihydro-7-{4'-ethylamino-3',5'-dimethylpiperidin-1-yl}-4-oxo-quinoline-3-carboxylic acid It was prepared in a similar manner as described in example 2, where 4-ethylamino-3,5-dimethylpiperidine was used in place of 4-methylamino-3,3-dimethylpiperidine. Yield 38%, m.p 255–58° C., $C_{23}H3,FN_4O_4$, m/z 447 (M+1)

EXAMPLE 36

Ethyl 1-(2,4-difluorophenyl)-6-fluoro-1,4-dihydro-7-(4-amino-3-ethylpiperidin-1-yl)-4-oxo-1,8-naphthyridine-3-carboxylate It was prepared in a similar manner as described in example 49 in the list of EPIs active against NorA, where 4-amino-3-ethylpiperidine was used in place of 4-amino ethoxycarbonylpiperidine. Yield 48%, m.p 178–80° C., $C_{24}H_{25}F_3N_4O_3$, m/z 475 (M+1)

EXAMPLE 37

1-(2,4-difluorophenyl)-6-fluoro-1,4-dihydro-7-(4-amino-3,5-dimethylpiperidin-1-yl)-4-oxo-1,8-naphthyridine-3-carboxylic acid It was prepared in a similar manner as described in example 49 in the list of EPIs active against NorA, where 4-amino-3,5-dimethylpiperidine was used in place of 4-amino ethoxycarbonylpiperidine. Yield 73%, m.p 180–82° C., $C_{22}H21F_3N_4O_3$, m/z 447 (M+1)

EXAMPLE 38

Ethyl 1-(2,4-difluorophenyl)-6-fluoro-5-methyl-1,4-dihydro-7-(4-amino-3,3-dimethylpiperidin-1-yl)-4-oxo-1,8-naphthyridine-3-carboxylate It was prepared in a similar manner as described in example 49 in the list of EPIs active against NorA, where 4-amino-3,3-dimethylpiperidine was used in place of 4-amino ethoxycarbonylpiperidine. Yield 67%, m.p 148–52 ° C., $C_{25}H_{27}F_3N_4O_3$, m/z 489 (M+1)

EXAMPLE 39

(S)-(−)-9-Fluoro-6,7-dihydro-8-(4'-hydrox 3'-fluoropiperidin-1-yl)-5-methyl-1-oxo-1H,5H-benzo[i,j]quinolizine-2-carboxylic acid It was prepared in a similar manner as described in example 51 in the list of EPIs active against NorA, where 4-hydroxy-3-fluoropiperidine was used in place 4-carboxamidopiperdine. Yield 46%, m.p 180° C., $C_{19}H_{20}F_2N_2O_4$, m/z 379 (M+1)

EXAMPLE 40

10-Fluoro-11-(4-aminopiperidin-1-yl)-3,4-dihydro-4 (S)-methyl-8-oxo-2H,8H-pyrido[1,2,3-ef]-1,5-benzoxazepin-7-carboxylic acid, hydrochloride It was prepared in a similar manner as described in example 36 in the fist of EPIs active against *Pseudomonas aeruginosa*, where 4-aminopiperidine was used in place [(1α,5α,6α)-6-amino-3-azabicyclo[3.1.0]hexane. Yield 56%, m.p 208–10° C., $C_{19}H_{23}ClFN_3O_4$, m/z 413 (M+1).

EXAMPLE 41

(RS)-(±)-6,7-dihydro-8-(trans-4'-hydroxy-3'-methylpiperidin-1-yl)-5-methyl-1-oxo-1H,5H-benzo[i,j]quinolizine-2-carboxylic acid It was prepared in a similar manner as described in example 32 in the list of EPIs active against *Pseudomonas aeruginosa*, Yield 59%, m.p 152–54° C., $C_{20}H_{24}N_2O_4$, m/z 356 (M+1).

EXAMPLE 42

(RS)-(±)-6,7-dihydro-8-(cis-4'-hydroxy-3'-methylpiperidin-1-yl)-5-methyl-1-oxo-1H,5H-benzo[i,j]quinolizine-2-carboxylic acid It was prepared in a similar manner as described in example 32 in the list of EPIs active against *Pseudomonas aeruginosa*, Yield 62%, m.p 162–64° C., $C_{20}H_{24}N_2O_4$, m/z 356 (M+1).

EXAMPLE 43

(RS)-(±)-6,7-dihydro-8-(4'-hydroxy-3',3'-dimethylpiperidin-1-yl)-5-methyl-1-oxo-1H,5H-benzo[i,j]quinolizine-2-carboxylic acid It was prepared in a similar manner as described in example 32 (Gm-Ve), Yield 43%, m.p 258–60° C., $C_{21}H_{26}N_2O_4$, m/z 370 (M+1)

Susceptibility Testing

Particular exemplary efflux pump inhibitor compounds within the generic descriptions of the compounds of this invention were evaluated for potentiation effect. The in vitro microbiological data for antibiotic potentiation is presented in Tables 1–5.

Testing method for inhibition of the efflux pump of *Staphylococcus aureus* 1199B NorA+

Compounds disclosed herein were studied for potentiation effect by determining the Fractional Inhibition Concentration (FIC) index of compounds and ciprofloxacin. Potentiation effect is observed by the reduction of minimal inhibitory concentration (MIC) of ciprofloxacin in the presence of the experimental efflux pump inhibitor. The activity of an efflux pump inhibitor in combination with a fluoroquinolone such as ciprofloxacin is assessed by the checkerboard assay and the FIC index was calculated. An FIC index value of $\leq 0.5$ is synergistic of 0.5–2.0 is additive and >2.0 is antagonistic (Antimicrobial Combination In Antibiotics in Laboratory Medicine, Ed. Victor Lorian, Md., Fourth edition 1996, pp 333–338).

In short, the assay involves broth microdilution method performed as recommended by the National Committee for Clinical Laboratory Standards (NCCLS) 1997 (Methods for Dilution of Antimicrobial Susceptibility Tests for Bacteria that Grow Aerobically, Fourth edition; Approved Standard, NCCLS document M7-A4, vol. 17, No. 2). The test organism used for the assay is *Staphylococcus aureus* 1199 B NorA+.

In this assay, multiple dilution of two drugs viz. the experimental efflux pump inhibitor and ciprofloxacin are being tested, alone and in combination, at concentrations equal to above and below the respective MICs. In the case of the efflux pump inhibitors of the invention, a number of compounds display intrinsic antimicrobial activity, but are tested at sub-MIC concentrations of 4 mcg–20mcg/ml.

Stock solutions of the efflux pump inhibitors tested are prepared in dimethyl sulfoxide (DMSO) at a final concentration of 5 mg/ml. Stock solutions are further diluted in Mueller Hinton Broth as per the need of the assay. Ciprofloxacin is dissolved in water.

The checkerboard assay is performed in microtiter plates. Ciprofloxacin is diluted in the X-axis, each column containing a single concentration of ciprofloxacin. The efflux pump inhibitor is diluted in the Y-axis, each row containing an equal concentration of efflux pump inhibitor. The result of these manipulations is that each well of the microtiter plate contains a unique combination of concentrations of the two agents. Bacterial inoculum is added at $5 \times 10^5$ CFU/ml. Microtiter plates are incubated at 35° C. for 20 hours. Reading is done by visibly noting turbidity and confirmed using a microtiter plate reader (Molecular Devices). The FIC index is calculated as $$\frac{(A)}{(MIC_A)} + \frac{(B)}{(MIC_B)} = FIC_A + FIC_B = FIC \text{ Index}$$

(A) is the concentration of the experimental efflux pump inhibitor in the well that is the lowest inhibitory concentration in the Y-axis. ($MIC_A$) is the MIC of *Staphylococcus aureus* to experimental efflux pump inhibitor alone. $FIC_A$ is the fractional inhibitory concentration of an experimental efflux pump inhibitor. (B) is the concentration of the ciprofloxacin in the well that is the lowest inhibitory concentration in the X-axis. $FIC_B$ is the fractional inhibitory concentration of ciprofloxacin. (Antimicrobial Combination In Antibiotics in Laboratory Medicine, Ed. Victor Lorian, Md., Fourth edition 1996, pp 333–338).

Testing method for Inhibition of the Efflux Pumps of *Pseudomonas aeruzinosa* 23587, *E. coli* 2051, *Streptococcus pneumoniae* 3514 and *Streptococcus pyozenus* 26-00

Antibiotic Diffusion Assay

The activity of efflux pump inhibitor was also assessed using an antibiotic diffusion assay. For this assay *Pseudomonas aeruginosa* 23587 is used. *Pseudomonas aeruginosa* 23587 is a clinical isolate containing multiple efflux pumps which can be mexAB, mexCD, mexEF but not limited to mex classification only. *Pseudomonas aeruginosa* are grown in tryptic soya broth for 20 hours at 35° C. Two antibiotic assay plates are prepared in Mueller Hinton Agar using above inoculum. The bacterial count in a plate is $1 \times 10^6$ cells/ml. In one of the plates, levofloxacin is incorporated at 5 mcg/ml, while in the control plate an equivalent amount of water is added. An experimental efflux pump inhibitor is evaluated by adding a series of concentrations of the test compound ranging from 0.025 mcg to 200 mcg./well in agar plate. The plates are incubated at 35° C. for 20 hours and the zone of inhibition was recorded in mm (table 2). The difference in the diameter of zone of inhibition was calculated by subtracting from the diameter of the zone of inhibition in the levofloxacin containing plate the diameter of the zone of inhibition in the water containing control plate. Example, if the diameter of the zone of inhibition in the levofloxacin plate is X mm and the diameter of the zone of inhibition in the control plate is Y mm, the difference Z=X−Y and is a measure of the activity of the efflux pump inhibitor.

The activity of an efflux pump inhibitor of *E. coli* 2051 was also assessed using an antibiotic diffusion assay. For this assay *E. coli* 2051 is used. *E. coli* 2051 is a clinical isolate containing multiple efflux pumps. *E. coli* 2051 are grown in tryptic soya broth for 20 hours at 35° C. Two antibiotic assay plates are prepared in Mueller Hinton Agar using above inoculum. The bacterial count in a plate is $1\times10^6$ cells/ml. In one of the plates, levofloxacin is incorporated at 15 mcg/ml, while in the control plate an equivalent amount of water is added. An experimental efflux pump inhibitor is evaluated by adding a series of concentrations of the test compound ranging from 0.025 mcg to 200 mcg./well in agar plate. The plates are incubated at 35° C. for 20 hours and the zone of inhibition was recorded in mm (table 3). The difference in the diameter of zone of inhibition was calculated by subtracting from the zone of inhibition in the levofloxacin containing plate the diameter of the zone of inhibition in the control plate.

To detect the macrolide efflux pump Chef) inhibitor, *Streptococcus pneumoniae* 3514 (Mef+) is used which was obtained from the Centre for Disease Control (CDC), Atlanta. A similar 2 plate assay method as described above is used with small modifications. *Streptococcus pneumoniae* 3514 (Mef+) is grown in Columbia blood agar for 18 hours at 25° C. The growth was suspended in sterile todd hewitt broth and CFU were adjusted using macfarland's standard to $1\times10^8$ CFU/ml. 0.5 ml of this is added to the Mueller Hinton agar supplemented with 5% sheep blood, final bacterial count was $10^6$ cells/ml. In one of the two plates 0.5 mcg/ml azithromycin is incorporated and to the control plate an equivalent amount of water is added. The plates are incubated at 35° C. for 20 hours and the zone of inhibition was recorded in mm (table 4). The difference in the diameter of zone of inhibition was calculated by subtracting from the diameter of the zone of inhibition in the azithromycin containing plate the diameter of the zone of inhibition in the control plate.

To detect the macrolide efflux pump (Met) inhibitor, *Streptococcus pyogenus* 26-00 is used which was obtained from the Centre for Disease Control (CDC), Atlanta. A similar 2 plate assay method as described above is used with small modifications. *Streptococcus pyogenus* 26-00 (Mef+) is grown in Columbia blood agar for 18 hours at 25° C. The growth was suspended in sterile todd hewitt broth and CFU were adjusted using macfarland's standard to $1\times10^8$ CFU/ml. 0.5 ml of this is added to the Mueller Hlinton agar supplemented with 5% sheep blood, final bacterial count was $10^6$ cells/ml. In one of the two plates 0.5 mcg/ml azithromycin is incorporated and to the control plate an equivalent amount of water is added. The plates are incubated at 35° C. for 20 hours and the zone of inhibition was recorded in mm (table 4). The difference in the diameter of zone of inhibition was calculated by subtracting from the diameter of the zone of inhibition in the azithromycin containing plate the diameter of the zone of inhibition in the control plate.

The Results of the Screening are Provided in the Following Tables:

TABLE 1

Some Preferred Compounds of the Invention Displaying Inhibition of the Efflux Pump of *Staphylococcus aureus* 1199 B (Nor A⁺)

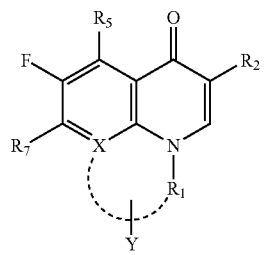

| X | $R_1$ | $R_2$ | $R_5$ | $R_7$ | FIC INDEX |
|---|---|---|---|---|---|
| C—H | $C_2H_5$ | COOH | H | 1,2,3,4-tetrahydroisoqninolin-2-yl | 0.314 |
| C—F | $C_2H_5$ | COOH | H | 4-acetoxypiperidin-1-yl | 0.314 |
| C—F | $C_2H_5$ | COOH | H | 4-{2-(2-oxazolidin-1yl)ethyl}piperazin-1-yl | 0.188 |
| C—F | $C_2H_5$ | COOH | H | (1∝, 5∝, 6∝)-6-amino-3-azabicyclo[3.1.0]hex-3-yl | 0.192 |
| C—F | $C_2H_5$ | COOR | $NH_2$ | 3-amino-5-methylpyrrolidin-1-yl | 0.378 |
| C—F | $C_2H_5$ | COOH | $NH_2$ | 4-aminopiperidin-1-yl | 0.314 |
| C—F | $C_2H_5$ | COOH | $NH_2$ | 4-(acetamido)piperidin-1-yl | 0.312 |
| C—F | $C_2H_5$ | COOH | $NH_2$ | (1∝, 5∝, 6∝)-6-(t-butoxycarbonylamino)-3-azabicyclo[3.1.0]hex-3-yl | 0.314 |
| C—H | c-$C_3H_5$ | COOH | H | 3-acetamido-5-methylpyrrolidin-1-yl | 0.314 |
| C—H | c-$C_3H_5$ | COOH | H | 3-amino-5-methylpyrrolidin-1-yl | 0.314 |
| C—H | c-$C_3H_5$ | COOH | H | 4-acetoxypiperidin-1-yl | 0.282 |
| C—H | c-$C_3H_5$ | COOH | H | 4-(dimethylamino)piperidin-1-yl | 0.188 |
| C—H | c-$C_3H_5$ | COOH | H | 3,5-dimethylpiperidin-1-yl | 0.314 |
| C—H | c-$C_3H_5$ | COOH | H | 4-hydroxy-3,5-dimethyl-piperidin-1-yl | 0.314 |
| C—H | c-$C_3H_5$ | COOH | H | 3,4,5-trimethylpiperazin-1-yl | 0.314 |

TABLE 1-continued

| | | | | | |
|---|---|---|---|---|---|
| C—H | c-C$_3$H$_5$ | COOH | H | 3,5-dimethyl-4-ethylpiperazin-1-yl | 0.314 |
| C—H | c-C$_3$H$_5$ | COOH | CH$_3$ | 4-ethoxypiperidin-1-yl | 0.378 |
| C—H | c-C$_3$H$_5$ | COOH | CH$_3$ | 3,3-dimethylpiperazin-1-yl | 0.314 |
| C—OCH$_3$ | c-C$_3$H$_5$ | COOH | H | 4-(dimethylamino)-3-methyl-piperidin-1-yl | 0.200 |
| C—OCH$_3$ | c-C$_3$H$_5$ | COOH | H | 4-hydroxy-3-isobutyl-piperidin-1-yl | 0.248 |
| C—OCH$_3$ | c-C$_3$H$_5$ | COOH | H | 4-hydroxy-3,3-dimethyl-piperidin-1-yl | 0.264 |
| C—OCH$_3$ | c-C$_3$H$_5$ | COOH | H | 4-hydroxy-3,5-dimethyl-piperidin-1-yl | 0.370 |
| C—OCH$_3$ | c-C$_3$H$_5$ | COOH | H | 3-methylpiperazin-1-yl | 0.314 |
| C—OCH$_3$ | c-C$_3$H$_5$ | COOH | NH$_2$ | cis-4-amino-3,5-dimethyl-piperidin-1-yl | 0.314 |
| C—F | c-C$_3$H$_5$ | COOH | CH$_3$ | 4-hydroxy-3-aminomethyl-piperidin-1-yl | 0.192 |
| C—F | c-C$_3$H$_5$ | COOH | NH$_2$ | 5-amino-2-methyl-pyrrolidin-1yl | 0.628 |
| C—F | c-C$_3$H$_5$ | COOH | NH$_2$ | 3-(L-Ala-L-Ala)-aminopyrrolidin-1-yl | 0.128 |
| C—F | c-C$_3$H$_5$ | COOH | NH$_2$ | 4-(di-n-butylamino)piperidin-1-yl | 0.314 |
| C—F | c-C$_3$H$_5$ | COOH | NH$_2$ | 4-(t-butoxycarbonyamino-L-AIa-L-Ala)aminopiperirlin-1-yl | 0.320 |
| C—F | c-C$_3$H$_5$ | COOH | NH$_2$ | 4-propionoxypiperidin-1-yl | 0.314 |
| C—F | c-C$_3$H$_5$ | COOH | NH$_2$ | 4-hydroxy-3,3-dimethyl-piperidin-1-yl | 0.304 |
| C—F | c-C$_3$H$_5$ | COOH | NH$_2$ | 4-(1-pyrrolidinyl)piperidin-1-yl | 0.340 |
| C—F | c-C$_3$H$_5$ | COOH | NH$_2$ | 4-[(piperidin-4-yl)aminomethyl]-piperidin-1-yl | 0.314 |
| C—F | c-C$_3$H$_5$ | COOH | NH$_2$ | (1,2,2,6,6-pentamethylpiperidin-4-yl)methylamino | 0.282 |
| C—F | c-C$_3$H$_5$ | COOH | NH$_2$ | 3,5-dimethylmorpholin-1-yl | 0.314 |
| C—F | c-C$_3$H$_5$ | COOH | NH$_2$ | 4-cyclopropylpiperazin-1-yl | 0.314 |
| C—F | c-C$_3$H$_5$ | COOH | NH$_2$ | 3,5-dimethyl-4-pivaloylpiperazin-1-yl | 0.314 |
| C—F | CH(CH$_3$)—CH$_2$CH$_2$SC$_6$H$_5$ | COOC$_2$H$_5$ | H | 4-hydroxypiperidin-1-yl | 0.100 |
| C—H | C$_6$H$_4$CF$_3$(2) | COOH | H | 3,3,4-trimethylpiperazin-1-yl | 0.282 |
| C—F | C$_6$H$_4$CF$_3$(2) | COOH | NH2 | morpholin-1-yl | 0.314 |
| C—F | C$_6$H$_4$CF$_3$(2) | COOH | NH2 | 3,5-dimethylmorpholin-1-yl | 0.384 |
| C—F | C$_6$H$_4$CF$_3$(2) | COOH | NH2 | 3,5-dimethylpiperazin-1-yl | 0.314 |
| C—F | C$_6$H$_4$CF$_3$(4) | COOH | NH2 | 3-aminopyrrolidin-1-yl | 0.564 |
| C—H | C$_6$H$_4$F(4) | COOH | H | 4-(ethylamino)piperidin-1-yl | 0.189 |
| C—H | C$_6$H$_3$F$_2$(2,4) | COOH | H | 3,5-dimethylpiperidin-1-yl | 0.192 |
| C—F | C$_6$H$_3$F$_2$(2,4) | COOH | NH$_2$ | 3-hydroxy-5-methylpyrrolidin-1-yl | 0.314 |
| C—F | C$_6$H$_3$F$_2$(2,4) | COOH | NH$_2$ | 3,3-dimethylpiperazin-1-yl | 0.375 |
| N | c-C$_3$H$_5$ | COOH | H | (3-ethoxycarbonylamino)pyrrolidin-3-yl 0.314 | |
| N | c-C$_3$H$_5$ | COOH | H | pyrrolidin-3-ylamino | 0.188 |
| N | C$_6$H$_3$F$_2$(2,4) | COOH | H | piperidin-4-ylamino | 0.314 |
| N | C$_6$H$_3$F$_2$(2,4) | COOC$_2$H$_5$ | H | {(1α, 5α, 6α)-3-N-benzyl-3-azabicyclo[3.1.0]hex-6-yl}amino | 0.185 |
| N | C$_6$H$_3$F$_2$(2,4) | COOC$_2$H$_5$ | H | 1-phenyl-4,5,6,7-tetrahydropyrazolo[4,3-c]pyridin-1-yl | 0.100 |
| C—CH$_2$CH$_2$C*H(CH$_3$) | | COOH | H | 4-carboxamido-piperidin-1-yl | 0.192 |
| C—CH$_2$CH$_2$C**H(CH$_3$) | | COOH | H | 4-hydroxypiperidin-1-yl arginine salt | 0.314 |
| C—CH$_2$CH$_2$C*H(CH$_3$) | | COOH | H | 4-hydroxy-3,3-dimethyl-piperidin-1-yl | 0.378 |
| C—CH$_2$CH$_2$C*H(CH$_3$) | | COO-piperidin-N—CH$_3$ | H | 4-hydroxypiperidin-1-yl | 0.180 |
| C—CH$_2$CH$_2$C*H(CH$_3$) | | COOCH$_2$CH$_2$-morpholine | H | 4-Hydroxypiperidin-1-yl | 0.370 |
| C—CH$_2$CH$_2$C**H(CH$_3$) | | COOCH$_2$COOC$_2$H$_5$ | H | 4-hydroxypiperidin-1-yl | 0.400 |

Examples of Bis compounds of the invention Displaying Inhibition
of the Efflux Pump of *Staphylococcus aureus* 1199 B
(Nor A$^+$)

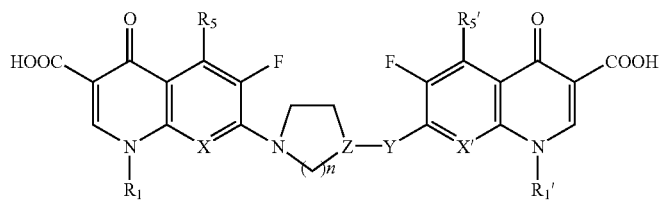

| R$_1$ | R$_5$ | X | n | Z | Y | R$_1$' | R$_5$' | X' | FIC INDEX |
|---|---|---|---|---|---|---|---|---|---|
| c-C$_3$H$_5$ | H | CH | 1 | CH | NH | C$_6$H$_3$F$_2$(2,4) | H | N | 0.253 |
| c-C$_3$H$_5$ | H | N | 1 | CH | NH | c-C$_3$H$_5$ | H | N | 0.282 |
| c-C$_3$H$_5$ | H | N | 1 | CH | NH | c-C$_3$H$_5$ | NH$_2$ | CF | 0.314 |
| c-C$_3$H$_5$ | H | N | 2 | N | — | c-C$_3$H$_5$ | NH$_2$ | CF | 0.282 |
| c-C$_3$H$_5$ | CH$_3$ | CH | 1 | CH | NH | C$_6$H$_3$F$_2$(2,4) | H | N | 0.320 |
| c-C$_3$H$_5$ | CH$_3$ | CH | 2 | CH | NH | c-C$_3$H$_5$ | NH$_2$ | CF | 0.304 |
| c-C$_3$H$_5$ | CH$_3$ | CH | 1 | CH | NH | c-C$_3$H$_5$ | NH$_2$ | CF | 0.304 |
| C$_6$H$_3$F$_2$(2,4) | H | N | 2 | N | — | c-C$_3$H$_5$ | H | CH | 0.192 |

TABLE 1-continued

| R₁ | R₅ | X | R₁' | R₅' | X' | FIC INDEX |
|---|---|---|---|---|---|---|
| C₆H₃F₂(2,4) | CH | N | C₆H₃F₂(2,4) | CH | N | 0.314 |

| R₁ | R₅ | X | FIC INDEX |
|---|---|---|---|
| c-C₃H₅ | NH₂ | CF | 0.304 |

*S-isomer;
**R-isomer;
Absence of an asterisk indicates that the substance is a racemic compound.

TABLE 2

Some Preferred Compounds of the Invention Displaying Inhibition of the Efflux Pumps of *Pseudoinonas aeruginosa* 23587

| X | R₁ | R₂ | R₅ | R₇ | Difference in Zone diameter $Z^1$ (mm) |
|---|---|---|---|---|---|
| C—H | c-C₃H₅ | COOH | CH₃ | 4-methoxypiperidin-1-yl | 13 |
| C—H | c-C₃H₅ | COOH | CH₃ | Br | 1 |
| C—OCH₃ | c-C₃H₅ | COOH | H | 4-amino-3-methyl-piperidin-1-yl | 7 |
| C—OCH₃ | c-C₃H₅ | COOH | NH₂ | 4-amino-3-methyl-piperidin-1-yl | 5 |
| C—OCH₃ | c-C₃H₅ | COOH | NH₂ | 4-(ethylamino)-3,3-dimethyl-piperidin-1-yl | 3 |
| C—OCH₃ | c-C₃H₅ | COOH | H | 4-amino-3,3-dimethyl-piperidin-1-yl | 12 |
| C—OCH₃ | c-C₃H₅ | COOH | H | 4-(dimethylamino)piperidin-1-yl | 5 |
| C—OCH₃ | c-C₃H₅ | COOH | H | 4-hydroxy-4-methyl-piperidin-1-yl | 5 |
| C—OCH₃ | c-C₃H₅ | COOH | H | 4-hydroxy-3,3-dimethyl-piperidin-1-yl | 8 |
| C—F | c-C₃H₅ | COOH | CH₃ | 4-hydroxy-3-aminomethyl-piperidin-1-yl | 5 |
| C—F | c-C₃H₅ | COOH | NH₂ | 4-hydroxy-3-aminomethyl-piperidin-1-yl | 3 |
| C—F | C₂H₅ | COOH | H | 3,5-dimethylpiperazin-1-yl | |
| C—H | c-C₃H₅ | COOH | H | 4-ethyl-3-methylpiperazin-1-yl | 4 |
| C—H | c-C₃H₅ | COOH | H | 3,5-dimethyl-4-ethylpiperazin-1-yl | 8 |
| C—F | C₂H₅ | COOH | H | (1α, 5α, 6α)-6-amino-3-azabicyclo[3.1.0]hex-3-yl | 7 |

TABLE 2-continued

Some Preferred Compounds of the Invention Displaying Inhibition of the Efflux Pumps of *Pseudoinonas aeruginosa* 23587

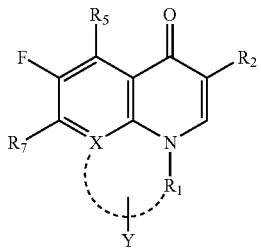

| X | $R_1$ | $R_2$ | $R_5$ | $R_7$ | Difference in Zone diameter $Z^1$ (mm) |
|---|---|---|---|---|---|
| C—F | $C_6H_3(2,4-F_2)$ | COOH | NH2 | 3-aminopyrrolidin-1-yl | 3 |
| C—F | c-$C_3H_5$ | COOH | NH2 | (3-aminoethoxycarbonyl)pyrrolidin-3-yl | 8 |
| N | c-$C_3H_5$ | COOH | H | pyrrolidin-3-ylamino | 6 |
| N | $C_6H_3(2,4-F_2)$ | COOH | H | piperidin-4-ylamino | 6 |
| N | c-$C_3H_5$ | COOH | H | 4-amino-3-ethyl-piperidin-1-yl | 6 |
| C—$CH_2CH_2C^*H(CH_3)$ | COOH | H | 4-hydroxypiperidin-1-yl (0.2 $H_2O$) | 5 |
| C—$CH_2CH_2C^*H(CH_3)$ | COOH | H | 4-hydroxypiperidin-1-yl.[$(CH_3)_3N(OH)(CH_2)_2OH$]salt | 3 |
| C—$CH_2CH_2C^*H(CH_3)$ | COOH | H | 4-hydroxypiperidin-1-yl.1-Hydroxyethylpyrrolidine salt | 3 |
| C—$CH_2CH_2C^*H(CH_3)$ | COOH | H | 4-hydroxypiperidin-1-yl.Diethanolamine salt | 4 |
| C—$CH_2CH_2C^*H(CH_3)$ | COOH | H | 4-hydroxypiperidin-1-ylL-histidine salt | 5 |
| C—$CH_2CH_2CH(CH_3)$ | COOH | H | 4-(D-phenylalanyloxy)piperidin-1-yl hydrochloride | 12 |
| C—$CH_2CH_2CH(CH_3)$ | COOH | H | 4-(L-∝-aspartyloxypiperidin-1-yl hydrochloride | 11 |
| C—$CH_2CH_2CH(CH_3)$ | COOH | H | 4-(L-leucyloxy)piperidin-1-yl dihydrochloride | 8 |
| C—$CH_2CH_2C^*H(CH_3)$ | COOH | H | 4-(D-leucyloxy)piperidin-1-yl hydrochloride | 12 |
| C—$CH_2CH_2C^*H(CH_3)$ | COOH | H | 4-(L-alanyloxy)piperidin-1-yl hydrochloride | 9 |
| C—$CH_2CH_2C^*H(CH_3)$ | COOCH$_2$CH$_2$-morpholine | H | 4-hydroxypiperidin-1-yl | 2 |
| C—$CH_2CH_2C^{**}H(CH_3)$ | COPhe-Lys-OMe | H | F | 8 |
| C—$CH_2CH_2CH(CH_3)$ | COOH | H | trans-4-hydroxy-3-methyl-piperidin-1-yl | 6 |
| C—$CH_2CH_2CH(CH_3)$ | COOH | H | cis-4-hydroxy-3-methyl-piperidin-1-yl | 6 |
| C—$CH_2CH_2C^*H(CH_3)$ | COOH | H | trans-3-methyl-4-hydroxypiperidin-1-yl | 8 |
| C—$OCH_2CH(CH_3)$ | COOH | H | 4-hydroxy-3-ethyl-piperidin-1-yl | 5 |
| C—$OCH_2CH_2CH(CH_3)$ | COOH | H | (1∝, 5∝, 6∝)-6-amino-3-azabicyclo[3.1.0]hex-3-yl | 2 |

$^1Z$ = the difference of the diameter of the zone of inhibition in the levofloxacin containing plate minus the diameter of the zone of inhibition in the water containing control plate.
*S-isomer;
**R-isomer;
Absence of an asterisk indicates that the substance is a racemic compound.

TABLE 3

Some Preferred Compounds of the Invention Displaying Inhibition of the Efflux Pumps of *Escherischia coli* 2051

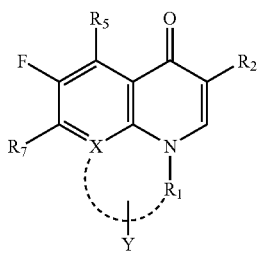

| X | $R_1$ | $R_2$ | $R_5$ | $R_7$ | Difference in Zone diameter $Z^1$ (mm) |
|---|---|---|---|---|---|
| CH | c-$C_3H_5$ | COOH | $CH_3$ | Br | 9 |
| C—$OCH_3$ | c-$C_3H_5$ | COOH | H | 4-amino-3-methyl-piperidin-1-yl | 10 |
| C—$OCH_3$ | c-$C_3H_5$ | COOH | H | 4-amino-3,3-dimethyl-piperidin-1-yl | 11 |
| C—$CH_2CH_2C^*H(CH_3)$ | COOH | H | 4-hydroxypiperidin-1-yl (0.2 $H_2O$) | 9 |
| C—$CH_2CH_2C^*H(CH_3)$ | COOH | H | 4-hydroxypiperidin-1-yl.[$(CH_3)_3N(OH)(CH_2)_2OH$]salt | 9 |
| C—$CH_2CH_2C^*H(CH_3)$ | COOH | H | 4-hydroxypiperidin-1-yl.1-Hydroxyethylpyrrolidine salt | 11 |
| C—$CH_2CH_2C^*H(CH_3)$ | COOH | H | 4-hydroxypiperidin-1-yl.Diethanolamine salt | 11 |
| C—$CH_2CH_2C^*H(CH_3)$ | COOH | H | 4-(D-leucyloxy)piperidin-1-yl hydrochloride | 18 |
| C—$CH_2CH_2C^*H(CH_3)$ | COOCH$_2$CH$_2$-morpholine | H | 4-Hydroxypiperidin-1-yl | 8 |

TABLE 3-continued

Some Preferred Compounds of the Invention Displaying Inhibition of the Efflux Pumps of *Escherischia coli* 2051

| X | R₁ | R₂ | R₅ | R₇ | Difference in Zone diameter $Z^1$ (mm) |
|---|---|---|---|---|---|
| C—CH₂CH₂C**H(CH₃) | | CO-phe-lysOMe | H | F | 11 |
| C—CH₂CH₂C*H(CH₃) | | COOH | H | trans-3-methyl-4-hydroxypiperidin-1-yl | 8 |
| C—OCH₂CH₂C*H(CH₃) | | COOH | H | (1∝, 5∝, 6∝)-6-amino-3-azabicyclo[3.1.0]hex-3-yl | 5 |

$^1$Z = the difference of the diameter of the zone of inhibition in the levofloxacin containing plate minus the diameter of the zone of inhibition in the water containing control plate.
*S-isomer;
**R-isomer;
Absence of an asterisk indicates that the substance is a racemic compound.

TABLE 4

Some Preferred Compounds of the Invention Displaying Inhibition of the Mef Efflux Pump of *Streptococcus pneumoniae* 3514 and *Streptococcus pyogenes* 26–00

| X | R₁ | R₂ | R₅ | R₇ | Difference in Zone diameter $Z^1$ (mm) |
|---|---|---|---|---|---|
| C—OCH₃ | c-C₃H₅ | COOH | H | 4-amino-3-methyl-piperidin-1-yl | 26 |
| C—OCH₃ | c-C₃H₅ | COOH | NH₂ | 4-(methylamino)-3,3-dimethyl-piperidin-1-yl | 8 |
| C—OCH₃ | c-C₃H₅ | COOCH(CH₃)₂ | H | 4-amino-3,3-dimethyl-piperidin-1-yl | 11 |
| C—OCH₃ | c-C₃H₅ | COO(CH₂)₃CH₃ | H | 4-amino-3,3-dimethyl-piperidin-1-yl | 11 |
| C—OCH₃ | c-C₃H₅ | COOCH₂COOCH₂CH₃ | H | 4-amino-3,3-dimethyl-piperidin-1-yl | 13 |
| C—OCH₃ | c-C₃H₅ | COOCH₂C₆H₅ | H | 4-(t-butoxycarbonylamino)-3,3-dimethyl-piperidin-1-yl | 13 |
| C—OCH₃ | c-C₃H₅ | COOH | H | 4-(t-butoxycarbonyl-L-alanyl)amino-3,3-dimethyl-piperidin-1-yl | 7 |
| C—OCH₃ | c-C₃H₅ | COOH | H | 4-L-alanylamino-3,3-dimethyl-piperidin-1-yl.HCl | 10 |
| C—OCH₃ | c-C₃H₅ | COOH | H | 4-(L-t-butoxycarbonylvalylamino)-3,3-dimethyl-piperidin-1-yl | 5 |
| C—OCH₃ | c-C₃H₅ | COOH | H | 4-L-valylamino-3,3-dimethyl-piperidin-1-yl.HCl | 8 |
| C—OCH₃ | c-C₃H₅ | COOH | H | 4-L-aspartylamino-3,3-dimethyl-piperidin-1-yl.HCl | 6 |
| C—F | C₂H₅ | COOH | H | 4-ethylaminopiperidin-1-yl | 18 |
| C—F | c-C₃H₅ | COOH | NH₂ | 4-amino-3-methyl-piperidin-1-yl | 20 |
| C—F | c-C₃H₅ | COOH | NH₂ | Quinuclidinyl-3'-yl-amino | 8 |
| C—F | c-C₃H₅ | COOH | NH₂ | (1∝, 5∝, 6∝)-3-N-benzylazabicyclo[3.1.0]hex-6-yl-amino | 14 |
| C—H | C₆H₄(3-F) | COOH | H | 4-methylpiperazin-1-yl | 10 |
| C—H | C₆H₃(2,4-F₂) | COOH | H | 4-ethylaminopiperidin-1-yl | 9 |
| CH | C₆H₃(2,4-F₂) | COOH | CH₃ | 4-aminopiperidin-1-yl | 8 |
| CH | C₆H₃(2,4-F₂) | COOH | CH₃ | 4-methylaminopiperidin-1-yl | 8 |
| N | c-C₃H₅ | COOH | H | 3-aminopyrrolidin-1-yl | 10 |
| N | c-C₃H₅ | COOH | H | (1∝, 5∝, 6∝)-3-N-benzylazabicyclo[3.1.0]hex-6-yl-amino | 17 |
| N | C₆H₃(2,4-F₂) | COOH | H | 3-aminopyrrolidin-1-yl | 8 |
| N | C₆H₃(2,4-F₂) | COOH | H | (1∝, 5∝, 6∝)-3-N-benzylazabicyclo[3.1.0]hex-6-yl-amino | 15 |
| N | C₆H₃(2,4-F₂) | COOH | H | 3,3-dimethyl-4-hydroxypiperidin-1-yl | 10 |
| —C—CH₂CH₂CH(CH₃) | | COOH | H | 4-(L-∝-aspartyl)-piperidin-1-yl.HCl | 6 |
| —C—OCH₂CH(CH₃) | | COOH | H | 3-ethyl-4-hydroxypiperidin-1yl | 5 |
| —C—OCH₂CH(CH₃) | | COOH | H | 3-aminomethyl-4-hydroxypiperidine | 16 |
| CF | c-C₃H₅ | COOH | CH₃ | 3,3-dimethyl-4-ethylaminopiperidine | 10 |

TABLE 4-continued

Some Preferred Compounds of the Invention Displaying Inhibition of the Mef Efflux Pump of
Streptococcus pneumoniae 3514 and Streptococcus pyogenes 26–00

| | | | | | | |
|---|---|---|---|---|---|---|
| CF | c-C$_3$H$_5$ | COOH | CH$_3$ | F | | 10 |
| —C—CH$_2$CH$_2$C*H(CH$_3$) | | COOH | H | 3,3-dimethyl-4-ethylaminopiperidine | | 8 |
| CH | c-C$_3$H$_5$ | COOH | H | 3-aminomethyl-4-hydroxypiperidine | | 6 |
| CH | c-C$_3$H$_5$ | COOH | H | 4-dimethylamino-3-methylpiperidine | | 8 |
| C-OCH$_3$ | c-C$_3$H$_5$ | COOH | NH$_2$ | 4-cyclopropylaminopiperidine | | 10 |
| C-OCH$_3$ | c-C$_3$H$_5$ | COOH | H | 4-(t-butoxycarbonyl(L)-Ala-Ala)amino 3,3-dimethylpiperidin-1-yl | | 8 |
| C-OCH$_3$ | c-C$_3$H$_5$ | COOH | NH$_2$ | 4-ethylamino-3,5-dimethylpiperidin-1-yl | | 13 |
| N | C$_6$H$_3$(2,4-F$_2$) | COOC$_2$H5 | H | 4-amino-3-ethylpiperidin-1-yl | | 10 |
| N | C$_6$H$_3$(2,4-F$_2$) | COOH | H | 4-amino-3,5-dimethylpiperidin-1-yl | | 7 |
| N | C$_6$H$_3$(2,4-F$_2$) | COOC$_2$H$_5$ | CH$_3$ | 4-amino-3,3-dimethylpiperidin-1-yl- | | 10 |
| —C—CH$_2$CH$_2$C*H(CH$_3$) | | COOH | H | 3-fluoro-4-hydroxypiperidin-1-yl | | 8 |
| —C—OCH$_2$CH$_2$C*H(CH$_3$) | | COOH | H | 4-aminopiperidin-1-yl.HCl | | 13 |

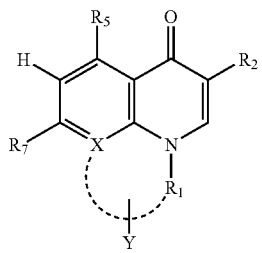

| | | | | | Difference in Zone diameter |
|---|---|---|---|---|---|
| X | R$_1$ | R$_2$ | R$_5$ | R$_7$ | Z$^1$ (mm) |
| —C— | CH$_2$CH$_2$CH(CH$_3$) | COOH | H | trans-4-hydroxy-3-methylpiperidine | 10 |
| —C— | CH$_2$CH$_2$CH(CH$_3$) | COOH | H | cis-4-hydroxy-3-methylpiperidine | 8 |
| —C— | CH$_2$CH$_2$CH(CH$_3$) | COOH | H | 4-hydroxy-3,3-dimethylpiperidine | 10 |

$^1$Z = the difference of the diameter of the zone of inhibition in the levofloxacin containing plate minus the diameter of the zone of inhibition in the water containing control plate.
*S-isomer;
**R-isomer;
Absence of an asterisk indicates that the substance is a racemic compound.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention claimed is:

1. An efflux pump inhibitor compound selected from the group consisting of

Isopropyl 1-cyclopropyl-6-fluoro-8-methoxy-1,4-dihydro-7-(4'-amino-3',3'-dimethyl-piperidin-1-yl}-4-oxo-quinoline-3-carboxylate;

n-Butyl 1-cyclopropyl-6-fluoro-8-methoxy-1,4-dihydro-7-(4'-amino-3',3'-dimethyl-piperidin-1-yl}-4-oxo-quinoline-3-carboxylate;

Benzyl-1-cyclopropyl-6-fluoro-8-methoxy-1,4-dihydro-7-(4'-(t-butoxycarbonyl amino)-3',3'-dimethyl-piperidin-1-yl}-4-oxo-quinoline-3-carboxylate;

(R)-(+)-Ethoxycarbonylmethyl-9-fluoro-6,7-dihydro-8-(4'-hydroxypiperidin-1'-yl)-5-methyl-1-oxo-1H,5H-benzo[i,j]quinolizine-2-carboxylate;

(S)-(–)-N-Methylpiperidin-1-yl-9-fluoro-6,7-dihydro-8-(4'-hydroxypiperidin-1'-yl)-5-methyl-1-oxo-1H,5H-benzo[i,j]quinolizine-2-carboxylate;

(S)-(–)-N-Morpholinoethyl-1-yl-9-fluoro-6,7-dihydro-8-(4'-hydroxypiperidin-1'-yl)-5-methyl-1-oxo-1H,5H-benzo[i,j]quinolizine-2-carboxylate;

(S)-(–)-9-Fluoro-6,7-dihydro-8-(4'-L-alaninyloxy-piperidin-1-yl)-5-methyl-1-oxo-1H,5H-benzo[i,j]quinolizine-2-carboxylic acid hydrochloride;

(S)-(–)-9-Fluoro-6,7-dihydro-8-(4'-D-leucyloxy-piperidin-1-yl)-5-methyl-1-oxo-1H,5H-benzo[i,j]quinolizine-2-carboxylic acid hydrochloride and (RS)-(±)-9-Fluoro-6,7-dihydro-8-(4'-D-phenylalaninyloxy-piperidin-1-yl)-5-methyl-1-oxo-1H,5H-benzo[i,j]quinolizine-2-carboxylic acid hydrochloride.

2. A composition comprising an efflux pump inhibitor compound according to claim 1, an antimicrobial agent and a pharmaceutically acceptable carrier.

3. The composition of claim 2, wherein the antimicrobial agent is an antibacterial agent.

4. The composition of claim 3, wherein the antimicrobial agent is a macrolide or a ketolide.

5. The composition of claim 4, wherein the macrolide or ketolide is selected from the group consisting of erythromycin, clarithromycin, azithromycin, roxithromycin, rokitamycin, spiramycin, josamycin and telithromycin.

6. The composition of claim 2, wherein the antimicrobial agent is a fluoroquinolone.

7. The composition of claim 6, wherein said fluoroquinolone is selected from the group consisting of ciprofloxacin, norfloxacin, levofloxacin, clinafloxacin, sitafloxacin, gatifloxacin, moxifloxacin, trovafloxacin, gemifloxacin and nadifloxacin.

8. The composition of claim 2, wherein the antimicrobial agent is selected from ciprofloxacin, levofloxacin, ofloxacin, gemifloxacin, nadifloxacin azithromycin and erythromycin.

9. A composition according to claim 2, wherein the antimicrobial agent is levofloxacin.

10. A composition according to claim 2, wherein the antimicrobial agent is azithromycin.

11. A composition according to claim 2, wherein the antimicrobial agent is ciprofloxacin.

12. A method for treating a microbial infection comprising administering an effective amount of an efflux pump inhibitor compound according to claim 1 and an antimicrobial agent to a patient in need thereof.

13. The method according to claim 12 wherein the patient is a human or animal.

14. The method according to claim 12 wherein the patient is a human.

15. A method for suppressing growth of a microbe comprising administering an efflux pump inhibitor compound according to claim 1 and an antimicrobial agent in a concentration below the MIC of the microbe to a patient in need thereof.

16. The method according to claim 15 wherein the patient is a human or animal.

17. The method according to claim 15 wherein the patient is a human.

18. A method for suppressing growth of a microbe comprising exposing the microbe to an efflux pump inhibitor compound according to claim 1 and an antimicrobial agent in a concentration below the MIC of the microbe.

19. The method according to claim 12 wherein the efflux pump is a Mef A or Mef E pump.

20. The method according to claim 15 wherein the efflux pump is Mef A or Mef E pump.

21. The method according to claim 12 wherein the efflux pump is selected from the group consisting of NorA, PmrA, QacA and QacB pump.

22. The method according to claim 15 wherein the efflux pump is selected from the group consisting of NorA, PmrA, QacA and QacB pump.

23. The method according to claim 12, wherein the microbial infection is caused by a microbe expressing an efflux pump is a Gram negative organism-bearing one or more MexAB-OprM, MexCD-OprJ, MexEF-OprM, MexXY-OprM, ARcrAB-TolC, AcrEF, MarA, SoxS, and Tet pumps.

24. The method according to claim 15 wherein the microbe is a Gram negative organism-bearing one or more MexAB-OprM, MexCD-OprJ, MexEF-OprM, MexXY-OprM, ARcrAB-TolC, AcrEF, MarA, SoxS, and Tet pumps.

25. The method according to claim 12 wherein the microbial infection is caused by a bacterium.

26. The method according to claim 15 wherein the microbe is a bacterium.

27. The method according to claim 25, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Burkholderia pseudomallei, Aeromonas hydrophilia, Escherichia coli, Citrobacter freundii, Salmonella typhimurium, Salmonella enterica Serovar typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus,* and *Rickettsia prowazsekii.*

28. The method according to claim 26, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Burkholderia pseudomallei, Aeromonas hydrophilia, Escherichia coli, Citrobacter freundii, Salmonella typhimurium, Salmonella enterica Serovar typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides* eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, Staphylococcus saccharolyticus, and Rickettsia prowazsekii.

29. The method according to claim 25, wherein the bacterium is selected from the group consisting of Streptococcus pneumoniae, Streptococcus pyogenes, Pseudomonas aeruginosa, Escherischia coli, and Staphylococcus aureus.

30. The method according to claim 26, wherein the bacterium is selected from the group consisting of Streptococcus pneumoniae, Streptococcus pyogenes, Pseudomonas aeruginosa, Escherischia coli, and Staphylococcus aureus.

31. The method according to claim 12, wherein said antimicrobial agent is selected from the group consisting of quinolone, tetracycline, beta-lactam, coumermycin, chloramphenicol, glycopeptide, aminoglycoside, macrolide, rifamycin, and oxazolidinone.

32. The method according to claim 15, wherein said antimicrobial agent is selected from the group consisting of quinolone, tetracycline, beta-lactam, coumermycin, chloramphenicol, glycopeptide, aminoglycoside, macrolide, rifamycin, and oxazolidinone.

* * * * *